(12) United States Patent
Yang et al.

(10) Patent No.: US 11,679,265 B2
(45) Date of Patent: Jun. 20, 2023

(54) LEAD-IN-LEAD SYSTEMS AND METHODS FOR CARDIAC THERAPY

(71) Applicant: Medtronic, Inc., Minneapolis, MN (US)

(72) Inventors: Zhongping Yang, Woodbury, MN (US); Derek Young, Beegden (NL)

(73) Assignee: Medtronic, Inc., Minneapolis, MN (US)

( * ) Notice: Subject to any disclaimer, the term of this patent is extended or adjusted under 35 U.S.C. 154(b) by 434 days.

(21) Appl. No.: 16/780,036

(22) Filed: Feb. 3, 2020

(65) Prior Publication Data

US 2020/0261725 A1 Aug. 20, 2020

Related U.S. Application Data

(60) Provisional application No. 62/805,749, filed on Feb. 14, 2019.

(51) Int. Cl.
| | | |
|---|---|---|
| *A61N 1/368* | (2006.01) | |
| *A61N 1/05* | (2006.01) | |
| *A61N 1/39* | (2006.01) | |
| *A61N 1/362* | (2006.01) | |
| *A61B 17/34* | (2006.01) | |

(52) U.S. Cl.
CPC ......... *A61N 1/3684* (2013.01); *A61N 1/0587* (2013.01); *A61B 17/3468* (2013.01); *A61N 1/362* (2013.01); *A61N 1/3956* (2013.01)

(58) Field of Classification Search
CPC .. A61N 1/3956; A61N 1/0587; A61N 1/3684; A61N 1/3622
See application file for complete search history.

(56) References Cited

U.S. PATENT DOCUMENTS

| | | |
|---|---|---|
| 3,835,864 A | 9/1974 | Rasor et al. |
| 3,865,118 A | 2/1975 | Bures |
| 3,943,936 A | 3/1976 | Rasor et al. |
| 3,949,757 A | 4/1976 | Sabel |

(Continued)

FOREIGN PATENT DOCUMENTS

| | | |
|---|---|---|
| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — Alyssa M Alter

(74) *Attorney, Agent, or Firm* — Mueting Raasch Group

(57) ABSTRACT

A lead-in-lead system may include a first implantable lead having a first electrode and a second implantable lead having a second electrode guided by the first implantable lead to an implantation site. The second electrode may be implanted in a patient's heart distal to the first electrode at the same implantation site or at a second implantation site. Various methods may be used to deliver the lead-in-lead system to one or more implantation sites including at the triangle of Koch for ventricle-from-atrium (VfA) therapy, at the right ventricular septal wall for dual bundle-branch pacing, or in the coronary vasculature for left side sensing and pacing.

28 Claims, 23 Drawing Sheets

(56) References Cited

U.S. PATENT DOCUMENTS

| | | | |
|---|---|---|---|
| 4,142,530 A | 3/1979 | Wittkampf | |
| 4,151,513 A | 4/1979 | Menken et al. | |
| 4,157,720 A | 6/1979 | Greatbatch | |
| RE30,366 E | 8/1980 | Rasor et al. | |
| 4,243,045 A | 1/1981 | Mass | |
| 4,250,884 A | 2/1981 | Hartlaub et al. | |
| 4,256,115 A | 3/1981 | Bilitch | |
| 4,263,919 A | 4/1981 | Levin | |
| 4,280,502 A | 7/1981 | Baker, Jr. et al. | |
| 4,289,144 A | 9/1981 | Gilman | |
| 4,310,000 A | 1/1982 | Lindemans | |
| 4,312,354 A | 1/1982 | Walters | |
| 4,323,081 A | 4/1982 | Wiebusch | |
| 4,332,259 A | 6/1982 | McCorkle, Jr. | |
| 4,357,946 A | 11/1982 | Dutcher et al. | |
| 4,365,639 A | 12/1982 | Goldreyer | |
| 4,374,382 A | 2/1983 | Markowitz | |
| 4,393,883 A | 7/1983 | Smyth et al. | |
| 4,440,173 A | 4/1984 | Hudziak et al. | |
| 4,476,868 A | 10/1984 | Thompson | |
| 4,479,500 A | 10/1984 | Smits | |
| 4,522,208 A | 6/1985 | Buffet | |
| 4,537,200 A | 8/1985 | Widrow | |
| 4,546,777 A | 10/1985 | Groch et al. | |
| 4,556,063 A | 12/1985 | Thompson et al. | |
| 4,562,841 A | 1/1986 | Brockway et al. | |
| 4,574,814 A | 3/1986 | Buffet | |
| 4,593,702 A | 6/1986 | Ski et al. | |
| 4,593,955 A | 6/1986 | Leiber | |
| 4,630,611 A | 12/1986 | King | |
| 4,635,639 A | 1/1987 | Hakala et al. | |
| 4,643,201 A * | 2/1987 | Stokes | A61N 1/056 607/122 |
| 4,674,508 A | 6/1987 | DeCote | |
| 4,712,554 A | 12/1987 | Garson | |
| 4,729,376 A | 3/1988 | DeCote | |
| 4,754,753 A | 7/1988 | King | |
| 4,759,366 A | 7/1988 | Callaghan | |
| 4,776,338 A | 10/1988 | Lekholm et al. | |
| 4,787,389 A | 11/1988 | Tarjan | |
| 4,793,353 A | 12/1988 | Borkan | |
| 4,819,662 A | 4/1989 | Heil et al. | |
| 4,830,006 A | 5/1989 | Haluska et al. | |
| 4,858,610 A | 8/1989 | Callaghan et al. | |
| 4,865,037 A | 9/1989 | Chin et al. | |
| 4,886,064 A | 12/1989 | Strandberg | |
| 4,887,609 A | 12/1989 | Cole, Jr. | |
| 4,928,688 A | 5/1990 | Mower | |
| 4,953,564 A | 9/1990 | Berthelsen | |
| 4,967,746 A | 11/1990 | Vandegriff | |
| 4,987,897 A | 1/1991 | Funke | |
| 4,989,602 A | 2/1991 | Sholder et al. | |
| 5,012,806 A | 5/1991 | De Bellis | |
| 5,036,849 A | 8/1991 | Hauck et al. | |
| 5,040,534 A | 8/1991 | Mann et al. | |
| 5,058,581 A | 10/1991 | Silvian | |
| 5,078,134 A | 1/1992 | Heilman et al. | |
| 5,107,850 A | 4/1992 | Olive | |
| 5,109,845 A | 5/1992 | Yuuchi et al. | |
| 5,113,859 A | 5/1992 | Funke | |
| 5,113,869 A | 5/1992 | Nappholz et al. | |
| 5,117,824 A | 6/1992 | Keimel et al. | |
| 5,127,401 A | 7/1992 | Grievous et al. | |
| 5,133,353 A | 7/1992 | Hauser | |
| 5,144,950 A | 9/1992 | Stoop et al. | |
| 5,154,170 A | 10/1992 | Bennett et al. | |
| 5,170,784 A | 12/1992 | Ramon et al. | |
| 5,174,286 A | 12/1992 | Chirife | |
| 5,174,289 A | 12/1992 | Cohen | |
| 5,179,945 A | 1/1993 | Van Hofwegen et al. | |
| 5,193,539 A | 3/1993 | Schulman et al. | |
| 5,193,540 A | 3/1993 | Schulman et al. | |
| 5,241,961 A | 9/1993 | Henry | |
| 5,243,977 A | 9/1993 | Trabucco et al. | |
| 5,255,692 A | 10/1993 | Neubauer et al. | |
| 5,259,387 A | 11/1993 | dePinto | |
| 5,269,326 A | 12/1993 | Verrier | |
| 5,284,136 A | 2/1994 | Hauck et al. | |
| 5,300,107 A | 4/1994 | Stokes et al. | |
| 5,301,677 A | 4/1994 | Hsung | |
| 5,305,760 A | 4/1994 | McKown et al. | |
| 5,312,439 A | 5/1994 | Loeb | |
| 5,313,953 A | 5/1994 | Yomtov et al. | |
| 5,314,459 A | 5/1994 | Swanson et al. | |
| 5,318,594 A | 6/1994 | Limousin et al. | |
| 5,318,597 A | 6/1994 | Hauck et al. | |
| 5,324,316 A | 6/1994 | Schulman et al. | |
| 5,331,966 A | 7/1994 | Bennett et al. | |
| 5,334,222 A | 8/1994 | Salo et al. | |
| 5,342,408 A | 8/1994 | Decoriolis et al. | |
| 5,370,667 A | 12/1994 | Alt | |
| 5,372,606 A | 12/1994 | Lang et al. | |
| 5,376,106 A | 12/1994 | Stahmann et al. | |
| 5,383,915 A | 1/1995 | Adams | |
| 5,388,578 A | 2/1995 | Yomtov et al. | |
| 5,404,877 A | 4/1995 | Nolan et al. | |
| 5,405,367 A | 4/1995 | Schulman et al. | |
| 5,411,031 A | 5/1995 | Yomtov | |
| 5,411,525 A | 5/1995 | Swanson et al. | |
| 5,411,535 A | 5/1995 | Fujii et al. | |
| 5,456,691 A | 10/1995 | Snell | |
| 5,458,622 A | 10/1995 | Alt | |
| 5,466,246 A | 11/1995 | Silvian | |
| 5,468,254 A | 11/1995 | Hahn et al. | |
| 5,472,453 A | 12/1995 | Alt | |
| 5,522,866 A | 6/1996 | Fernald | |
| 5,540,727 A | 7/1996 | Tockman et al. | |
| 5,545,186 A | 8/1996 | Olsen et al. | |
| 5,545,202 A | 8/1996 | Dahl et al. | |
| 5,554,177 A | 9/1996 | Kieval et al. | |
| 5,562,711 A | 10/1996 | Yerich et al. | |
| 5,571,146 A | 11/1996 | Jones et al. | |
| 5,591,214 A | 1/1997 | Lu | |
| 5,620,466 A | 4/1997 | Haefner et al. | |
| 5,634,938 A | 6/1997 | Swanson et al. | |
| 5,649,968 A | 7/1997 | Alt et al. | |
| 5,662,688 A | 9/1997 | Haefner et al. | |
| 5,674,259 A | 10/1997 | Gray | |
| 5,683,426 A | 11/1997 | Greenhut et al. | |
| 5,683,432 A | 11/1997 | Goedeke et al. | |
| 5,706,823 A | 1/1998 | Wodlinger | |
| 5,709,215 A | 1/1998 | Perttu et al. | |
| 5,720,770 A | 2/1998 | Nappholz et al. | |
| 5,728,140 A | 3/1998 | Salo et al. | |
| 5,728,154 A | 3/1998 | Crossett et al. | |
| 5,741,314 A | 4/1998 | Daly et al. | |
| 5,741,315 A | 4/1998 | Lee et al. | |
| 5,749,909 A | 5/1998 | Schroeppel et al. | |
| 5,752,976 A | 5/1998 | Duffin et al. | |
| 5,752,977 A | 5/1998 | Grievous et al. | |
| 5,755,736 A | 5/1998 | Gillberg et al. | |
| 5,759,199 A | 6/1998 | Snell et al. | |
| 5,774,501 A | 6/1998 | Halpern et al. | |
| 5,792,195 A | 8/1998 | Carlson et al. | |
| 5,792,202 A | 8/1998 | Rueter | |
| 5,792,203 A | 8/1998 | Schroeppel | |
| 5,792,205 A | 8/1998 | Alt et al. | |
| 5,792,208 A | 8/1998 | Gray | |
| 5,800,467 A | 9/1998 | Park et al. | |
| 5,814,089 A | 9/1998 | Stokes et al. | |
| 5,817,130 A | 10/1998 | Cox et al. | |
| 5,827,216 A | 10/1998 | Igo et al. | |
| 5,836,985 A | 11/1998 | Goyal et al. | |
| 5,836,987 A | 11/1998 | Baumann et al. | |
| 5,842,977 A | 12/1998 | Lesho et al. | |
| 5,855,593 A | 1/1999 | Olson et al. | |
| 5,873,894 A | 2/1999 | Vandegriff et al. | |
| 5,891,184 A | 4/1999 | Lee et al. | |
| 5,897,586 A | 4/1999 | Molina | |
| 5,899,876 A | 5/1999 | Flower | |
| 5,899,928 A | 5/1999 | Sholder et al. | |
| 5,919,214 A | 7/1999 | Ciciarelli et al. | |
| 5,928,271 A | 7/1999 | Hess et al. | |
| 5,935,078 A | 8/1999 | Feierbach | |

(56) References Cited

U.S. PATENT DOCUMENTS

| | | | |
|---|---|---|---|
| 5,941,906 | A | 8/1999 | Barreras et al. |
| 5,944,744 | A | 8/1999 | Paul et al. |
| 5,954,757 | A | 9/1999 | Gray |
| 5,964,795 | A * | 10/1999 | McVenes ............... A61N 1/056 607/122 |
| 5,978,713 | A | 11/1999 | Prutchi et al. |
| 5,991,660 | A | 11/1999 | Goyal |
| 5,991,661 | A | 11/1999 | Park et al. |
| 5,999,848 | A | 12/1999 | Gord et al. |
| 5,999,857 | A | 12/1999 | Weijand et al. |
| 6,016,445 | A | 1/2000 | Baura |
| 6,026,320 | A | 2/2000 | Carlson et al. |
| 6,029,085 | A | 2/2000 | Olson et al. |
| 6,041,250 | A | 3/2000 | dePinto |
| 6,044,298 | A | 3/2000 | Salo et al. |
| 6,044,300 | A | 3/2000 | Gray |
| 6,055,454 | A | 4/2000 | Heemels |
| 6,073,050 | A | 6/2000 | Griffith |
| 6,076,016 | A | 6/2000 | Feierbach |
| 6,077,236 | A | 6/2000 | Cunningham |
| 6,080,187 | A | 6/2000 | Alt et al. |
| 6,083,248 | A | 7/2000 | Thompson |
| 6,106,551 | A | 8/2000 | Crossett et al. |
| 6,115,636 | A | 9/2000 | Ryan |
| 6,128,526 | A | 10/2000 | Stadler et al. |
| 6,132,456 | A | 10/2000 | Sommer et al. |
| 6,141,581 | A | 10/2000 | Olson et al. |
| 6,141,588 | A | 10/2000 | Cox et al. |
| 6,141,592 | A | 10/2000 | Pauly |
| 6,144,879 | A | 11/2000 | Gray |
| 6,162,195 | A | 12/2000 | Igo et al. |
| 6,164,284 | A | 12/2000 | Schulman et al. |
| 6,167,310 | A | 12/2000 | Grevious |
| 6,201,993 | B1 | 3/2001 | Kruse et al. |
| 6,208,894 | B1 | 3/2001 | Schulman et al. |
| 6,211,799 | B1 | 4/2001 | Post et al. |
| 6,221,011 | B1 | 4/2001 | Bardy |
| 6,240,316 | B1 | 5/2001 | Richmond et al. |
| 6,240,317 | B1 | 5/2001 | Villaseca et al. |
| 6,256,534 | B1 | 7/2001 | Dahl |
| 6,259,947 | B1 | 7/2001 | Olson et al. |
| 6,266,558 | B1 | 7/2001 | Gozani et al. |
| 6,266,567 | B1 | 7/2001 | Ishikawa et al. |
| 6,270,457 | B1 | 8/2001 | Bardy |
| 6,272,377 | B1 | 8/2001 | Sweeney et al. |
| 6,273,856 | B1 | 8/2001 | Sun et al. |
| 6,277,072 | B1 | 8/2001 | Bardy |
| 6,280,380 | B1 | 8/2001 | Bardy |
| 6,285,903 | B1 | 9/2001 | Rosenthal et al. |
| 6,285,907 | B1 | 9/2001 | Kramer et al. |
| 6,292,698 | B1 | 9/2001 | Duffin et al. |
| 6,295,473 | B1 | 9/2001 | Rosar |
| 6,297,943 | B1 | 10/2001 | Carson |
| 6,298,271 | B1 | 10/2001 | Weijand |
| 6,307,751 | B1 | 10/2001 | Bodony et al. |
| 6,312,378 | B1 | 11/2001 | Bardy |
| 6,315,721 | B2 | 11/2001 | Schulman et al. |
| 6,336,903 | B1 | 1/2002 | Bardy |
| 6,345,202 | B2 | 2/2002 | Richmond et al. |
| 6,351,667 | B1 | 2/2002 | Godie |
| 6,351,669 | B1 | 2/2002 | Hartley et al. |
| 6,353,759 | B1 | 3/2002 | Hartley et al. |
| 6,358,203 | B2 | 3/2002 | Bardy |
| 6,361,780 | B1 | 3/2002 | Ley et al. |
| 6,368,284 | B1 | 4/2002 | Bardy |
| 6,371,922 | B1 | 4/2002 | Baumann et al. |
| 6,393,316 | B1 | 5/2002 | Gillberg et al. |
| 6,398,728 | B1 | 6/2002 | Bardy |
| 6,400,982 | B2 | 6/2002 | Sweeney et al. |
| 6,400,990 | B1 | 6/2002 | Silvian |
| 6,408,208 | B1 | 6/2002 | Sun |
| 6,409,674 | B1 | 6/2002 | Brockway et al. |
| 6,411,848 | B2 | 6/2002 | Kramer et al. |
| 6,424,865 | B1 | 7/2002 | Ding |
| 6,434,429 | B1 | 8/2002 | Kraus et al. |
| 6,438,410 | B2 | 8/2002 | Hsu et al. |
| 6,438,417 | B1 | 8/2002 | Rockwell et al. |
| 6,438,421 | B1 | 8/2002 | Stahmann et al. |
| 6,440,066 | B1 | 8/2002 | Bardy |
| 6,441,747 | B1 | 8/2002 | Khair et al. |
| 6,442,426 | B1 | 8/2002 | Kroll |
| 6,442,432 | B2 | 8/2002 | Lee |
| 6,443,891 | B1 | 9/2002 | Grevious |
| 6,445,953 | B1 | 9/2002 | Bulkes et al. |
| 6,453,200 | B1 | 9/2002 | Koslar |
| 6,459,929 | B1 | 10/2002 | Hopper et al. |
| 6,470,215 | B1 | 10/2002 | Kraus et al. |
| 6,471,645 | B1 | 10/2002 | Warkentin et al. |
| 6,480,745 | B2 | 11/2002 | Nelson et al. |
| 6,487,443 | B2 | 11/2002 | Olson et al. |
| 6,490,487 | B1 | 12/2002 | Kraus et al. |
| 6,498,951 | B1 | 12/2002 | Larson et al. |
| 6,507,755 | B1 | 1/2003 | Gozani et al. |
| 6,507,759 | B1 | 1/2003 | Prutchi et al. |
| 6,508,771 | B1 | 1/2003 | Padmanabhan et al. |
| 6,512,940 | B1 | 1/2003 | Brabec et al. |
| 6,522,915 | B1 | 2/2003 | Ceballos et al. |
| 6,526,311 | B2 | 2/2003 | Begemann |
| 6,539,253 | B2 | 3/2003 | Thompson et al. |
| 6,542,775 | B2 | 4/2003 | Ding et al. |
| 6,544,270 | B1 | 4/2003 | Zhang |
| 6,553,258 | B2 | 4/2003 | Stahmann et al. |
| 6,561,975 | B1 | 5/2003 | Pool et al. |
| 6,564,807 | B1 | 5/2003 | Schulman et al. |
| 6,574,506 | B2 | 6/2003 | Kramer et al. |
| 6,584,351 | B1 | 6/2003 | Ekwall |
| 6,584,352 | B2 | 6/2003 | Combs et al. |
| 6,597,948 | B1 | 7/2003 | Rockwell et al. |
| 6,597,951 | B2 | 7/2003 | Kramer et al. |
| 6,609,027 | B2 | 8/2003 | Kroll et al. |
| 6,622,046 | B2 | 9/2003 | Fraley et al. |
| 6,623,518 | B2 | 9/2003 | Thompson et al. |
| 6,628,985 | B2 | 9/2003 | Sweeney et al. |
| 6,647,292 | B1 | 11/2003 | Bardy et al. |
| 6,666,844 | B1 | 12/2003 | Igo et al. |
| 6,689,117 | B2 | 2/2004 | Sweeney et al. |
| 6,690,959 | B2 | 2/2004 | Thompson |
| 6,694,189 | B2 | 2/2004 | Begemann |
| 6,704,602 | B2 | 3/2004 | Berg et al. |
| 6,711,443 | B2 | 3/2004 | Osypka |
| 6,718,206 | B2 | 4/2004 | Casvant |
| 6,718,212 | B2 | 4/2004 | Parry et al. |
| 6,721,597 | B1 | 4/2004 | Bardy et al. |
| 6,738,670 | B1 | 5/2004 | Almendinger et al. |
| 6,738,674 | B2 | 5/2004 | Osypka |
| 6,746,797 | B2 | 6/2004 | Benson et al. |
| 6,749,566 | B2 | 6/2004 | Russ |
| 6,754,528 | B2 | 6/2004 | Bardy et al. |
| 6,758,810 | B2 | 7/2004 | Lebel et al. |
| 6,763,269 | B2 | 7/2004 | Cox |
| 6,768,923 | B2 | 7/2004 | Ding et al. |
| 6,778,860 | B2 | 8/2004 | Ostroff et al. |
| 6,788,971 | B1 | 9/2004 | Sloman et al. |
| 6,788,974 | B2 | 9/2004 | Bardy et al. |
| 6,804,558 | B2 | 10/2004 | Haller et al. |
| 6,807,442 | B1 | 10/2004 | Myklebust et al. |
| 6,847,844 | B2 | 1/2005 | Sun et al. |
| 6,869,404 | B2 | 3/2005 | Schulhauser et al. |
| 6,871,095 | B2 | 3/2005 | Stahmann et al. |
| 6,871,096 | B2 | 3/2005 | Hill |
| 6,878,112 | B2 | 4/2005 | Linberg et al. |
| 6,885,889 | B2 | 4/2005 | Chinchoy |
| 6,892,094 | B2 | 5/2005 | Ousdigian et al. |
| 6,897,788 | B2 | 5/2005 | Khair et al. |
| 6,904,315 | B2 | 6/2005 | Panken et al. |
| 6,922,592 | B2 | 7/2005 | Thompson et al. |
| 6,931,282 | B2 | 8/2005 | Esler |
| 6,931,286 | B2 | 8/2005 | Sigg et al. |
| 6,934,585 | B1 | 8/2005 | Schloss et al. |
| 6,941,169 | B2 | 9/2005 | Pappu |
| 6,957,107 | B2 | 10/2005 | Rogers et al. |
| 6,978,176 | B2 | 12/2005 | Lattouf |
| 6,980,675 | B2 | 12/2005 | Evron et al. |
| 6,985,773 | B2 | 1/2006 | Von Arx et al. |

(56) References Cited

U.S. PATENT DOCUMENTS

| | | |
|---|---|---|
| 6,988,007 B1 | 1/2006 | Morgan et al. |
| 6,990,375 B2 | 1/2006 | Kloss et al. |
| 6,993,389 B2 | 1/2006 | Ding et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,176 B2 | 3/2006 | Ding et al. |
| 7,013,178 B2 | 3/2006 | Reinke et al. |
| 7,027,871 B2 | 4/2006 | Burnes et al. |
| 7,031,711 B2 | 4/2006 | Brown et al. |
| 7,031,771 B2 | 4/2006 | Brown et al. |
| 7,035,684 B2 | 4/2006 | Lee et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,335 B2 | 7/2006 | Klein et al. |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,177,704 B2 | 2/2007 | Laske et al. |
| 7,181,284 B2 | 2/2007 | Burnes et al. |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,231,248 B2 | 6/2007 | Kramer et al. |
| 7,231,253 B2 | 6/2007 | Tidemand et al. |
| 7,236,821 B2 | 6/2007 | Cates et al. |
| 7,236,829 B1 | 6/2007 | Farazi et al. |
| 7,245,973 B2 | 7/2007 | Liu et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,286,866 B2 | 10/2007 | Okerlund et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,307,321 B1 | 12/2007 | Avanzino |
| 7,308,297 B2 | 12/2007 | Reddy et al. |
| 7,308,299 B2 | 12/2007 | Burrell et al. |
| 7,310,556 B2 | 12/2007 | Bulkes |
| 7,317,950 B2 | 1/2008 | Lee |
| 7,319,905 B1 | 1/2008 | Morgan et al. |
| 7,321,677 B2 | 1/2008 | Evron et al. |
| 7,321,798 B2 | 1/2008 | Muhlenberg et al. |
| 7,333,853 B2 | 2/2008 | Mazar et al. |
| 7,336,994 B2 | 2/2008 | Hettrick et al. |
| 7,346,381 B2 | 3/2008 | Okerlund et al. |
| 7,346,393 B2 | 3/2008 | Spinelli et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,386,351 B2 | 6/2008 | Hine et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,454,248 B2 | 11/2008 | Burrell et al. |
| 7,496,409 B2 | 2/2009 | Greenhut et al. |
| 7,496,410 B2 | 2/2009 | Heil |
| 7,499,743 B2 | 3/2009 | Vass et al. |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Keisch et al. |
| 7,546,166 B2 | 6/2009 | Michels et al. |
| 7,558,626 B2 | 7/2009 | Corbucci |
| 7,558,631 B2 | 7/2009 | Cowan et al. |
| 7,565,190 B2 | 7/2009 | Okerlund et al. |
| 7,565,195 B1 | 7/2009 | Kroll et al. |
| 7,584,002 B2 | 9/2009 | Burnes et al. |
| 7,587,074 B2 | 9/2009 | Zarkh et al. |
| 7,590,455 B2 | 9/2009 | Heruth et al. |
| 7,599,730 B2 | 10/2009 | Hunter et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,613,500 B2 | 11/2009 | Vass et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,764 B2 | 12/2009 | Ding et al. |
| 7,630,767 B1 | 12/2009 | Poore et al. |
| 7,634,313 B1 | 12/2009 | Kroll et al. |
| 7,635,541 B2 | 12/2009 | Scott et al. |
| 7,637,867 B2 | 12/2009 | Zdeblick |
| 7,640,057 B2 | 12/2009 | Libbus et al. |
| 7,640,060 B2 | 12/2009 | Zdeblick |
| 7,647,109 B2 | 1/2010 | Hastings et al. |
| 7,647,124 B2 | 1/2010 | Williams |
| 7,650,186 B2 | 1/2010 | Hastings et al. |
| 7,657,311 B2 | 2/2010 | Bardy et al. |
| 7,657,313 B2 | 2/2010 | Rom |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,706,879 B2 | 4/2010 | Burnes et al. |
| 7,713,194 B2 | 5/2010 | Zdeblick |
| 7,713,195 B2 | 5/2010 | Zdeblick |
| 7,729,782 B2 | 6/2010 | William et al. |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,954 B1 | 6/2010 | Kroll et al. |
| 7,738,958 B2 | 6/2010 | Zdeblick et al. |
| 7,738,964 B2 | 6/2010 | Von Arx et al. |
| 7,742,629 B2 | 6/2010 | Zarkh et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,047 B2 | 6/2010 | Okerlund et al. |

(56) References Cited

U.S. PATENT DOCUMENTS

| | | |
|---|---|---|
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,778,685 B2 | 8/2010 | Evron et al. |
| 7,778,686 B2 | 8/2010 | Vass et al. |
| 7,783,362 B2 | 8/2010 | Whitehurst et al. |
| 7,792,580 B2 | 9/2010 | Borowitz et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,813,785 B2 | 10/2010 | Okerlund et al. |
| 7,815,577 B2 | 10/2010 | Krishnan |
| 7,840,266 B2 | 11/2010 | Libbus et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,877,144 B2 | 1/2011 | Coles, Jr. et al. |
| 7,881,786 B2 | 2/2011 | Jackson |
| 7,881,791 B2 | 2/2011 | Sambelashvili et al. |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Keisch et al. |
| 7,894,885 B2 | 2/2011 | Bartal et al. |
| 7,894,894 B2 | 2/2011 | Stadler et al. |
| 7,894,902 B2 | 2/2011 | Rom |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,912,544 B1 | 3/2011 | Min et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,027 B2 | 4/2011 | Prakash et al. |
| 7,930,040 B1 | 4/2011 | Keisch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,941,218 B2 | 5/2011 | Sambelashvili et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,063 B2 | 8/2011 | Vass et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,002,718 B2 | 8/2011 | Buchholtz et al. |
| 8,010,191 B2 | 8/2011 | Zhu et al. |
| 8,010,209 B2 | 8/2011 | Jacobson |
| 8,013,133 B2 | 9/2011 | Sharma et al. |
| 8,014,861 B2 | 9/2011 | Zhu et al. |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,065 B2 | 10/2011 | Burnes et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,185 B2 | 11/2011 | Hunter et al. |
| 8,060,212 B1 | 11/2011 | Rios et al. |
| 8,065,018 B2 | 11/2011 | Haubrich et al. |
| 8,068,920 B2 | 11/2011 | Gaudiani |
| 8,073,542 B2 | 12/2011 | Doerr |
| 8,078,278 B2 | 12/2011 | Penner |
| 8,078,283 B2 | 12/2011 | Cowan et al. |
| 8,078,287 B2 | 12/2011 | Liu et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,105,714 B2 | 1/2012 | Schmidt et al. |
| 8,112,148 B2 | 2/2012 | Giftakis et al. |
| 8,112,160 B2 | 2/2012 | Foster |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,145,308 B2 | 3/2012 | Sambelashvili et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,428 B2 | 5/2012 | Kaiser et al. |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,590 B2 | 6/2012 | Sambelashvili et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,041 B2 | 7/2012 | Van Gelder et al. |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,234,608 B2 | 7/2012 | Ishikawa |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,014 B2 | 11/2012 | Maskara et al. |
| 8,321,021 B2 | 11/2012 | Kisker et al. |
| 8,321,036 B2 | 11/2012 | Brockway et al. |

(56) References Cited

U.S. PATENT DOCUMENTS

| | | |
|---|---|---|
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,027 B2 | 1/2013 | Spinelli et al. |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,383,269 B2 | 2/2013 | Scott et al. |
| 8,386,051 B2 | 2/2013 | Bas |
| 8,391,964 B2 | 3/2013 | Musley et al. |
| 8,391,981 B2 | 3/2013 | Mosesov |
| 8,391,990 B2 | 3/2013 | Smith et al. |
| 8,401,616 B2 | 3/2013 | Verard et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,406,899 B2 | 3/2013 | Reddy et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,716 B2 | 4/2013 | Mullen et al. |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,467,871 B2 | 6/2013 | Maskara |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,509,916 B2 | 8/2013 | Byrd et al. |
| 8,515,559 B2 | 8/2013 | Roberts et al. |
| 8,521,268 B2 | 8/2013 | Zhang et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,560,068 B2 | 10/2013 | Forslund |
| 8,565,880 B2 | 10/2013 | Dong et al. |
| 8,565,882 B2 | 10/2013 | Matoes |
| 8,565,897 B2 | 10/2013 | Regnier et al. |
| 8,571,678 B2 | 10/2013 | Wang |
| 8,577,327 B2 | 11/2013 | Makdissi et al. |
| 8,588,907 B2 | 11/2013 | Arcot-krishnamurthy et al. |
| 8,588,926 B2 | 11/2013 | Moore et al. |
| 8,594,775 B2 | 11/2013 | Ghosh et al. |
| 8,606,369 B2 | 12/2013 | Williams et al. |
| 8,612,002 B2 | 12/2013 | Faltys et al. |
| 8,615,310 B2 | 12/2013 | Khairkhahan et al. |
| 8,617,082 B2 | 12/2013 | Zhang et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,333 B2 | 1/2014 | Stadler et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,824 B2 | 3/2014 | Anderson et al. |
| 8,670,842 B1 | 3/2014 | Bornzin et al. |
| 8,676,314 B2 | 3/2014 | Maskara et al. |
| 8,676,319 B2 | 3/2014 | Knoll |
| 8,676,335 B2 | 3/2014 | Katoozi et al. |
| 8,688,234 B2 | 4/2014 | Ortega et al. |
| 8,700,173 B2 | 4/2014 | Edlund |
| 8,700,181 B2 | 4/2014 | Bornzin et al. |
| 8,705,599 B2 | 4/2014 | Dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,731,642 B2 | 5/2014 | Zarkh et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,750,994 B2 | 6/2014 | Ghosh et al. |
| 8,750,998 B1 | 6/2014 | Ghosh et al. |
| 8,755,884 B2 | 6/2014 | Demmer et al. |
| 8,758,365 B2 | 6/2014 | Bonner et al. |
| 8,761,880 B2 | 6/2014 | Maskara et al. |
| 8,768,459 B2 | 7/2014 | Ghosh et al. |
| 8,768,483 B2 | 7/2014 | Schmitt et al. |
| 8,774,572 B2 | 7/2014 | Hamamoto |
| 8,777,904 B2 | 7/2014 | Kassab et al. |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,834,384 B2 | 9/2014 | Krishnan |
| 8,855,789 B2 | 10/2014 | Jacobson |
| 8,861,830 B2 | 10/2014 | Brada et al. |
| 8,868,186 B2 | 10/2014 | Kroll |
| 8,874,237 B2 | 10/2014 | Schilling et al. |
| 8,886,307 B2 | 11/2014 | Sambelashvili et al. |
| 8,886,311 B2 | 11/2014 | Anderson et al. |
| 8,886,339 B2 | 11/2014 | Faltys et al. |
| 8,903,473 B2 | 12/2014 | Rogers et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,805 B2 | 1/2015 | Shuros et al. |
| 8,942,806 B2 | 1/2015 | Sheldon et al. |
| 8,948,883 B2 | 2/2015 | Eggen et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,033,996 B1 | 5/2015 | West |
| 9,037,262 B2 | 5/2015 | Regnier et al. |
| 9,042,984 B2 | 5/2015 | Demmer et al. |
| 9,072,872 B2 | 7/2015 | Asleson et al. |
| 9,072,911 B2 | 7/2015 | Hastings et al. |

(56) References Cited

U.S. PATENT DOCUMENTS

| | | |
|---|---|---|
| 9,072,913 B2 | 7/2015 | Jacobson |
| 9,101,281 B2 | 8/2015 | Reinert et al. |
| 9,119,959 B2 | 9/2015 | Rys et al. |
| 8,954,147 B2 | 10/2015 | Arcot-krishnamurthy et al. |
| 9,155,882 B2 | 10/2015 | Grubac et al. |
| 9,162,066 B2 | 10/2015 | Hedberg et al. |
| 9,168,372 B2 | 10/2015 | Fain |
| 9,168,380 B1 | 10/2015 | Greenhut et al. |
| 9,168,382 B2 | 10/2015 | Shuros et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashbili et al. |
| 9,302,115 B2 | 4/2016 | Molin et al. |
| 9,320,446 B2 | 4/2016 | Gillberg et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Regnier et al. |
| 9,457,193 B2 | 10/2016 | Klimovitch et al. |
| 9,474,457 B2 | 10/2016 | Ghosh et al. |
| 9,486,151 B2 | 11/2016 | Ghosh et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,517,336 B2 | 12/2016 | Eggen et al. |
| 9,522,276 B2 | 12/2016 | Shen et al. |
| 9,522,280 B2 | 12/2016 | Fishier et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,550,058 B2 | 1/2017 | Foster |
| 9,561,382 B2 | 2/2017 | Persson et al. |
| 9,566,012 B2 | 2/2017 | Greenhut et al. |
| 9,579,500 B2 | 2/2017 | Rys et al. |
| 9,623,234 B2 | 4/2017 | Anderson |
| 9,636,511 B2 | 5/2017 | Carney et al. |
| 9,643,014 B2 | 5/2017 | Zhang et al. |
| 9,675,579 B2 | 6/2017 | Rock et al. |
| 9,687,654 B2 | 6/2017 | Sheldon et al. |
| 9,707,399 B2 | 7/2017 | Zielinski et al. |
| 9,717,902 B2 | 8/2017 | Ollivier |
| 9,724,519 B2 | 8/2017 | Demmer et al. |
| 9,789,319 B2 | 10/2017 | Sambelashvil |
| 9,808,628 B2 | 11/2017 | Sheldon et al. |
| 9,808,633 B2 | 11/2017 | Bonner et al. |
| 9,877,789 B2 | 1/2018 | Ghosh |
| 9,924,884 B2 | 3/2018 | Ghosh et al. |
| 10,004,467 B2 | 6/2018 | Lahm et al. |
| 10,064,567 B2 | 9/2018 | Ghosh et al. |
| 10,099,050 B2 | 10/2018 | Chen et al. |
| 10,166,396 B2 | 1/2019 | Schrock et al. |
| 10,251,555 B2 | 4/2019 | Ghosh et al. |
| 10,668,290 B2 | 6/2020 | Ghosh |
| 10,799,703 B2 | 10/2020 | Ghosh et al. |
| 10,850,107 B2 | 12/2020 | Li et al. |
| 10,850,108 B2 | 12/2020 | Li et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0049476 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Hailer et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0004549 A1 | 1/2003 | Hill et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0092995 A1 | 5/2003 | Thompson |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2003/0199938 A1 | 10/2003 | Smits et al. |
| 2003/0199956 A1 | 10/2003 | Struble et al. |
| 2004/0024435 A1 | 2/2004 | Leckrone et al. |
| 2004/0054388 A1 | 3/2004 | Osypka |
| 2004/0064158 A1 | 4/2004 | Klein et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0153127 A1 | 8/2004 | Gordon et al. |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Strand et al. |
| 2004/0176818 A1 | 9/2004 | Strand et al. |
| 2004/0176830 A1 | 9/2004 | Fang |

(56) References Cited

U.S. PATENT DOCUMENTS

| | | |
|---|---|---|
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0230283 A1 | 11/2004 | Prinzen et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0008210 A1 | 1/2005 | Evron et al. |
| 2005/0038477 A1 | 2/2005 | Kramer et al. |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0137629 A1 | 6/2005 | Dyjach et al. |
| 2005/0137671 A1 | 6/2005 | Liu et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0277990 A1 | 12/2005 | Ostroff et al. |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0074285 A1 | 4/2006 | Zarkh et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0095107 A1 | 5/2006 | Osypka |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0161205 A1 | 7/2006 | Mitrani et al. |
| 2006/0200002 A1 | 9/2006 | Guenst |
| 2006/0206151 A1 | 9/2006 | Lu |
| 2006/0206153 A1 | 9/2006 | Libbus et al. |
| 2006/0212079 A1 | 9/2006 | Routh et al. |
| 2006/0235478 A1 | 10/2006 | Van Gelder et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0016261 A1 | 1/2007 | Dong et al. |
| 2007/0027508 A1 | 2/2007 | Cowan |
| 2007/0049975 A1 | 3/2007 | Cates et al. |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jaeonson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0233216 A1 | 10/2007 | Liu et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2007/0299475 A1 | 12/2007 | Levin et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0082136 A1 | 4/2008 | Gaudiani |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269816 A1 | 10/2008 | Prakash et al. |
| 2008/0269823 A1 | 10/2008 | Burnes et al. |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288008 A1 | 11/2008 | Lee |
| 2008/0288039 A1 | 11/2008 | Reddy |
| 2008/0294208 A1 | 11/2008 | Willis et al. |
| 2008/0294210 A1 | 11/2008 | Rosero |
| 2008/0294229 A1 | 11/2008 | Friedman et al. |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0099619 A1 | 4/2009 | Lessmeier et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Jason |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0234412 A1 | 9/2009 | Sambelashvili |
| 2009/0234413 A1 | 9/2009 | Sambelashvili et al. |
| 2009/0234414 A1 | 9/2009 | Sambelashvili et al. |
| 2009/0234415 A1 | 9/2009 | Sambelashvili et al. |
| 2009/0248103 A1 | 10/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0016914 A1 | 1/2010 | Mullen et al. |
| 2010/0023078 A1 | 1/2010 | Dong et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0063375 A1 | 3/2010 | Kassab et al. |
| 2010/0063562 A1 | 3/2010 | Cowan et al. |
| 2010/0065871 A1 | 3/2010 | Govari et al. |
| 2010/0069983 A1 | 3/2010 | Peacock et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |

(56) References Cited

U.S. PATENT DOCUMENTS

| | | |
|---|---|---|
| 2010/0152798 A1 | 6/2010 | Sanghera et al. |
| 2010/0168761 A1 | 7/2010 | Kassab et al. |
| 2010/0168819 A1 | 7/2010 | Freeberg |
| 2010/0185250 A1 | 7/2010 | Rom |
| 2010/0198288 A1 | 8/2010 | Ostroff |
| 2010/0198291 A1 | 8/2010 | Sambelashvili et al. |
| 2010/0198304 A1 | 8/2010 | Wang |
| 2010/0217367 A1 | 8/2010 | Belson |
| 2010/0218147 A1 | 8/2010 | Ishikawa |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286541 A1 | 11/2010 | Musley et al. |
| 2010/0286626 A1 | 11/2010 | Petersen |
| 2010/0286744 A1 | 11/2010 | Echt et al. |
| 2010/0298841 A1 | 11/2010 | Prinzen et al. |
| 2010/0312309 A1 | 12/2010 | Harding |
| 2011/0022113 A1 | 1/2011 | Ideblick et al. |
| 2011/0071586 A1 | 3/2011 | Jacobson |
| 2011/0077708 A1 | 3/2011 | Ostroff |
| 2011/0106202 A1 | 5/2011 | Ding et al. |
| 2011/0112398 A1 | 5/2011 | Zarkh et al. |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0190841 A1 | 8/2011 | Sambelashvili et al. |
| 2011/0196444 A1 | 8/2011 | Prakash et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2011/0319956 A1 | 12/2011 | Zhu et al. |
| 2012/0004527 A1 | 1/2012 | Thompson et al. |
| 2012/0029323 A1 | 2/2012 | Zhao |
| 2012/0035685 A1 | 2/2012 | Saha et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0089214 A1 | 4/2012 | Kroll et al. |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101539 A1 | 4/2012 | Zhu et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109235 A1 | 5/2012 | Sheldon et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232478 A1 | 9/2012 | Haslinger |
| 2012/0232563 A1 | 9/2012 | Williams et al. |
| 2012/0232565 A1 | 9/2012 | Kveen et al. |
| 2012/0245665 A1 | 9/2012 | Friedman et al. |
| 2012/0263218 A1 | 10/2012 | Dal Molin et al. |
| 2012/0277600 A1 | 11/2012 | Greenhut |
| 2012/0277606 A1 | 11/2012 | Ellingson et al. |
| 2012/0277725 A1 | 11/2012 | Kassab et al. |
| 2012/0283587 A1 | 11/2012 | Gosh et al. |
| 2012/0283795 A1 | 11/2012 | Stancer et al. |
| 2012/0283807 A1 | 11/2012 | Deterre et al. |
| 2012/0284003 A1 | 11/2012 | Gosh et al. |
| 2012/0290025 A1 | 11/2012 | Keimel |
| 2012/0296228 A1 | 11/2012 | Zhang et al. |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0013017 A1 | 1/2013 | Mullen et al. |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053906 A1 | 2/2013 | Ghosh et al. |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0090701 A1 | 4/2013 | Liu et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourg et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116739 A1 | 5/2013 | Brada et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0131750 A1 | 5/2013 | Stadler et al. |
| 2013/0131751 A1 | 5/2013 | Stadler et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197599 A1 | 8/2013 | Sambelashvili et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Walfhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |

(56) References Cited

U.S. PATENT DOCUMENTS

| | | |
|---|---|---|
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268017 A1 | 10/2013 | Zhang et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0018892 A1 | 1/2014 | Dahlberg |
| 2014/0031836 A1 | 1/2014 | Ollivier |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0107724 A1 | 4/2014 | Shuros et al. |
| 2014/0114173 A1 | 4/2014 | Bar-Tal et al. |
| 2014/0114372 A1 | 4/2014 | Ghosh et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0277239 A1 | 9/2014 | Maskara et al. |
| 2014/0303704 A1 | 10/2014 | Suwito et al. |
| 2014/0309706 A1 | 10/2014 | Jacobson |
| 2014/0323882 A1 | 10/2014 | Ghosh et al. |
| 2014/0323892 A1 | 10/2014 | Ghosh et al. |
| 2014/0330208 A1 | 11/2014 | Christie et al. |
| 2014/0330287 A1 | 11/2014 | Thompson-Nauman et al. |
| 2014/0330326 A1 | 11/2014 | Thompson-Nauman et al. |
| 2014/0339570 A1 | 11/2014 | Carroll et al. |
| 2014/0358135 A1 | 12/2014 | Sambelashvili et al. |
| 2014/0371832 A1 | 12/2014 | Ghosh |
| 2014/0371833 A1 | 12/2014 | Ghosh et al. |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0045811 A1 | 2/2015 | Schilling |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Foster et al. |
| 2015/0105836 A1 | 4/2015 | Bonner et al. |
| 2015/0142070 A1 | 5/2015 | Sambelashvili |
| 2015/0148697 A1 | 5/2015 | Burnes et al. |
| 2015/0149096 A1 | 5/2015 | Soykan |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217110 A1 | 8/2015 | Ollivier |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0305695 A1 | 10/2015 | Lahm et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2015/0335894 A1 | 11/2015 | Bornzin et al. |
| 2016/0015287 A1 | 1/2016 | Anderson et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0045738 A1 | 2/2016 | Ghosh et al. |
| 2016/0051821 A1 | 2/2016 | Sambelashvili et al. |
| 2016/0059002 A1 | 3/2016 | Grubac et al. |
| 2016/0067486 A1 | 3/2016 | Brown et al. |
| 2016/0067487 A1 | 3/2016 | Demmer et al. |
| 2016/0067490 A1 | 3/2016 | Carney et al. |
| 2016/0114161 A1 | 4/2016 | Amblard et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0129239 A1 | 5/2016 | Anderson |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0310733 A1 | 10/2016 | Sheldon et al. |
| 2016/0317825 A1 | 11/2016 | Jacobson |
| 2016/0339248 A1 | 11/2016 | Schrock et al. |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Shanna et al. |
| 2017/0043174 A1 | 2/2017 | Greenhut et al. |
| 2017/0056670 A1 | 3/2017 | Sheldon et al. |
| 2017/0182327 A1 | 6/2017 | Liu |
| 2017/0189681 A1 | 7/2017 | Anderson |

(56) References Cited

U.S. PATENT DOCUMENTS

| | | |
|---|---|---|
| 2017/0209689 A1 | 7/2017 | Chen |
| 2017/0216575 A1 | 8/2017 | Asleson et al. |
| 2017/0304624 A1 | 10/2017 | Friedman et al. |
| 2017/0326369 A1 | 11/2017 | Koop et al. |
| 2017/0340885 A1 | 11/2017 | Sambelashvili |
| 2017/0340887 A1 | 11/2017 | Engels et al. |
| 2018/0008829 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |
| 2018/0050208 A1 | 2/2018 | Shuros et al. |
| 2018/0078773 A1 | 3/2018 | Thakur et al. |
| 2018/0078779 A1 | 3/2018 | An et al. |
| 2018/0117324 A1 | 5/2018 | Schilling et al. |
| 2018/0140848 A1 | 5/2018 | Stahmann |
| 2018/0178007 A1 | 6/2018 | Shuros et al. |
| 2018/0212451 A1 | 7/2018 | Schmidt et al. |
| 2018/0256904 A1 | 9/2018 | Li et al. |
| 2018/0264262 A1 | 9/2018 | Haasl et al. |
| 2018/0264272 A1 | 9/2018 | Haasl et al. |
| 2018/0264273 A1 | 9/2018 | Haasl et al. |
| 2018/0264274 A1 | 9/2018 | Haasl et al. |
| 2018/0280686 A1 | 10/2018 | Shuros et al. |
| 2018/0326215 A1 | 11/2018 | Ghosh |
| 2019/0022378 A1 | 1/2019 | Prillinger et al. |
| 2019/0030346 A1 | 1/2019 | Li |
| 2019/0038906 A1 | 2/2019 | Koop et al. |
| 2019/0083779 A1 | 3/2019 | Yang et al. |
| 2019/0083800 A1 | 3/2019 | Yang et al. |
| 2019/0083801 A1 | 3/2019 | Yang et al. |
| 2019/0111264 A1 | 4/2019 | Zhou |
| 2019/0111265 A1 | 4/2019 | Zhou |
| 2019/0111270 A1 | 4/2019 | Zhou |
| 2019/0126040 A1 | 5/2019 | Shuros et al. |
| 2019/0126049 A1 | 5/2019 | Casavant et al. |
| 2019/0126050 A1 | 5/2019 | Shuros et al. |
| 2019/0134404 A1 | 5/2019 | Sheldon et al. |
| 2019/0134405 A1 | 5/2019 | Sheldon et al. |
| 2019/0192092 A1 | 6/2019 | Hahn et al. |
| 2019/0192860 A1 | 6/2019 | Ghosh et al. |
| 2019/0201698 A1 | 7/2019 | Herrmann et al. |
| 2019/0217097 A1 | 7/2019 | Thakur et al. |
| 2019/0269926 A1 | 9/2019 | Ghosh |
| 2019/0275329 A1 | 9/2019 | Brisben et al. |
| 2021/0085986 A1 | 3/2021 | Li et al. |

FOREIGN PATENT DOCUMENTS

| | | |
|---|---|---|
| AU | 2014203793 A1 | 7/2014 |
| CN | 202933393 | 5/2013 |
| EP | 0362611 A1 | 4/1990 |
| EP | 0459 239 A2 | 12/1991 |
| EP | 0 728 497 A2 | 8/1996 |
| EP | 1234597 A2 | 8/2002 |
| EP | 1 541 191 A1 | 6/2005 |
| EP | 1 702 648 A1 | 9/2006 |
| EP | 1 904 166 B1 | 6/2011 |
| EP | 2 452 721 A1 | 5/2012 |
| EP | 2 471 452 A1 | 7/2012 |
| EP | 2 662 113 A2 | 11/2013 |
| EP | 1 703 944 B1 | 7/2015 |
| JP | 2005245215 | 9/2005 |
| WO | WO 95/00202 | 1/1995 |
| WO | WO 96/36134 | 11/1996 |
| WO | WO 97/24981 | 7/1997 |
| WO | WO 02/22206 A1 | 3/2002 |
| WO | WO 03/092800 A1 | 11/2003 |
| WO | WO 2005/000206 A2 | 1/2005 |
| WO | WO 2005/042089 A1 | 5/2005 |
| WO | WO 2006/069215 A2 | 6/2006 |
| WO | WO 2006/086435 A2 | 8/2006 |
| WO | WO 2006/113659 A1 | 10/2006 |
| WO | WO 2007/073435 A1 | 6/2007 |
| WO | WO 2007/075974 A2 | 7/2007 |
| WO | WO 2009/006531 A1 | 1/2009 |
| WO | WO 2010/071849 A2 | 6/2010 |
| WO | WO 2013/080038 A2 | 6/2013 |
| WO | WO 2013/098644 A2 | 7/2013 |
| WO | WO 2014/055692 A2 | 4/2014 |
| WO | WO 2015/081221 A1 | 6/2015 |
| WO | WO 2016/011042 A1 | 1/2016 |
| WO | WO 2016/077099 A1 | 5/2016 |
| WO | WO 2016/110856 A1 | 7/2016 |
| WO | WO 2016/171891 A1 | 10/2016 |
| WO | WO 2017/075193 A1 | 5/2017 |
| WO | 2017/192892 | 11/2017 |
| WO | WO 2018/009569 A1 | 1/2018 |
| WO | WO 2018/017226 A1 | 1/2018 |
| WO | WO 2018/017361 A1 | 1/2018 |
| WO | WO 2018/035343 A1 | 2/2018 |
| WO | WO 2018/081519 A1 | 5/2018 |

OTHER PUBLICATIONS

Http://www.isrctn.com/ISRCTN47824547, public posting published Aug. 2019.

Abed et al., "Obesity results in progressive atrial structural and electrical remodeling: Implications for atrial fibrillation," *Heart Rhythm Society*, Jan. 2013; 10(1):90-100.

Adragão et al., "Ablation of pulmonary vein foci for the treatment of atrial fibrillation; percutaneous electroanatomical guided approach," *Europace*, Oct. 2002; 4(4):391-9.

Allot et al., "Arrhythmia detection by dual-chamber implantable cardioverter defibrillators: A review of current algorithms," *Europace*, Jul. 2004; 6(4):273-86.

Amirahmadi et al., "Ventricular Tachycardia Caused by Mesothelial Cyst," *Indian Pacing and Electrophysiology Journal*, 2013; 13(1):43-44.

Ammirabile et al., "Pitx2 confers left morphological, molecular, and functional identity to the sinus venosus myocardium," *Cardiovasc Res.*, Feb. 2012; 93(2):291-301.

Anfmsen, "Non-pharmacological Treatment of Atrial Fibrillation," *Indian Pacing and Electrophysiology Journal*, Jan. 2002, 2(1):4-14.

Anné et al., "Ablation of post-surgical intra-atrial reentrant Tachycardia," *European Heart Journal*, 2002; 23:169-1616.

Arenal et al., "Dominant frequency differences in atrial fibrillation patients with and without left ventricular systolic dysfunction," *Europace*, Apr. 2009; 11(4):450-457.

Arriagada et al., "Predictors of arrhythmia recurrence in patients with lone atrial fibrillation," *Europace*, Jan. 2008; 10(1):9-14.

Asirvatham et al., "Cardiac Anatomic Considerations in Pediatric Electrophysiology," *Indian Pacing and Electrophysiology Journal*, Apr. 2008; 8(Suppl 1):S75-S91.

Asirvatham et al., "Intramyocardial Pacing and Sensing for the Enhancement of Cardiac Stimulation and Sensing Specificity," *Pacing Clin. Electrophysil.L*, Jun. 2007; 30(6):748-754.

Asirvatham et al., "Letter to the Editor," *J Cardiovasc Electrophysiol.*, Mar. 2010; 21(3): E77.

Balmer et al., "Long-term follow7 up of children with congenital complete atrioventricular block and the impact of pacemaker therapy," *Europace*, Oct. 2002; 4(4):345-349.

Barold et al., "Conventional and biventricular pacing in patients with first-degree atrioventricular block," *Europace*, Oct. 2012; 14(10):1414-9.

Barold et al., "The effect of hyperkalaemia on cardiac rhythm devices," *Europace*, Apr. 2014; 16(4):467-76.

Bayrak et al., "Added value of transoesophageal echocardiography during transseptal puncture performed by inexperienced operators," *Europace*, May 2012; 14(5):661-5.

Bergau et al., "Measurement of Left Atrial Pressure is a Good Predictor of Freedom From Atrial Fibrillation," *Indian Pacing and Electrophysiology Journal*, Jul. 2014; 14(4):181-93.

Bernstein et al., "The revised NASPE/BPEG generic code for antibradycardia, adaptive-rate, and multisite pacing. North American Society of Pacing and Electrophysiology/British Pacing and Electrophysiology Group," *Pacing Clin Electrophysiol.*, Feb. 2002; 25(2):260-4.

(56) References Cited

OTHER PUBLICATIONS

Bito et al., "Early exercise training after myocardial infarction prevents contractile but not electrical remodeling or hypertrophy," *Cardiovascular Research*, Apr. 2010; 86(1):72-81.
Bollmann et al., "Analysis of surface electrocardiograms in atrial fibrillation: techniques, research, and clinical applications," *Europace*, Nov. 2006; 8(11):911-926.
Bortone et al., "Evidence for an incomplete mitral isthmus block after failed ablation of a left postero-inferior concealed accessory pathway," *Europace*, Jun. 2006; 8(6):434-7.
Boulos et al., "Electroanatomical mapping and radiofrequency ablation of an accessory pathway associated with a large aneurysm of the coronary sinus," *Europace*, Nov. 2004; 6(6):608-12.
Brembilla-Perrot et al., "Incidence and prognostic significance of spontaneous and inducible antidromic tachycardia," *Europace*, Jun. 2013; 15(6):871-876.
Buber et al., "Morphological features of the P-waves at surface electrocardiogram as surrogate to mechanical function of the left atrium following a successful modified maze procedure," *Europace*, Apr. 2014; 16(4):578-86.
Burashnikov et al., "Late-phase 3 EAD. A unique mechanism contributing to initiation of atrial fibrillation," *Pacing Clin Electrophysiol.*, Mar. 2006, 29(3):290-5.
Burashnikov et al., "Atrial-selective inhibition of sodium-channel current by Wenxin Keii is effective in suppressing atrial fibrillation," *Heart Rhythm*, Jan. 2012; 9(1):125-31.
Calvo et al., "Efficacy of circumferential pulmonary vein ablation of atrial fibrillation in endurance athletes," *Europace*, Jan. 2010; 12(1):30-6.
Can et al., ""Atrial torsades de pointes" Induced by Low-Energy Shock From Implantable-Cardioverter Defibrillator," *Indian Pacing and Electrophysiology Journal*, Sep. 2013, 13(5):194-199.
Carroz et al., "Pseudo-pacemaker syndrome in a young woman with first-degree atrio-ventricular block," *Europace*, Apr. 2010; 12(4):594-596.
Catanchin et al., "Wolff-Parkinson-White syndrome with an unroofed coronary sinus without persistent left superior vena cava treated with catheter cryoablation," *Indian Pacing and Electrophysiology Journal*, Aug. 2008; 8(3):227-233.
Cazeau et al., "Cardiac resynchronization therapy," *Europace*, Sep. 2004; 5 Suppl 1:S42-8.
Chandra et al., "Evaluation of KCB-328, a new IKr blocking anti arrhythmic agent in pacing induced canine atrial fibrillation," *Europace*, Sep. 2004; 6(5):384-91.
Chang et al., "Electrophysiological characteristics and catheter ablation in patients with paroxysmal supraventricular tachycardia and paroxysmal atrial fibrillation," *J Cardiovasc Electrophysiol.*, Apr. 2008; 19(4):367-73.
Charron et al., "A familial form of conduction defect related to a mutation in the PRKAG2 gene," *Europace*, Aug. 2007; 9(8):597-600.
Chou et al., "Effects of SEA0400 on Arrhythmogenicity in a Langendorff-Perfused 1-Month Myocardial Infarction Rabbit Model," *Pacing Clin Electrcphysiol.*, May 2013; 36(5):596-606.
Ciploetta et al., "Posterior Coronary Vein as the Substrate for an Epicardial Accessory Pathway," *Indian Pacing and Electrophysiology Journal*, Aug. 2013, 13(4):142-7.
Climent et al., "Effects of endocardial microwave energy ablation," *Indian Pacing and Electrophysiology Journal*, Jul. 2005, 5(3):233-43.
Comtois et al., "Of circles and spirals: bridging the gap between the leading circle and spiral wave concepts of cardiac reentry," *Europace*, Sep. 2005; 7 Suppl 2:10-20.
Crick et al., "Anatomy of the pig heart: comparisons with normal human cardiac structure," *J. Anat.*, 1998, 193:105-119.
Daoulah et al., "Unintended Harm and Benefit of the Implantable Defibrillator in an Unfortunate 19-Year-Old Male: Featuring a Sequence of Rare Life-threatening Complications of Cardiac Procedures," *Indian Pacing and Electrophysiology Journal*, Aug. 2013; 13(4):151-6.
De Mattia et al., "Paroxysmal atrial fibrillation triggered by a monomorphic ventricular couplet in a patient with acute coronary' syndrome," *Indian Pacing and Electrophysiology Journal*, Jan. 2012; 12(1):19-23.
DeSimone et al., "New approach to cardiac resynchronization therapy: CRT without left ventricular lead," Apr. 25, 2014, 2 pages.
De Sisti et al., "Electrophysiological determinants of atrial fibrillation in sinus node dysfunction despite atrial pacing," *Europace*, Oct. 2000; 2(4):304-11.
De Voogt et al., "Electrical characteristics of low atrial septum pacing compared with right atrial appendage pacing," *Europace*, Jan. 2005; 7(1):60-6.
De Voogt et al., "A technique of lead insertion for low atrial septal pacing," *Pacing Clin Electrophysiol.*, Jul. 2005; 28(7):639-46.
Dizon et al. "Real-time stroke volume measurements for the optimization of cardiac resynchronization therapy parameters," *Europace*, Sep. 2010; 12(9):1270-1274.
Duckett et al., "Relationship between endocardial activation sequences defined by high-density mapping to early septal contraction (septal flash) in patients with left bundle branch block undergoing cardiac resynchronization therapy," *Europace*, Jan. 2012, 14(1):99-106.
Eksik et al., "Influence of atrioventricular nodal reentrant tachycardia ablation on right to left inter-atrial conduction," *Indian Pacing and Electrophysiology Journal*, Oct. 2005; 5(4):279-88.
Fiala et al., "Left Atrial Voltage during Atrial Fibrillation in Paroxysmal and Persistent Atrial Fibrillation Patients," *PACE*, May 2010; 33(5):541-548.
Fragakis et al., "Acute beta-adrenoceptor blockade improves efficacy of ibutilide in conversion of atrial fibrillation with a rapid ventricular rate," *Europace*, Jan. 2009; 11(1):70-4.
Frogoudaki et al., "Pacing for adult patients with left atrial isomerism: efficacy and technical considerations," *Europace*, Apr. 2003, 5(2):189-193.
Ganapathy et al., "Implantable Device to Monitor Cardiac Activity with Sternal Wires," *Pacing Clin. Electrophysiol.*, Dec. 2014; Epub Aug. 24, 2014; 37(12):1630-40.
Geddes, "Accuracy limitations of chronaxie values," *IEEE Trans Biomed Eng.*, Jan. 2004; 51(1):176-81.
Gertz et al., "The impact of mitral regurgitation on patients undergoing catheter ablation of atrial fibrillation," *Europace*, Aug. 2011, 13(8):1127-32.
Girmatsion et al., "Changes in microRNA-1 expression and IKI up-regulation in human atrial fibrillation," *Heart Rhythm*, Dec. 2009; 6(12):1802-9.
Goette et al., "Acute atrial tachyarrhythmia induces angiotensin II type 1 receptor-mediated oxidative stress and microvascular flow abnormalities in the ventricles," *European Heart Journal*, Jun. 2009; 30(11):1411-20.
Goette et al., "Electrophysiological effects of angiotensin II. Part I: signal transduction and basic electrophysiological mechanisms," *Europace*, Feb. 2008; 10(2):238-41.
Gómez et al., "Nitric oxide inhibits Kv4.3 and human cardiac transient outward potassium current (Ito1)," *Cardiovasc Res.*, Dec. 2008; 80(3):375-84.
Gros et al., "Connexin 30 is expressed in the mouse sino-atrial node and modulates heart rate," *Cardiovascular Research*, Jan. 2010, 85(1):45-55.
Guenther et al., "Substernal Lead Implantation: A Novel Option to Manage OFT Failure in S-ICD patients," *Clinical Research Cardiology*, Feb. 2015; Epub Oct. 2, 2014; 104(2):189-91.
Guillem et al., "Noninvasive mapping of human atrial fibrillation," *J Cardiovasc Electrophysiol.*, May 2009, 20(5):507-513.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Hakacova et al., "Septal atrial pacing for the prevention of atrial fibrillation," Europace, 2007, 9:1124-1128.
Hasan et al., "Safety, efficacy, and performance of implanted recycled cardiac rhythm management (CRM) devices in underprivileged patients," *Pacing Clin Electrophysiol.*, Jun. 2011; 34(6):653-8.

(56) References Cited

OTHER PUBLICATIONS

Hawkins, "Epicardial Wireless Pacemaker for Improved Left Ventricular Reynchronization (Conceptual Design)", Dec. 2010, A Thesis presented to the Faculty of California Polytechnic State University, San Luis Obispo, 57 pp.

He et al., "Three-dimensional cardiac electrical imaging from intracavity recordings," *IEEE Trans Biomed Eng.*, Aug. 2007; 54(8):1454-60.

Heist et al., "Direct visualization of epicardial structures and ablation utilizing a visually guided laser balloon catheter: preliminary findings," *J Cardiovasc Electrophysiol.*, Jul. 2011; 22(7):808-12.

Henz et al., "Synchronous Ventricular Pacing without Crossing the Tricuspid Valve or Entering the Coronary Sinus—Preliminary Results," *J Cardiovasc Electrophysiol.*, Dec. 2009; 20(12):1391-1397.

Hiippala et al., "Automatic Atrial Threshold Measurement and Adjustment in Pediatric Patients," *Placing Clin Electrophysiol.*, Mar. 2010; 33(3):309-13.

Ho, "Letter to the Editor" *J Cardiovasc Electrophysiol.*, Mar. 2010, 21(3): E76.

Höijer et al., "Improved cardiac function and quality of life following upgrade to dual chamber pacing after long-term ventricular stimulation," *European Heart Journal*, Mar. 2002; 23(6):490-497.

Huang et al., "A Novel Pacing Strategy With Low and Stable Output: Pacing the Left Bundle Branch Immediately Beyond the Conduction Block," *Can J Cardiol.*, Dec. 2007; Epub Sep. 22, 2017; 33(12):1736.e1-1736.e.

Inter-Office Memo, Model 6426-85 Canine Feasibility AV Septal 8 mm Screw-In Right Single Pass DDD Lead Final Report (AR # 0120A0207).

Ishigaki et al., "Prevention of immediate recurrence of atrial fibrillation with low-dose landiolol after radiofrequency catheter ablation," *Journal of Arrhythmia*, Oct. 2015; 31(5):279-285.

Israel, "The role of pacing mode in the development of atrial fibrillation," *Europace*, Feb. 2006; 8(2):89-95.

Janion et al., "Dispersion of P wave duration and P wave vector in patients with atrial septal aneurysm," *Europace*, Jul. 2007; 9(7):471-4.

Kabra et al., "Recent Trends in Imaging for Atrial Fibrillation Ablation," *Indian Pacing and Electrophysiology Journal*, 2010; 10(5):215-227.

Kalbfleisch et al., "Catheter Ablation with Radiofrequency Energy: Biophysical Aspects and Clinical Applications," *Journal of Cardiovascular Electrophysiology*, Oct. 2008; 3(2):173-186.

Katritsis et al., "Classification and differential diagnosis of atrioventricular nodal re-entrant tachycardia," *Europace*, Jan. 2006; 8(1):29-36.

Katritsis et al., "Anatomically left-sided septal slow pathway ablation in dextrocardia and situs inversus totalis," *Europace*, Aug. 2008; 10(8):1004-5.

Khairy et al., "Cardiac Arrhythmias In Congenital Heart Diseases," *Indian Pacing and Electrophysiology Journal*, Nov.-Dec. 2009; 9(6):299-317.

Kimmel et al., "Single-site ventricular and biventricular pacing: investigation of latest depolarization strategy," *Europace*, Dec. 2007; 9(12):1163-1170.

Knackstedt et al., "Electro-anatomic mapping systems in arrhythmias," *Europace*, Nov. 2008, 10 Suppl 3:iii28-iii34.

Kobayashi et al., "Successful Ablation of Antero-septal Accessory Pathway in the Non-Coronary Cusp in a Child," *Indian Pacing and Electrophysiology Journal*, 2012; 12(3):124-130.

Kojodjojo et al., "4:2:1 conduction of an AF initiating trigger," *Indian Pacing and Electrophysiology Journal*, Nov. 2015; 15(5):255-8.

Kołodzińska et al., "Differences in encapsulating lead tissue in patients who underwent transvenous lead removal," *Europace*, Jul. 2012; 14(7):994-1001.

Konecny et al., "Synchronous intra-myocardial ventricular pacing without crossing the tricuspid valve or entering the coronary sinus," *Cardiovascular Revascularization Medicine*, 2013, 14:137-138.

Kriatselis et al., "Ectopic atrial tachycardias with early activation at His site: radiofrequency ablation through a retrograde approach," *Europace*, Jun. 2008; 10(6):698-704.

Lalu et al., "Ischaemia-reperfusion injury activates matrix metalloproteinases in the human heart," *Eur Heart J.*, Jan. 2005, 26(1):27-35.

Laske et al., "Excitation of the Intrinsic Conduction System Through His and Interventricular Septal Pacing," *Pacing Clin. Electrophysiol.*, Apr. 2006; 29(4):397-405.

Leclercq, "Problems and troubleshooting in regular follow-up of patients with cardiac resynchronization therapy," *Europace*, Nov. 2009; 11 Suppl 5:v66-71.

Lee et al., "An unusual atrial tachycardia in a patient with Friedreich ataxia," *Europace*, Nov. 2011, 13(11):1660-1.

Lee et al., "Blunted Proarrhythmic Effect of Nicorandil in a Langendorff-Perfused Phase-2 Myocardial Infarction Rabbit Model," *Pacing Clin Electrophysiol.*, Feb. 2013; 36(2):142-51.

Lemay et al., "Spatial dynamics of atrial activity assessed by the vectorcardiogram: from sinus rhythm to atrial fibrillation," *Europace*, Nov. 2007; 9 Suppl 6:vi109-18.

Levy et al., "Does the mechanism of action of biatrial pacing for atrial fibrillation involve changes in cardiac haemodynamics? Assessment by Doppler echocardiography and natriuretic peptide measurements," *Europace*, Apr. 2000; 2(2):127-35.

Lewalter et al., "Comparison of spontaneous atrial fibrillation electrogram potentials to the P wave electrogram amplitude in dual chamber pacing with unipolar atrial sensing," *Europace*, Apr. 2000, 2(2):136-40.

Liakopoulos et al., "Sequential deformation and physiological considerations in unipolar right and left ventricular pacing," *European Journal of Cardio-thoracic Surgery*, Apr. 1, 2006; 29S1:S188-197.

Lian et al., "Computer modeling of ventricular rhythm during atrial fibrillation and ventricular pacing," *IEEE Transactions on Biomedical Engineering*, Aug. 2006; 53(8):1512-1520.

Lim et al., "Right ventricular lead implantation facilitated by a guiding sheath in a patient with severe chamber dilatation with tricuspid regurgitation," *Indian Pacing and Electrophysiology Journal*, Sep. 2011; 11(5):156-8.

Lim et al., "Coupled pacing improves left ventricular function during simulated atrial fibrillation without mechanical dyssynchrony," *Europace*, Mar. 2010; 12(3):430-6.

Lou et al., "Tachy-brady arrhythmias: The critical role of adenosine-induced sinoatrial conduction block in post-tachycardia pauses," *Heart Rhythm.*, Jan. 2013, 10(1):110-8.

Lutomsky et al., "Catheter ablation of paroxysmal atrial fibrillation improves cardiac function: a prospective study on the impact of atrial fibrillation ablation on left ventricular function assessed by magnetic resonance imaging," *Europace*, May 2008; 10(5):593-9.

Macedo et al., "Septal accessory pathway: anatomy, causes for difficulty, and an approach to ablation," *Indian Pacing and Electrophysiology Journal*, Jul. 2010; 10(7):292-309.

Mafi-Rad et al., "Feasibility and Acute Hemodynamic Effect of Left Ventricular Septal Pacing by Transvenous Approach Through the Interventricular Septum," *Circ Arrhythm Electrophysoil.*, Mar. 2016; 9(3):e003344.

Mani et al., "Dual Atrioventricular Nodal Pathways Physiology: A Review of Relevant Anatomy, Electrophysiology, and Electrocardiographic Manifestations," *Indian Pacing and Electrophysiology Journal*, Jan. 2014; 14(1):12-25.

Manios et al., "Effects of successful cardioversion of persistent atrial fibrillation on right ventricular refractoriness and repolarization," *Europace*, Jan. 2005; 7(1):34-9.

Manolis et al., "Prevention of atrial fibrillation by inter-atrial septum pacing guided by electrophysiological testing, in patients with delayed interatrial conduction," *Europace*, Apr. 2002; 4(2):165-174.

Marino et al., "Inappropriate mode switching clarified by using a chest radiograph," *Journal of Arrhythmia*, Aug. 2015; 31(4):246-248.

Markowitz et al., "Time course and predictors of autonomic dysfunction after ablation of the slow atrioventricular nodal pathway," *Pacing Clin Electrophysiol.*, Dec. 2004; 27(12):1638-43.

Marshall et al., "The effects of temperature on cardiac pacing thresholds," *Pacing Clin Electrophysiol.*, Jul. 2010, 33(7):826-833.

(56) References Cited

OTHER PUBLICATIONS

McSharry et al., "A Dynamical Model for Generating Synthetic Electrocardiogram Signals," *IEEE Transactions on Biomedical Engineering*, Mar. 2003, 50(3):289-294.

Meijler et al., "Scaling of Atrioventricular Transmission in Mammalian Species: An Evolutionary Riddle!," *Journal of Cfardiovascular Electrophysiology*, Aug. 2002; 13(8):826-830.

Meiltz et al., "Permanent form of junctional reciprocating tachycardia in adults: peculiar features and results of radiofrequency catheter ablation," *Europace*, Jan. 2006, 8(1):21-8.

Mellin et al., "Transient reduction in myocardial free oxygen radical levels is involved in the improved cardiac function and structure after long-term allopurinol treatment initiated in established chronic heart failure," *Eur Heart J.*, Aug. 2005; 26(15):1544-50.

Mestan et al., "The influence of fluid and diuretic administration on the index of atrial contribution in sequentially paced patients," *Europace*, Apr. 2006; 8(4):273-8.

Metin et al., "Assessment of the P Wave Dispersion and Duration in Elite Women Basketball Players," *Indian Pacing and Electrophysiology Journal*, 2010, 10(1):11-20.

Mills et al., "Left Ventricular Septal and Left Ventricular Apical Pacing Chronically Maintain Cardiac Contractile Coordination, Pump Function and Efficiency," *Circ Arrhythm Electrophysoil.*, Oct. 2009; 2(5):571-579.

Mitchell et al., "How do atrial pacing algorithms prevent atrial arrhythmias?" *Europace*, Jul. 2004, 6(4):351-62.

Mirzoyev et al., "Embryology' of the Conduction System for the Electrophysiologist," *Indian Pacing and Electrophysiology Journal*, 2010; 10(8):329-338.

Modre et al., "Noninvasive Myocardial Activation Time Imaging: A Novel Inverse Algorithm Applied to Clinical ECG Mapping Data," *IEE Transactions on Biomedical Engineering*, Oct. 2002; 49(10):1153-1161.

Montgomery et al., "Measurement of diffuse ventricular fibrosis with myocardial T1 in patients with atrial fibrillation," *J Arrhythm.*, Feb. 2016; 32(1):51-6.

Mulpuru et al., "Synchronous ventricular pacing with direct capture of the atrioventricular conduction system: Functional anatomy, terminology, and challenges," *Heart Rhythm*, Nov. 2016, Epub Aug. 3, 2016, 13(11):2237-2246.

Musa et al., "Inhibition of Platelet-Derived Growth Factor-AB Signaling Prevents Electromechanical Remodeling of Adult Atrial Myocytes that Contact Myofibroblasts," *Heart Rhythm*, Jul. 2013; 10(7):1044-1051.

Nagy et al., "Wnt-11 signalling controls ventricular myocardium development by patterning N-cadherin and β-catenin expression," *Cardiovascular Research*, Jan. 2010; 85(1):100-9.

Namboodiri et al., "Electrophysiological features of atrial flutter in cardiac sarcoidosis: a report of two cases," *Indian Pacing and Electrophysiology Journal*, Nov. 2012, 12(6):284-9.

Nanthakumar et al., "Assessment of accessory pathway and atrial refractoriness by transesophageal and intracardiac atrial stimulation: An analysis of methodological agreement," *Europace*, Jan. 1999; 1(1):55-62.

Neto et al., "Temporary atrial pacing in the prevention of postoperative atrial fibrillation," *Pacing Clin Electrophysiol.*, Jan. 2007; 30(Suppl 1):S79-83.

Nishijima et al., "Tetrahydrobiopterin depletion and NOS2 uncoupling contribute to heart failure-induced alterations in atrial electrophysiology," *Cardiovasc Res.*, Jul. 2011, 91(1):71-9.

Niwano et al., "Effect of oral L-type calcium channel blocker on repetitive paroxysmal atrial fibrillation: spectral analysis of fibrillation waves in the Holter monitoring," *Europace*, Dec. 2007; 9(12):1209-1215.

Okumura et al., "Effects of a high-fat diet on the electrical properties of porcine atria," *Journal of Arrhythmia*, Dec. 2015; 31(6):352-358.

Olesen et al., "Mutations in sodium channel β-subunit SCN3B are associated with early-onset lone atrial fi brillation," *Cardiovascular Research*, Mar. 2011; 89(4):786-93.

Ozmen et al., "P wave dispersion is increased in pulmonary stenosis," *Indian Pacing and Electrophysiology Journal*, Jan. 2006; 6(1):25-30.

Packer et al., "New generation of electro-anatomic mapping: Full intracardiac image integration," *Europace*, Nov. 2008, 10 Suppl 3:iii35-41.

Page et al., "Ischemic ventricular tachycardia presenting as a narrow' complex tachycardia," *Indian Pacing and Electrophysiology Journal*, Jul. 2014, 14(4):203-210.

Pakarinen et al., "Pre-implant determinants of adequate long-term function of single lead VDD pacemakers," *Europace*, Apr. 2002; 4:137-141.

Patel et al., "Atrial Fibrillation after Cardiac Surgery: Where are we now?" *Indian Pacing and Electrophysiology Journal*, Oct.-Dec. 2008; 8(4):281-291.

Patel et al., "Successful ablation of a left-sided accessory7 pathway in a patient with coronary sinus atresia and arteriovenous fistula: clinical and developmental insights," *Indian Pacing and Electrophysiology Journal*, Mar. 2011; 11(2):43-49.

Peschar et al., "Left Ventricular Septal and Apex Pacing for Optimal Pump Function in Canine Hearts," *J Am Coll Cardiol*, Apr. 2, 2003; 41(7):1218-1226.

Physiological Research Laboratories, Final Report for an Acute Study for Model 6426-85 AV Septal Leads, Feb. 1996.

Porciani et al., "Interatrial septum pacing avoids the adverse effect of interatrial delay in biventricular pacing: an echo-Doppler evaluation," *Europace*, Jul. 2002; 4(3):317-324.

Potse et ah, "A Comparison of Monodomain and Bidomain Reaction-Diffusion Models for Action Potential Propagation in the Human Heart," *IEEE Transactions on Biomedical Engineering*, Dec. 2006; 53(12 Pt 1):2425-35.

Prystowsky et al., "Case studies with the experts: management decisions in atrial fibrillation," *J Cardiovasc Electrophysiol.*, Feb. 2008; 19(Suppl. 1):S1-12.

Prystowsky, "The history of atrial fibrillation: the last 100 years," *J Cardiovasc Electrophysiol*, Jun. 2008; 19(6):575-582.

Pytkowski et al., "Paroxysmal atrial fibrillation is associated with increased intra-atrial conduction delay," *Europac*, Dec. 2008; 10(12):1415-20.

Qu et al., "Dynamics and cardiac arrhythmias," *J Cardiovasc Electrophysiol.*, Sep. 2006; 17(9):1042-9.

Ravens et al., "Role of potassium currents in cardiac arrhythmias," *Europace*, Oct. 2008; 10(10):1133-7.

Ricci et al., Efficacy of a dual chamber defibrillator with atrial anti tachy cardia functions in treating spontaneous atrial tachyarrhythmias in patients with lifethreatening ventricular tachyarrhythmias, *European Heart Journal*, Sep. 2002; 23(18):1471-9.

Roberts-Thomson et al., "Focal atrial tachycardia II: management," *Pacing Clin Electrophysiol.*, Jul. 2006; 29(7):769-78.

Rossi et al., "Endocardial vagal atrioventricular node stimulation in humans: reproducibility on 18-month follow-up," *Europace*, Dec. 2010; 12(12):1719-24.

Rouzet et al., "Contraction delay of the RV outflow tract in patients with Brugada syndrome is dependent on the spontaneous ST-segment elevation pattern," *Heart Rhythm*, Dec. 2011, 8(12):1905-12.

Russo et al., "Atrial Fibrillation and Beta Thalassemia Major: The Predictive Role of the 12-lead Electrocardiogram Analysis," *Indian Pacing and Electrophysiology Journal*, May 2014; 14(3):121-32.

Ryu et al., "Simultaneous Electrical and Mechanical Mapping Using 3D Cardiac Mapping System: Novel Approach for Optimal Cardiac Resynchronization Therapy," Journal of Cardiovascular Electrophysiology, Feb. 2010, 21(2): 219-22.

Sairaku et al., "Prediction of sinus node dysfunction in patients with persistent atrial flutter using the flutter cycle length," *Europace*, Mar. 2012, 14(3):380-7.

Santini et al., "Immediate and long-term atrial sensing stability in single-lead VDD pacing depends on right atrial dimensions," *Europace*, Oct. 2001, 3(4):324-31.

Saremi et al., "Cardiac Conduction System: Delineation of Anatomic Landmarks With Multi detector CT," *Indian Pacing and Electrophysiology Journal*, Nov. 2009; 9(6):318-33.

(56) References Cited

OTHER PUBLICATIONS

Savelieva et al., "Anti-arrhythmic drug therapy for atrial fibrillation: current anti-arrhythmic drugs, investigational agents, and innovative approaches," *Europace*, Jun. 2008; 10(6):647-665.

Schmidt et al., "Navigated DENSE strain imaging for post-radiofrequency ablation lesion assessment in the swine left atria," *Europace*, Jan. 2014; 16(1):133-41.

Schoonderwoerd et al., "Rapid Pacing Results in Changes in Atrial but not in Ventricular Refractoriness," *Pacing Clin Electrophysiol.*, Mar. 2002; 25(3):287-90.

Schoonderwoerd et al., "Atrial natriuretic peptides during experimental atrial tachycardia: role of developing tachycardiomyopathy," *J Cardiovasc Electrophysiol.*, Aug. 2004; 15(8):927-32.

Schoonderwoerd et al., "Atrial ultrastructural changes during experimental atrial tachycardia depend on high ventricular rate," *J Cardiovasc Electrophysiol.*, Oct. 2004; 15(10):1167-74.

Sedmera, "Function and form in the developing cardiovascular system," *Cardiovasc Res.*, Jul. 2011; 91(2):252-9.

Severi et al., "Alterations of atrial electrophysiology induced by electrolyte variations: combined computational and P-wave analysis," *Europace*, Jun. 2010; 12(6):842-9.

Seyedi et al., "A Survey on Intrabody Communications for Body Area Network Application," IEEE Transactions on Biomedical Engineering, vol. 60(8): 2067-2079, 2013.

Shah et al., "Stable atrial sensing on long-term follow up of VDD pacemakers," *Indian Pacing and Electrophysiology Journal*, Oct. 2006; 6(4): 189-93.

Shenthar et al., "Pennanent pacemaker implantation in a patient with situs solitus, dextrocardia, and corrected transposition of the great arteries using a novel angiographic technique," *Journal of Arrhythmia*, Apr. 2014; 30(2):134-138.

Shenthar et al., "Transvenous permanent pacemaker implantation in dextrocardia: technique, challenges, outcome, and a brief review of literature," *Europace*, Sep. 2014; 16(9):1327-33.

Shirayama, "Role of atrial fibrillation threshold evaluation on guiding treatment," *Indian Pacing and Electrophysiology Journal*, Oct. 2003; 3(4):224-230.

Sperzel et al., "Intraoperative Characterization of Interventricular Mechanical Dyssynchrony Using Electroanatomic Mapping System—A Feasibility Study," Journal of Interventional Cardiac Electrophysiology, Nov. 2012, 35(2):189-96.

Spickler et al., "Totally Self-Contained Intracardiac Pacemaker," Journal of Electrocardiology, vol. 3(3&4): 324-331, 1970.

Sreeram et al., "Indications for Electrophysiology Study in children," *Indian Pacing and Electrophysiology Journal*, Apr.-Jun. 2008; 8(Suppl. 1):S36-S54.

Stockburger et al., "Optimization of cardiac resynchronization guided by Doppler echocardiography: haemodynamic improvement and intraindividual variability with different pacing configurations and atrioventricular delays," *Europace*, Oct. 2006; 8(10):881-6.

Stroobandt et al., "Prediction of Wenckebach Behavior and Block Response in DDD Pacemakers," *Pacing Clin Electrophysiol.*, Jun. 2006, 9(6):1040-6.

Suenari et al., "Idiopathic left ventricular tachycardia with dual electrocardiogram morphologies in a single patient," *Europace*, Apr. 2010; 12(4):592-4.

Sweeney et al., ".Analysis of Ventricular Activation Using Surface Electrocardiography to Predict Left Ventricular Reverse Volumetric Remodeling During Cardiac Resynchronization Therapy," Circulation, Feb. 9, 2010, 121(5):626-34.

Tan et al., "Electrocardiographi c evidence of ventricular repolarizati on remodelling during atrial fibrillation," *Europace*, Jan. 2008; 10(1):99-104.

Taramasco et al., "Internal low-energy cardioversion: a therapeutic option for restoring sinus rhythm in chronic atrial fibrillation after failure of external cardioversion," *Europace*, Jul. 1999; 1(3):179-82.

Testa et al., "Rate-control or rhythm-control: where do we stand?" *Indian Pacing and Electrophysiology Journal*, Oct. 2005; 5(4):296-304.

Thejus et al., "N-terminal Pro-Brain Natriuretic Peptide And Atrial Fibrillation," *Indian Pacing and Electrophysiology Journal*, Jan. 2009; 9(1):1-4.

Thornton et al., "Magnetic Assisted Navigation in Electrophysiology and Cardiac Resynchronisation: A Review," *Indian Pacing and Electrophysiology Journal*, Oct. 2006; 6(4):202-13.

Tilz et al., "In vivo left-ventricular contact force analysis: comparison of antegrade transseptal with retrograde transaortic mapping strategies and correlation of impedance and electrical amplitude with contact force," *Europace*, Sep. 2014; 16(9):1387-95.

Tomaske et al., "Do daily threshold trend fluctuations of epicardial leads correlate with pacing and sensing characteristics in paediatric patients?" *Europace*, Aug. 2007, 9(8):662-668.

Tomioka et al., "The effect of ventricular sequential contraction on helical heart during pacing: high septal pacing versus biventricular pacing," *European Journal of Cardio-thoracic Surgery*, Apr. 1, 2006; 29S1:S198-206.

Tournoux et al., "A 'Regularly Irregular' tachycardia: What is the diagnosis?" *Europace*, Dec. 2008; 10(12):1445-6.

Traykov et al., "Electrogram analysis at the His bundle region and the proximal coronary sinus as a tool to predict left atrial origin of focal atrial tachycardias," *Europace*, Jul. 2011; 13(7):1022-7.

Trudel et al., "Simulation of QRST integral maps with a membrane-based computer heart model employing parallel processing," *IEEE Trans Biomed Eng.*, Aug. 2004; 51(8):1319-29.

Tse et al., "Cardiac dynamics: Altemans and arrhythm ogenesis," *Journal of Arrhythmia*, Oct. 2016; 32(5):411-417.

Tse, "Mechanisms of cardiac arrhythmias," *Journal of Arrhythmia*, Apr. 2016; 32(2):75-81.

Ueda et al., "Outcomes of single- or dual-chamber implantable cardioverter defibrillator systems in Japanese patients," *Journal of Arrhythmia*, Apr. 2016; 32(2):89-94.

Van Dam et al., "Volume conductor effects involved in the genesis of the P wave," *Europace*, Sep. 2005; 7 Suppl 2:30-8.

Van den Berg et al., "Depletion of atrial natriuretic peptide during longstanding atrial fibrillation," *Europace*, Sep. 2004; 6(5):433-7.

Van Deursen, et al., " Vectorcardiography as a Tool for Easy Optimization of Cardiac Resynchronization Therapy in Canine LBBB Hearts," Circulation Arrhythmia and Electrophysiology, Jun. 1, 2012, 5(3): 544-52.

Van Opstal et al., "Paradoxical increase of stimulus to atrium interval despite His-bundle capture during para-Hisian pacing," *Europace*, Dec. 2009, 11(12): 1702-4.

Veenhuyzen et al., "Diagnostic pacing maneuvers for supraventricular tachycardia: part 1," *Pacing Clin Electrophysiol.*, Jun. 2011; 34(6):767-82.

Veenhuyzen et al., "Diagnostic pacing maneuvers for supraventricular tachycardias: part 2," *Pacing Clin Electrophysiol.*, Jun. 2012; 35(6):757-69.

Veenhuyzen et al., "Principles of Entrainment: Diagnostic Utility for Supraventricular Tachycardia," *Indian Pacing and Electrophysiology Journal*, 2008; 8(1):51-65.

Verbrugge et al., "Revisiting diastolic filling time as mechanistic insight for response to cardiac resynchronization therapy," *Europace*, Dec. 2013; 15(12):1747-56.

Verrier et al., "Mechanisms of ranolazine's dual protection against atrial and ventricular fibrillation," *Europace*, Mar. 2013; 15(3):317-324.

Verrijcken et al., "Pacemaker-mediated tachycardia with varying cycle length: what is the mechanism?" *Europace*, Oct. 2009; 11(10):1400-2.

Villani et al., "Reproducibility of internal atrial defibrillation threshold in paroxysmal and persistent atrial fibrillation," *Europace*, Jul. 2004; 6(4):267-72.

Violi et al., "Antioxidants for prevention of atrial fibrillation: a potentially useful future therapeutic approach? A review of the literature and meta-analysis," *Europace*, Aug. 2014; 16(8):1107-1116.

Weber et al., "Adenosine sensitive focal atrial tachycardia originating from the non-coronary aortic cusp," *Europace*, Jun. 2009; 11(6):823-6.

(56) References Cited

OTHER PUBLICATIONS

Weber et al., "Open-irrigated laser catheter ablation: relationship between the level of energy, myocardial thickness, and collateral damages in a dog model," *Europace*, Jan. 2014; 16(1):142-8.
Wegmoller, "Intra-Body Communication for Biomedical Sensor Networks," Diss. ETH, No. 17323, 1-173, 2007.
Wei et al., "Comparative simulation of excitation and body surface electrocardiogram with isotropic and anisotropic computer heart models," *IEEE Trans Biomed Eng.*, Apr. 1995; 42(4):343-57.
Weijs et al., "Clinical and echocardiographic correlates of intraatrial conduction delay," *Europace*, Dec. 2011; 13(12):1681-7.
Weiss et al., "The influence of fibre orientation, extracted from different segments of the human left ventricle, on the activation and repolarization sequence: a simulation study," *Europace*, Nov. 2007; 9(Suppl. 6):vi96-vi104.
Wetzel et al., "A stepwise mapping approach for localization and ablation of ectopic right, left, and septal atrial foci using electroanatomic mapping," *European Heart Journal*, Sep. 2002; 23(17):1387-1393.
Wlodarska et al., "Thromboembolic complications in patients with arrhythmogenic right ventricular dysplasia/cardiomyopathy," *Europace*, Aug. 2006; 8(8):596-600.
Wong et al., "A review of mitral isthmus ablation," *Indian Pacing and Electrophysiology Journal*, 2012; 12(4):152-170.
Wu et al., "Acute and long-term outcome after catheter ablation of supraventricular tachycardia in patients after the Mustard or Senning operation for D-transposition of the great arteries," *Europace*, Jun. 2013; 15(6):886-91.
Xia et al., "Asymmetric dimethylarginine concentration and early recurrence of atrial fibrillation after electrical cardioversion." *Pacing Clin Electrophysiol.*, Aug. 2008: 31(8):1036-40.
Yamazaki et al., "Acute Regional Left Atrial Ischemia Causes Acceleration of Atrial Drivers during Atrial Fibrillation," *Heart Rhythm*, Jun. 2013; 10(6):901-9.
Yang et al., "Focal atrial tachycardia originating from the distal portion of the left atrial appendage: Characteristics and long-term outcomes of radiofrequency ablation," *Europace*, Feb. 2012; 14(2):254-60.
Yiginer et al., "Advanced Age, Female Gender and Delay in Pacemaker Implantation May Cause TdP in Patients With Complete Atrioventricular Block," *Indian Pacing and Electrophysiology Journal*, Oct. 2010; 10(10):454-63.
Yoon et al., "Measurement of thoracic current flow in pigs for the study of defibrillation and cardioversion," *IEEE Transactions on Biomedical Engineering*, Oct. 2003; 50(10):1167-1773.
Yuan et al., "Recording nionophasic action potentials using a platinum-electrode ablation catheter," *Europace*, Oct. 2000, 2(4):312-9.
Yusuf et al., "5-Hydroxytryptamine and Atrial Fibrillation: How Significant is This Piece in the Puzzle?" *J Cardiovasc Electrophysiol.*, Feb. 2003, 14(2):209-14.
Zaugg et al., "Current concepts on ventricular fibrillation: a vicious circle of cardiomyocyte calcium overload in the initiation, maintenance, and termination of ventricular fibrillation," *Indian Pacing and Electrophysiology Journal*, Apr. 2004; 4(2):85-92.
Zhang et al., "Acute atrial arrhythmogenicity and altered Ca(2+) homeostasis in murine RyR2-P2328S hearts," *Cardiovascular Research*, Mar. 2011; 89(4):794-804.
Zoghi et al., "Electrical stunning and hibernation: suggestion of new terms for short-and long-term cardiac memory," *Europace*, Sep. 2004; 6(5):418-24.
Zografos et al., "Inhibition of the renin-angiotensin system for prevention of atrial fibrillation," *Pacing Clin Electrophysiol.*, Oct. 2010; 33(10):1270-85.
(PCT/US2014/066792) PCT Notification of Transmittal of the International Search Report and the Written Opinion of the International Searching Authority.
(PCT/US2014/013601) PCT Notification of Transmittal of the International Search Report and the Written Opinion of the International Searching Authority.

(PCT/US2014/036782) PCT Notification of Transmittal of the International Search Report and the Written Opinion of the International Searching Authority, dated Aug. 22, 2014, 11 pages.
International Search Report and Written Opinion for Application No. PCT/US2017/047378, 8 pages, dated Dec. 6, 2017.
(PCT/US2018/050988) PCT Notification of Transmittal of the International Search Report and the Written Opinion of the International Searching Authority, dated Nov. 14, 2018, 11 pages.
(PCT/US2018/050993) PCT Notification of Transmittal of the International Search Report and the Written Opinion of the International Searching Authority, dated Nov. 16, 2018, 7 pages.
(PCT/US2019/023642) PCT Notification of Transmittal of the International Search Report and the Written Opinion of the International Searching Authority, dated Jun. 28, 2019, 14 pages.
International Search Report and Written Opinion for PCT Application No. PCT/US2020/016369 dated May 26, 2020, 10 pages.
International Search Report and Written Opinion for PCT Application No. PCT/US2020/016468 dated May 7, 2020, 10 pages.
U.S. Appl. No. 61/819,946, filed May 6, 2013.
International Search Report and Written Opinion for PCT/US2018/056242, dated Feb. 11, 2019, 16 pages.
International Preliminary Report on Patentability for PCT/US2018/056242, dated Apr. 30, 2020, 9 pages.
International Search Report and Written Opinion for PCT/US2018/056257, dated Jan. 03, 2019, 16 pages.
International Preliminary Report on Patentability for PCT/US2018/056257, dated Apr. 30, 2020, 9 pages.
International Search Report and Written Opinion for PCT/US2018/056292, dated Jan. 30, 2019, 16 pages.
International Preliminary ReportonPatentability forPCT/US2018/056292, dated Apr. 30, 2020, 9 pages.
International Search Report and Written Opinion for PCT/US2018/056295, dated Dec. 19, 2018, 18 pages.
International Preliminary Report on Patentability for PCT/US2018/056295, dated Apr. 30, 2020, 9 pages.
Abdelrahman et al., "Clinical Outcomes of His Bundle Pacing Compared to Right Ventricular Pacing," *J Am Coll Cardiol*, May 22, 2018; 71(20):2319-2330.
Ahmed et al., "Right Ventricular Apical Pacing-induced Left Ventricular Dyssynchrony is Associated with a Subsequent Decline in Ejection Fraction," *Heart Rhythm*, Apr. 2014, 11(4):602-608.
Ajijola et al., "Permanent His-bundle pacing for cardiac re synchronization therapy: Initial feasibility study in lieu of left ventricular lead," *Heart Rhythm*, Sep. 2017; 14(9):1353-1361.
Al-Hesayen et al., "Adverse effects of atrioventricular synchronous right ventricular pacing on left ventricular sympathetic activity, efficiency, and hemodynamic status," *Am J Physiol Heart Circ Physiol.*, 2006, 291(5):H2377-H2379.
Anderson et al., "Wilhelm His Junior and his bundle," *J Electrocardiol.*, 2016; 49:637-643.
Babu et al., "Three-dimensional echocardiography with left ventricular strain analyses helps earlier prediction of right ventricular pacing-induced cardiomyopathy," *J Saudi Heart Assoc.*, Apr. 2018;30(2):102-107.
Barba-Pichardo et al., "Permanent His-Bundle Pacing in patients with Infra-Hisian Atrioventricular Block," *Revista Espanola de Cardiologia*, Jun. 2006, 59(6):553-558.
Cantù et al., "Validation of Criteria for Selective His Bundle and Para-Hisian Permanent Pacing," *Pacing & Clinical Electrophysiology*, Dec. 2006; 29(12):1326-1333.
Catanzari et al., "Permanent His-Bundle Pacing Maintains Long-Term Ventricular Synchrony and Left Ventricular Performance, Unlike Conventional Right Ventricular Apical Pacing," *EP Europace*, Apr. 2013; 15(4):546-553.
Chang et al., "Tricuspid Valve Dysfunction Following Pacemaker or Cardioverter-Defibrillator Implantation," *J Am Coll Cardiol.*, May 9, 2017; 69(18): 2331-2341.
Cho et al., Cerclage parahisian septal pacing through the septal perforator branch of the great cardiac vein: Bedside-to-bench development of a novel technique and lead, *Heart Rhythm Society*, Dec. 2019;16(12):1834-1840.

(56) References Cited

OTHER PUBLICATIONS

Chon et al., "TCT-18: Novel Concept of Catheter-Based Treatment for Tricuspid Regurgitation(Cerclage-TR block)," Pusan National University Yangsan Hospital, Yangsan, South Korea NHLBI, NIH, USA* Sep. 21, 2018.
Choy et al., "Right ventricular pacing impairs endothelial function in man," *Europace*, Jun. 2011; 13(6):853-858.
Dandamudi et al., "My Approach to Choosing Ventricular Pacing Sites in Patients With Severe Heart Failure," *J Cardio Electrophysiol.*, Jul. 2011; 22(7): 813-817.
Dandamudi et al., "How to perform permanent His bundle pacing in routine clinical practice," *Heart Rhythm Society*, Jun. 2016; 13(6): 1362-1366.
Dandamudi et al., "The Complexity of the His Bundle: Understanding Its Anatomy and Physiology through the Lens of the Past and the Present," Sep. 2016, DOI: 10.1111/pace.12925.
De Sisti et al., "Adverse Effects of Long-Term Right Ventricular Apical Pacing and Identification of Patients at Risk of Atrial Fibrillation and Heart Failure," PACE, Aug. 2012; 35(8):1035-1043.
Deshmukh et al., "Permanent, Direct His-Bundle Pacing: A Novel Approach to Cardiac Pacing in Patients With Normal Hus-Purkinje Activation," *Circulation*, Feb. 29, 2000, 101(8):869-877.
Deshmukh et al., "Direct His-Bundle Pacing: Present and Future," *PACE*, Jun. 2004; 27 [6 Pt.2]:862-70.
Deshmukh et al., "Direct His-Bundle Triple Site Pacing: A Novel Alternative to Bi-Ventricular Pacing," Heart Rhythm 2009, Presentation Abstract, May 14, 2009.
Deshmukh et al., "Comparison of Direct His Bundle and Biventricular Pacing," Heart Rhythm 2009, Poster Session V, May 15, 2009.
Deshmukh et al., "His bundle pacing: Initial experience and lessons learned," *J Electrocardiol.*, 2016; 49:658-663.
Dreger et al., "Pacing-induced cardiomyopathy in patients with right ventricular stimulation for >15 years," *EP Europace*, Feb. 2012; 14(2):238-242.
El-Sherif et al., "Normalization of Bundle Branch Block Patterns by Distal His Bundle Pacing. Clinical and Experimental Evidence of Longitudinal Dissociation in the Pathologic His Bundle," *Circulation*, Mar. 1978; 57:473-83.
Friedman et al., "Intermittent Capture of the Left Bundle With Permanent His Bundle Pacing: Mechanistic Insights and Implications for an Emerging Field," Aug. 1, 2016. doi: 10.1111/jce.13057.
Fröhlig et al., "His-bundle Stimulation and Alternative RV Stimulation Sites," Mar. 2008, 19(1):30-40, German.
Garrote et al., "His Bundle Pacing: Great in Theory, But Difficult in Practice," Revista Española de Cardiologia, 2006; 59(6):534-6.
Gierula et al., "Pacing-associated left ventricular dysfunction? Think reprogramming first!" *Heart*, May 2014; 100(10):765-769.
Gierula et al., "Patients with long-term permanent pacemakers have a high prevalence of left ventricular dysfunction," *J Cardiovasc Med*, Nov. 2015; 16(11):743-750.
Gillis et al., "Atrial Fibrillation After DDDR Pacemaker Implantation," *J Cardiovasc Electrophysiol.*, Jun. 2002;13(6):542-547.
Gula et al., "Feasibility of His Bundle Pacing as an Alternative Pacing Site: Measurement of His Refractoriness," *J Interv Card Electrophysiol.*, 2005; 12: 69-73.
Hayashi et al., "Impact of simple electrocardiographic markers as predictors for deterioration of left ventricular function in patients with frequent right ventricular apical pacing," *Heart Vessels*, Sep. 26, 2017; 33(3):299-308.
Hoyt et al., "Reversal of Left Ventricular Dysfunction with Biventricular or His-bundle Pacing Upgrade Late after A-V Nodal Ablation/ block," Heart Rhythm 2008 29th Scientific Sessions.
Hoyt et al., "Hemodynamic Evaluation of Direct His-Bundle and Parahisian Pacing," Heart Rhythm 2009, Poster Session V, May 15, 2009.
Huang et al., "Benefits of Permanent His Bundle Pacing Combined With Atrioventricular Node Ablation in Atrial Fibrillation Patients With Heart Failure With Both Preserved and Reduced Left Ventricular Ejection Fraction," *J Am Heart Assoc.*, Apr. 1, 2017; 6(4). pii: e005309.
Huang et al., "Feasibility of His Bundle Pacing in Correct Left Bundle Branch Block in Heart Failure Patients," Journal of the American College of Cardiology, vol. 70, No. 16, Suppl C, 2017, GW28-e1237, 1 page.
Karpawich et al., "Septal His-Purkinje Ventricular Pacing in Canines: A New Endocardial Electrode Approach," *Pacing Clinical Electrophysiology*, 1992; 15:2011-5.
Karpawich et al., "Altered Cardiac Histology Following Apical Right Ventricular Pacing in Patients with Congenital Atrioventricular Block," *Pacing Clin Electrophysiol.*, Sep. 1999; 22(9):1372-7.
Khoo et al., "Right Ventricular Pacing as Backup to His Bundle Pacing to Minimize Battery Drain," Heart Rhythm Society, Scientific Sessions, 2013.
Kiehl et al., "Incidence and predictors of right ventricular pacing-induced cardiomyopathy in patients with complete atrioventricular block and preserved left ventricular systolic function," *Heart Rhythm*, Dec. 2016; 13(12):2272-2278.
Kim et al., "Trans-coronary sinus intraseptal para-Hisian pacing: Cerclage pacing," *Heart Rhythm*, Apr. 2016, 13 (4):992-6.
Kim, "Mitral Loop Cerclage a catheter-based treatment of functional mitral regurgitation (CSTV)," JCR 2019, EuroPCR 2018.
Kronborg et al., "Left Ventricular Performance during para-His Pacing in Patients with High-degree Atrioventricular Block: an acute study," *Europtace*, Jun. 2014; 14(6):841-6. Epub Dec. 14, 2011.
Kronborg et al., "His or para-His Pacing Preserves Left Ventricular Function in AV Block: a Double-blind, Randomized, Crossover Study," *Europace*, Aug. 2014; 16(8): 1189-96.
Kronborg et al., "Left ventricular regional remodeling and lead position during cardiac resynchronization therapy," *Heart Rhythm*, Apr. 17, 2018; 15(10):1542-1549.
Kronborg et al., "His Bundle Pacing: Techniques and Outcomes," *Curr Cardiol Rep.*, Jul. 2016;18(8):76.
Laske et al., "Excitation of the Intrinsic Conduction System Through His and Interventricular Septal Pacing," *PACE*, Apr. 2006, 29(4):397-405.
Lederman et al., "Mitral Cerclage Annuloplasty," Cadiovascular Intervention Program at NHLBI, Update 2017.
Lindsay, "Deleterious Effects of Right Ventricular Pacing," *The New England Journal of Medicine*, Nov. 15, 2009; 361:2183-2185.
Lustgarten et al., "Direct His Bundle Pacing vs. BiVentricular Pacing in CRT Patients—A Cross-over Design Comparison," *Heart Rhythm*, 2013.
Lustgarten et al., "His-Bundle vs Biventricular Pacing in Resynchronization Therapy," *Heart Rhythm*, Jul. 2015; 12(7):1548-1557.
Lustgarten et al., "Step-wise Approach to Permanent His Bundle Pacing," *The Journal of Innovations in Cardiac Rhythm Management*, 2016; 7:2313-2321.
Mabo et al., "A Technique For Stable His-bundle Recording and Pacing: Electrophysiological and Hemodynamic Correlates," *Pacing Clinical Electrophysiology*,1995; 18:1894-901.
Mazza et al., "Incidence and Predictors of Heart Failure Hospitalization and Death in Permanent Pacemaker Patients: a Single-Center Experience over Medium-term Follow-up," Europace (2013) 15. 1267-1272.
Naperkowski et al.,, "Direct Implantation of Permanent His Bundle Pacing Lead in Patients with Complete Heart Block Without a Mapping Catheter or a Back-up Right Ventricular Lead: Feasibility and One year Follow-up," *Heart Rhythm*, Scientific Sessions, 2013.
Narula, "Longitudinal Dissociation in the His Bundle," *Circulation*, Dec. 1977; 56(6):996-1006.
Niazi et al., "Comparison of Lead Placement Strategies for Permanent His Bundle Pacing," Supplement, May 2011; 8(5).
Occhetta et al., "Prevention of Ventricular Desynchronization by Permanent Para-Hisian Pacing after Atrioventricular Node Ablation in Chronic Atrial Fibrillation," *Journal of the American College of Cardiology*, May 16, 2006, 47(10):1938-45.
Occhetta et al., "Future Easy and Physiological Cardiac Pacing," *Journal of Cardiology*, Jan. 26, 2011; 31(1):32-39.

(56) References Cited

OTHER PUBLICATIONS

Padeletti et al., "Rate Stabilization By Right Ventricular Apex or His Bundle Pacing in Patients With Atrial Fibrillation," *Europace*, 2005, 7:454-459.

Pastore et al., "Hisian area and Right Ventricular Apical Pacing Differently Affected Left Atrial Function: an Intra-patient Evaluation," *Europace*; 2013.

Pastore et al., "The Risk of Atrial Fibrillation during Right Ventricular Pacing," *Europace*, Mar. 2016; 18(3):353-8.

Scheinman et al., "Long-term His-Bundle Pacing and Cardiac Function," *Circulation* Feb. 29, 2000, 101:836-837.

Scherlag et al., "Functional aspects of His bundle physiology and pathophysiology: Clinical implications," *J Electrocardiol.*, Jan.-Feb. 2017; 50(1)151-155.

Sharma et al., "Permanent His-bundle Pacing is Feasible, Safe, and Superior to Right Ventricular Pacing in Routine Clinical Practice," *Heart Rhythm*, Feb. 2015; 12(2):305-312.

Sharma, "His Bundle Pacing Or Biventricular Pacing For Cardiac Resynchronization Therapy In Heart Failure: Discovering New Methods For An Old Problem," *J Atr Fibrillation*, Dec. 31, 2016.

Sharma et al., "Permanent His Bundle Pacing for Cardiac Resynchronization Therapy in Patients With Heart Failure and Right Bundle Branch Block," *Circ Arrhythm Electrophysiol*, Sep. 2018; 11(9):e006613.

Su et al., "Pacing and sensing optimization of permanent His-bundle pacing in cardiac resynchronization therapy/implantable cardioverter defibrillators patients: value of integrated bipolar configuration," *EP Europace*, 18(9):1399-1405.

Sweeney et al., "Adverse Effect of Ventricular Pacing on Heart Failure and Atrial Fibrillation Among Patients With Normal Baseline QRS Duration in a Clinical Trial of Pacemaker Therapy for Sinus Node Dysfunction," *Circulation*, Jun. 17, 2003, 107(23):2932-2937.

Teng et al., "Physiological mechanisms of QRS narrowing in bundle branch block patients undergoing permanent His bundle pacing," *J Electrocardiol.*, 2016; 49(5):644-648.

Teng et al., "Usefulness of His Bundle Pacing to Achieve Electrical Resynchronization in Patients With Complete Left Bundle Branch Block and the Relation Between Native QRS Axis, Duration, and Normalization," *American Journal of Cardiology*, May 28, 2016, 118(4):527-534.

Thambo et al., "Detrimental ventricular remodeling in patients with congenital complete heart block and chronic right ventricular apical pacing," *Circulation*, Dec. 21, 2004; 110(25):3766-72.

Vijayaraman et al., "Permanent His Bundle Pacing in Patients with Advanced Heart Block: Single Center Experience in Unselected Patients Without Mapping Catheter or Back-Up RV Pacing Lead," Heart Rhythm Society, Scientific Sessions, 2014.

Vijayaraman et al., "Anatomical approach to permanent His bundle pacing: Optimizing His bundle capture," *J Electrocardiol.*, 2016; 49: 649-657.

Vijayaraman et al., "How to Perform Permanent His Bundle Pacing: Tips and Tricks," *Pacing Clin Electrophysiol.*, Dec. 2016; 39(12): 1298-1304.

Vijayaraman et al., "Permanent His Bundle Pacing Reduces Mortality/Morbidity In Pacemaker Population Compared to Right Ventricular Pacing," Heart Rhythm Society (HRS) Scientific Sessions May 12, 2017; C-AB26-06.

Vijayaraman et al., "The Continued Search for Physiological Pacing Where Are We Now?" *Journal of the American College of Cardiology*, Jun. 27, 2017; 69(25):3099-3114.

Vijayaraman et al., "His Bundle Injury Current during Implantation of Permanent His Bundle Pacing Lead Predicts Excellent Pacing Outcomes," Heart Rhythm Society, Scientific Sessions, 2014.

Vijayaraman et al., "Acute His-Bundle Injury Current during Permanent His-Bundle Pacing Predicts Excellent Pacing Outcomes," Pacing Clinical Electrophysiology, Jan. 14, 2015. doi: 10.1111/pace.12571.

Vijayaraman et al., "Electrophysiologic Insights Into Site of Atrioventricular Block: Lessons From Permanent His Bundle Pacing," *JACC: Clinical Electrophysiology*, Dec. 2015; 1(6):571-581.

Vijayaraman et al., "Permanent His bundle pacing: Electrophysiological and echocardiographic observations from long-term follow-up," *PACE*, Jul. 2017; 40:883-891.

Vijayaraman et al., "Permanent His Bundle Pacing (HBP): Recommendations From A Multi-Center HBP Collaborative Working Group For Standardization Of Definitions, Implant Measurements And Follow-Up," Oct. 2017; DOI: http://dx.doi.org/10.1016/j.hrthm.

Vijayaraman et al., "His Bundle Pacing," *Journal of the American College of Cardiology*, Aug. 2018; 72(8).

Wilkoff et al., "Dual-Chamber Pacing or Ventricular Backup Pacing in Patients With an Implantable Defibrillator, The Dual Chamber and VVI Implantable Defibrillator (DAVID) Trial," *JAMA*, Dec. 25, 2002; 288(24):3115-3123.

Wilson et al., "Strategically targeting calcium: Altering activation sequence to reverse remodel the failing ventricle," *Heart Rhythm*, Oct. 2018;15(10):1550-1551.

Worsnick et al., "Direct His Bundle Pacing in a Patient with Complete Heart Block Requiring Implantable Defibrillator," *The Journal of Innovation in Cardiac Rhythm Management*, Aug. 2013; 492.

Yamauchi et al., "Permanent His-Bundle Pacing After Atrioventricular Node Ablation in a Patient With Chronic Atrial Fibrillation and Mitral Regurgitation," *Circ J*, 2005; 69:510-514.

Zanon et al., "A Feasible Approach for Direct His-Bundle Pacing Using a new Steerable Catheter to Facilitate Precise Lead Placement," *JCE*, Jan. 2006; 17:29-33.

Zanon et al., "Direct His Bundle Pacing Preserves Coronary Perfusion Compared With Right Ventricular Apical Pacing: a Prospective, Cross-over Mid-term Stud," *Europace*; May 2008; 10(5):580-7.

Zanon et al., "Safety and Performance of a System Specifically Designed for Selective Site Pacing," *Pacing and Clinical Electrophysiology*, Mar. 2011; 34(3):339-347.

Zanon et al., "Direct His bundle and Parahisian Cardiac Pacing," *A.N.E.*, Apr. 2012; 17(2):70-8.

Znojkiewicz et al., "Direct His-bundle Pacing in Patients Following AV Node Ablation," Heart Rhythm, May 2011; 8(5):Supplement.

* cited by examiner

Anterior view of frontal section

LEAD-IN-LEAD SYSTEMS AND METHODS FOR CARDIAC THERAPY

FIELD

The present technology is generally related to implantable medical devices, systems, and methods. In particular, the present technology is related to implantable lead delivery for cardiac sensing and therapy.

BACKGROUND

Implantable medical devices (IMDs), such as cardiac pacemakers or implantable cardioverter defibrillators, deliver therapeutic stimulation to patients' hearts. Patients with a conduction system abnormality, such as poor atrioventricular (AV) node conduction or poor sinoatrial (SA) node function, may receive an IMD, such as a pacemaker, to restore a more normal heart rhythm and AV synchrony. Some types of IMDs, such as cardiac pacemakers, implantable cardioverter-defibrillators (ICDs), or cardiac resynchronization therapy (CRT) devices, provide therapeutic electrical stimulation to a heart of a patient via electrodes on one or more implantable endocardial, epicardial, or coronary venous leads that are positioned in or adjacent to the heart. The therapeutic electrical stimulation may be delivered to the heart in the form of pulses or shocks for pacing, cardioversion, or defibrillation. In some cases, an IMD may sense intrinsic depolarizations of the heart and control the delivery of therapeutic stimulation to the heart based on the sensing.

Existing pacing techniques involve pacing one or more of the four chambers of patient's heart 12—left atrium (LA) 33, right atrium (RA) 26, left ventricle (LV) 32 and right ventricle (RV) 28, all of which are shown in the anterior view of a frontal section of patient's heart 12 illustrated in FIG. 1. Some therapeutic pacing techniques involve the cardiac conduction system. The cardiac conduction system, like a "super highway," may be described as quickly conducting electrical pulses whereas pacing cardiac muscle tissue may slowly conduct electrical pulses, like "traveling on a dirt road." The cardiac conduction system includes SA node 1, atrial internodal tracts 2, 4, 5 (i.e., anterior internodal 2, middle internodal 4, and posterior internodal 5), atrioventricular node (AV node) 3, His bundle 13 (also known as the atrioventricular bundle or bundle of His), and bundle branches including the left bundle branch (LBB) 8a and the right bundle branch (RBB) 8b. FIG. 1 also shows the arch of aorta 6 and Bachman's bundle 7. The SA node, located at the junction of the superior vena cava and right atrium, is considered to be the natural pacemaker of the heart since it continuously and repeatedly emits electrical impulses. The electrical impulse spreads through the muscles of RA 26 to LA 33 to cause synchronous contraction of the atria. Electrical impulses are also carried through atrial internodal tracts to AV node 3—the sole connection between the atria and the ventricles.

Conduction through the AV nodal tissue takes longer than through the atrial tissue, resulting in a delay between atrial contraction and the start of ventricular contraction. The AV delay, which is the delay between atrial contraction and ventricular contractor, allows the atria to empty blood into the ventricles. Then, the valves between the atria and ventricles close before causing ventricular contraction via branches of the bundle of His.

His bundle 13 is located in the membranous atrioventricular septum near the annulus of the tricuspid valve. His bundle 13 splits into right and left bundle branches 8a, 8b and are formed of specialized fibers called "Purkinje fibers" 9. Purkinje fibers 9 may be described as rapidly conducting an action potential down the ventricular septum, spreading the depolarization wavefront quickly through the remaining ventricular myocardium, and producing a coordinated contraction of the ventricular muscle mass.

SUMMARY

The techniques of this disclosure generally relate to a lead-in-lead system and methods for cardiac therapy. The lead-in-lead system allows the leads to be translatable or rotatable relative to one another to facilitate capturing desired parts of the patient's heart. In other words, the lead-in-lead system may provide a customized implantation solution for each patient.

In one aspect, the present disclosure provides a system that includes a first implantable lead having a distal portion and a first electrode coupled to the distal portion of the first implantable lead. The first electrode is configured to be implanted at an implantation site on or in a tissue structure of a patient's heart. The system also includes a second implantable lead having a distal portion and a second electrode coupled to the distal portion of the second implantable lead. The second electrode is configured to be implanted at the implantation site distal to the first electrode within the tissue structure of the patient's heart. The distal portion of the second implantable lead is guided by the distal portion of the first implantable lead to the implantation site.

In another aspect, the present disclosure provides a method that includes implanting a first electrode of a first implantable lead at an implantation site on or in a tissue structure of a patient's heart. The method also includes advancing a second implantable lead having a second electrode guided by a distal portion of the first implantable lead to the implantation site within the tissue structure of the patient's heart. The method further includes implanting the second electrode at the implantation site distal to the first electrode within the tissue structure of the patient's heart.

In another aspect, the present disclosure provides an implantable medical device that includes a plurality of electrodes. The plurality of electrodes includes a first electrode configured to be implanted at an implantation site on or in a tissue structure of a patient's heart. The plurality of electrodes also includes a second electrode configured to be implanted at the implantation site distal to the first electrode within the tissue structure of the patient's heart. The second electrode is translatable relative to the first electrode after the first electrode has been implanted to allow the second electrode to be implanted at various depths within the tissue structure of the patient's heart. The implantable medical device also includes a therapy delivery circuit operably coupled to the plurality of electrodes to deliver cardiac therapy to the patient's heart, and a sensing circuit operably coupled to the plurality of electrodes to sense electrical activity of the patient's heart. The implantable medical device further includes a controller having processing circuitry operably coupled to the therapy delivery circuit and the sensing circuit. The controller is configured to provide electrical pulses to at least the second electrode to test one or more depths of the second electrode within the tissue structure of the patient's heart.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
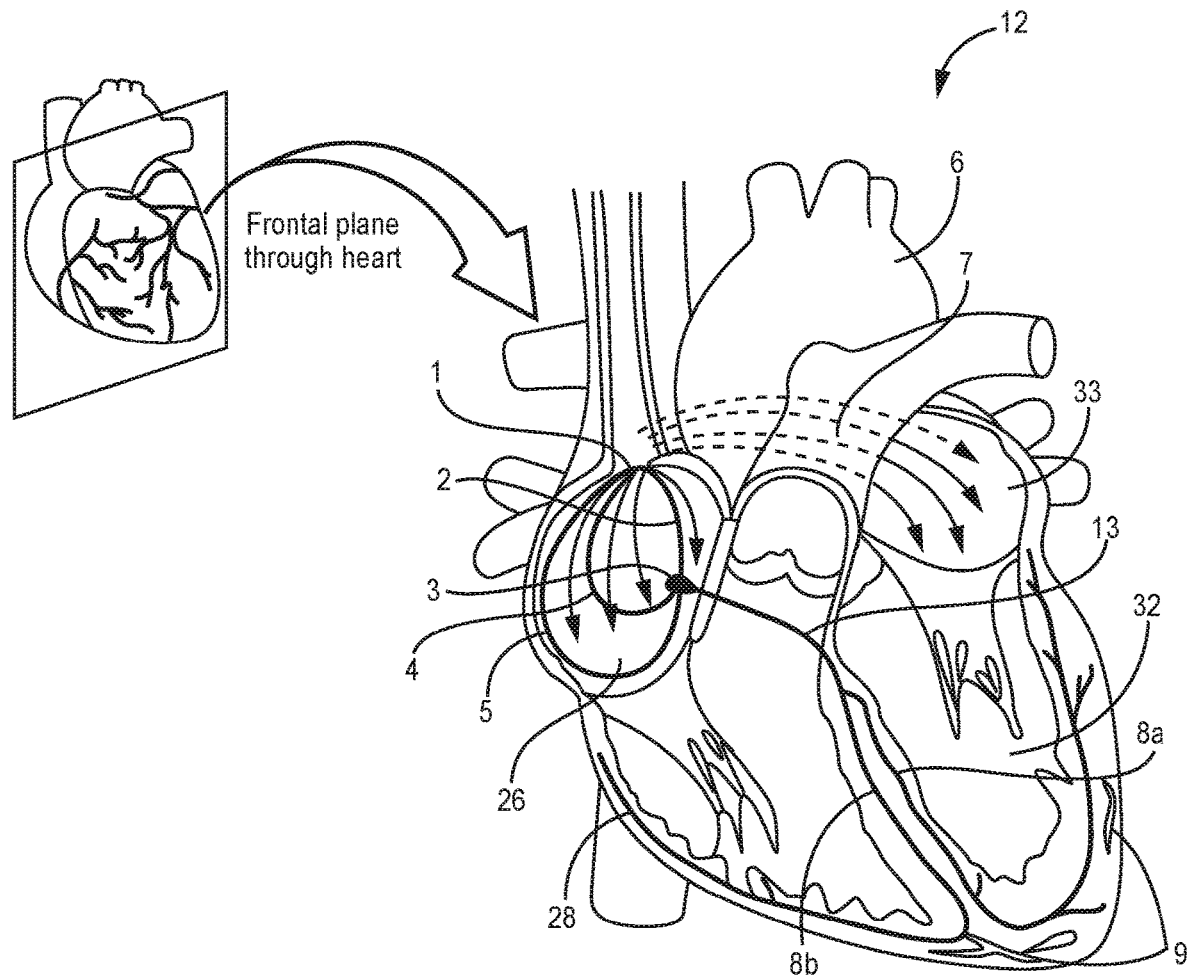
FIG. 1 is an illustration of a patient's heart as one example of an environment for using the lead-in-lead systems and methods of the present disclosure.

The present disclosure relates to a lead-in-lead system and methods for cardiac therapy. The lead-in-lead approach may provide efficient and effective delivery of electrodes to various locations in the patient's heart, including at the triangle of Koch for ventricle-from-atrium (VfA) therapy, at the right ventricular septal wall for dual bundle-branch pacing, and in the coronary vasculature for left side sensing and pacing. VfA therapy may relate to providing an electrode to capture the LV implanted through the AV septum, such as the RA-LV septal wall. The lead-in-lead system includes a first implantable lead and a second implantable lead. One of the leads may be a bipolar lead, while the other lead may be a unipolar lead. The leads may include electrodes that are passive to monitor electrical activity or active to provide pacing pulses. The lead-in-lead system allows the leads to be translatable or rotatable relative to one another to facilitate capturing desired parts of the patient's heart. In other words, the lead-in-lead system may provide a customized implantation solution for each patient.

As used in this specification and the appended claims, the term "or" is generally employed in its sense including "and/or" unless the content clearly dictates otherwise.

Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

Figure 2:
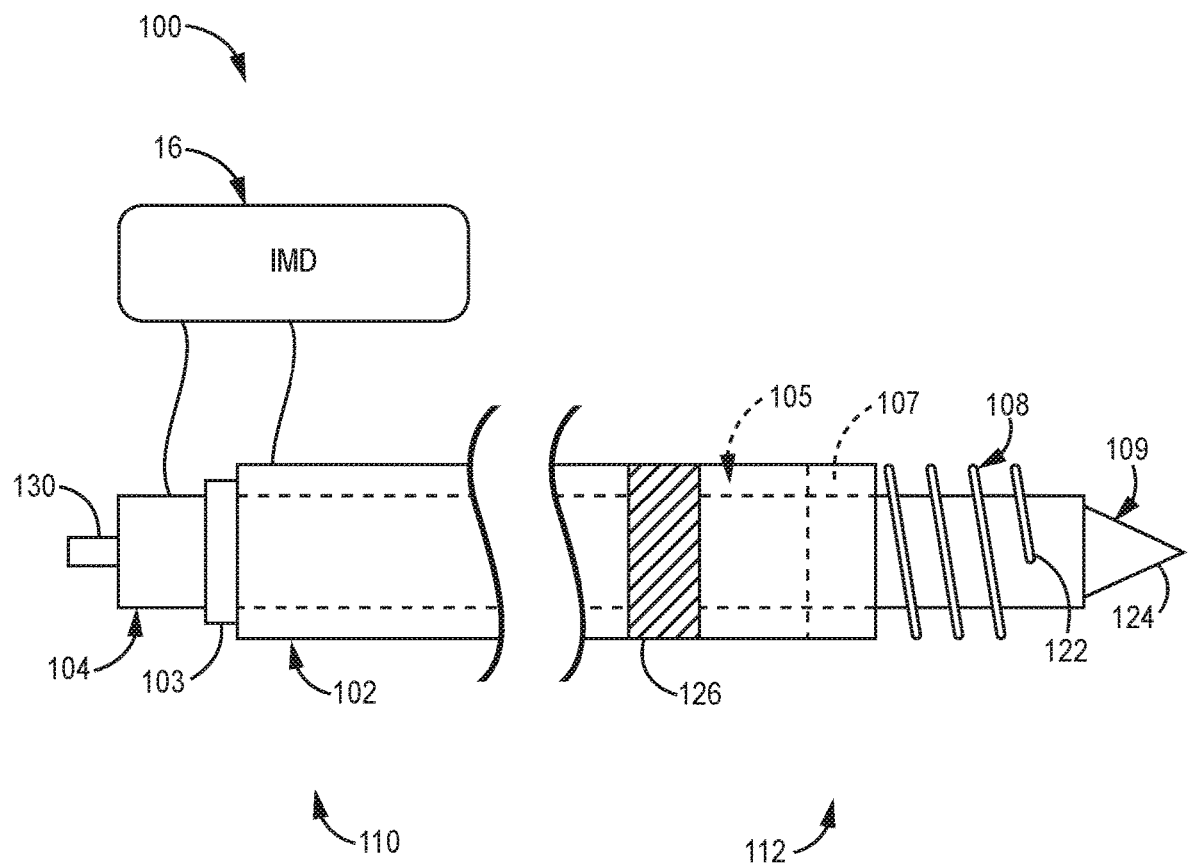
FIGS. 2-3 are schematic illustrations of examples of lead-in-lead systems according to the present disclosure for use with, e.g., the patient's heart of FIG. 1.
Figure 3:
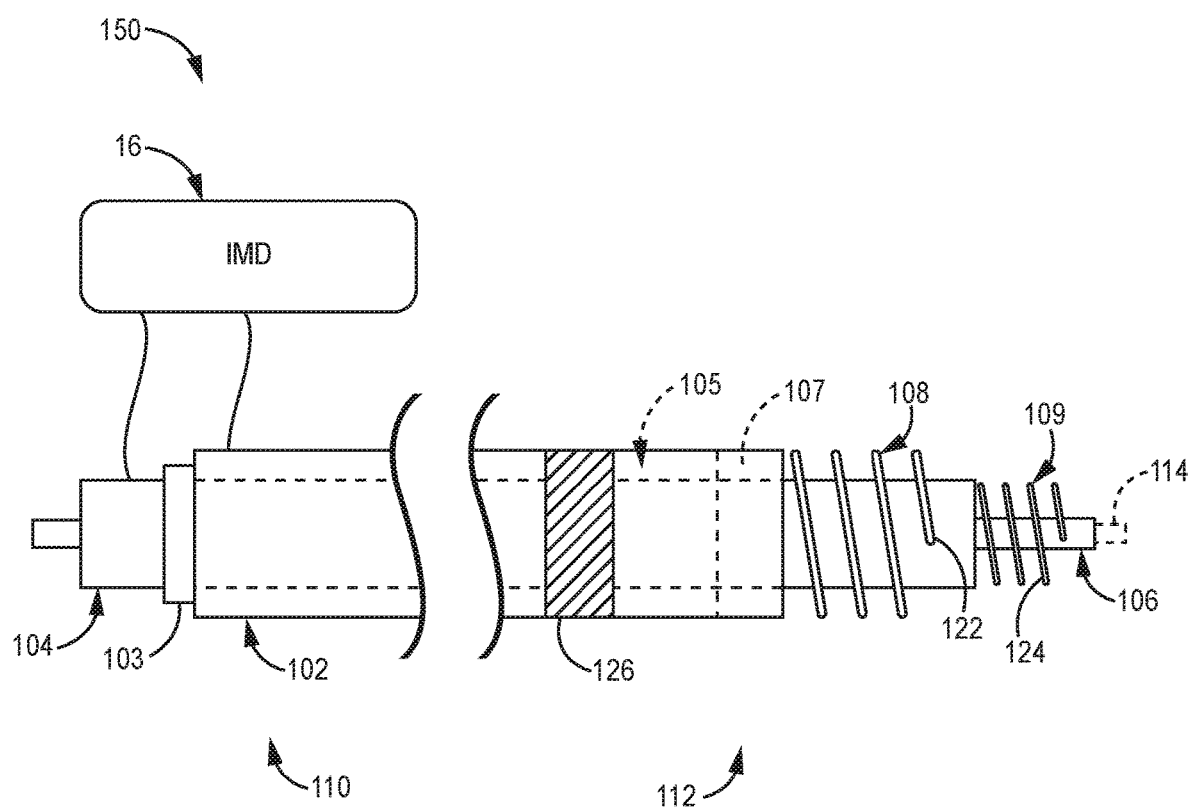

Various embodiments of this disclosure provide a lead-in-lead system for cardiac or other therapies. FIGS. 2 and 3 illustrate different examples of lead-in-lead systems. FIG. 2 shows a system 100 including a first implantable lead 102 and a second implantable lead 104, which are operably couplable an IMD 16, and further including a stylet 130. FIG. 3 shows a system 150 also including the first implantable lead 102, the second implantable lead 104, the IMD 16, and a guidewire 106 instead of the stylet 130. The system 100 and the system 150 may be similar in many aspects except where described differently herein.

Figure 23:
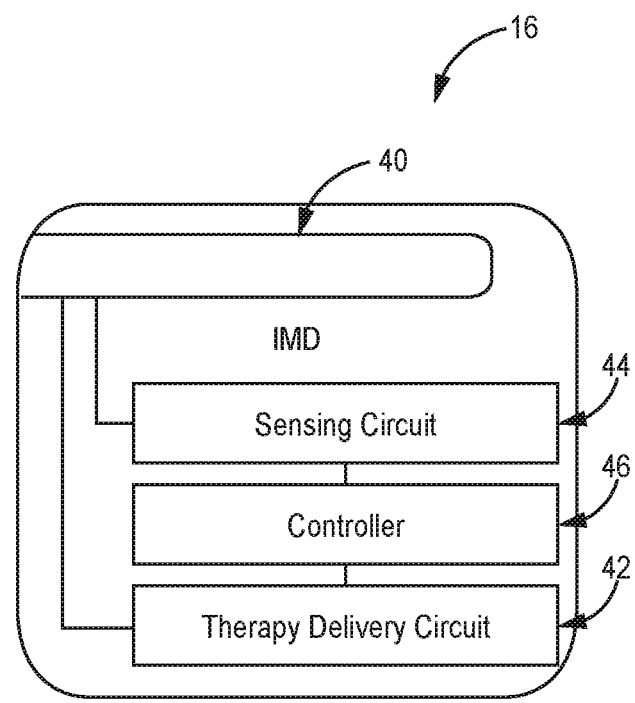
FIG. 23 is a schematic illustration of one example of an implantable medical device for use with, e.g., the lead-in-lead systems of FIG. 2 or FIG. 3.

The IMD 16 may be any suitable device known to one of ordinary skill in the art having the benefit of this disclosure that can operably couple to one or more implantable leads and one or more electrodes to sense electrical activity or to deliver therapy. The IMD 16 may be, for example, an implantable pacemaker, cardioverter, and/or defibrillator that provides electrical signals to a patient's heart via electrodes coupled to one or more of leads. Further non-limiting examples of the IMD 16 include: a pacemaker with a medical lead, an ICD, an intracardiac device, a subcutaneous ICD (S-ICD), and a subcutaneous medical device (e.g., nerve stimulator, inserted monitoring device, etc.). One example of an IMD 16 is shown in FIG. 23.

Various implantation sites may be targeted using lead-in-lead systems. In one or more embodiments described herein, the systems are configured to be implanted in the triangle of Koch region in the atrioventricular wall of the patient's heart into the tissue structure between the right atrium and left ventricle of the patient's heart. In one or more embodiments described herein, the systems are configured to be implanted in the ventricular septal wall into the tissue structure is between the right ventricle and the left ventricle of the patient's heart. In some embodiments described herein, the systems are configured to be implanted in the coronary sinus or a coronary vein. Further, in some embodiments described herein, the system are configured to be implanted in the LV myocardium.

As can be seen in either FIG. 2 or FIG. 3, the first implantable lead 102 may be mechanically coupled to the second implantable lead 104 by a lead fixture element 103. In some embodiments, the first implantable lead 102 and the second implantable lead 104 may be formed separately. In such a configuration, the leads may be advanced one at a time. The second implantable lead 104 may be advanced through a lumen of the first implantable lead 102 to an implantation site, for example, after the first implantable lead has been fixed at the implantation site. In other embodiments, the first implantable lead 102 and the second implantable lead 104 may be formed into a single lead assembly or assembled lead configured to concurrently advance toward the implantation site.

The lead fixture element 103 may be described as a plug coupled between the leads. The lead fixture element 103 may facilitate translation or rotation of the leads relative to one another. In one or more embodiments described herein, the first implantable lead 102 is translatable along a longitudinal direction relative to the second implantable lead 104, which may facilitate proper positioning of the leads during implantation to sense electrical activity or to deliver cardiac therapy. The second implantable lead 104 may translated to extend, or be advanced, distally from an end of the first implantable lead 102 to penetrate further into the tissue structure or to extend distally further into a space than the first implantable lead.

As used herein, the "longitudinal" direction refers to a direction along or parallel to a direction between a proximal part and a distal part of an elongate member, such as an implantable lead.

The system 100 may define a proximal portion 110 and a distal portion 112, as well as a proximal end and a distal end. As illustrated, the double curve lines between the proximal portion 110 and the distal portion 112 indicate that the leads may be longer than shown. Each of the first implantable lead 102 and the second implantable lead 104 may also include a respective proximal portion and a respective distal portion, as well as a respective proximal end and a respective distal end.

The second implantable lead 104 may be at least partially received within the first implantable lead 102, for example, to guide the second implantable lead. In some embodiments, the first implantable lead 102 may include a lumen 105 sized to receive the second implantable lead 104. In some embodiments, an opening of lumen 105 may be larger than a cross-section of the second implantable lead 104. A sealing element 107 may be coupled between the implantable leads to seal the distal portion of the first implantable lead 102 from fluid ingress, for example, at or near the distal end. In other words, the sealing element 107 may prevent, or substantially prevent, fluid from entering inside the lumen 105 to the space between the implantable leads.

A guidewire or a stylet may be used to advance and guide the lead-in-lead system 100 to one or more implantation sites. The guidewire or stylet may be received at least partially into a lumen of the second implantable lead 104. As shown in FIG. 2, a stylet 130 may be at least partially received within the lumen of the second implantable lead 104 from the proximal end of the lead. A distal end of the stylet 130 may be retained within the distal portion of the second implantable lead 104, for example, proximal to a closed distal end of the second implantable lead. As shown in FIG. 3, a guidewire 106 may be at least partially received within the lumen of the second implantable lead 104 from the proximal end of the lead and may extend distally from the lead. In one or more embodiments described herein, the guidewire 106 may be used to pierce into or through a tissue structure of the patient's heart.

In other embodiments, the second implantable lead 104 may not include a lumen. For example, the guidewire 106 may extend through the lumen 105 of the first implantable lead 102, and the guidewire 106 may be exchanged with the second implantable lead 104 during an implantation process.

As used herein, a "tissue structure" refers to tissue forming any structures of the heart, such as a heart wall. The tissue structure may define a surface of the heart. Non-limiting examples of tissue structures include an atrioventricular septal wall (such as the RA-LV septum), a ventricular septal wall (such as the RV-LA septum), a wall forming the apex of the patient's heart, and a vessel wall (such as the vessel wall of the coronary sinus or a coronary vein).

The first implantable lead 102 may be used to guide the second implantable lead 104 to an implantation site or past a first implantation site to a second implantation site. In one or more embodiments described herein, the distal portion of the first implantable lead 102 may be used to guide the distal portion of the second implantable lead 104, for example, to the same implantation site. For example, in one or more embodiments described herein, the implantation site may be the triangle of Koch region in the atrioventricular septal wall of the patient's heart or the ventricular septal wall in the basal (e.g., high basal or high septal) region or apical (e.g., low septal or near the apex) region. Implantation in the triangle of Koch region of the atrioventricular septal wall may facilitate pacing of the His bundle or ventricular myocardium. Implantation in the basal region of the ventricular septal wall may facilitate pacing of the His bundle branches. Implantation in the apical region may facilitate pacing of Purkinje fibers.

In other embodiments, the distal portion of the first implantable lead 102 may be implanted at a first implantation site, and the distal portion of the second implantable lead 104 may be implanted distally at a second implantation site. For example, in one or more embodiments described herein, the first implantation site may be in the coronary sinus or a coronary vein of the patient's heart and the second implantation site may be distal to the first implantation site in the coronary vein or in the myocardium (e.g., left ventricular myocardium) of the patient's heart. In one or more embodiments described herein, the second implantation site may be in the myocardium through the epicardium of the patient's heart outside of the coronary sinus and the coronary veins. In other words, the second implantation site in the myocardium may be accessed using the pericardial cavity.

Implantation leads may be secured, or fixed, for implantation concurrently or independently. For example, the first implantation lead 102 may be fixed before, during, or after the second implantation lead 104 is fixed. In some embodiments, after one of the implantation leads is fixed for implantation, the other of the implantation leads may be secured. In one example, the second implantation lead 104 may be fixed for implantation after the first implantation lead 102 is fixed for implantation. In another example, the first implantation lead 102 may be fixed for implantation after the second implantation lead 104 is fixed for implantation.

The second implantable lead 104 may be freely rotatable relative to the first implantable lead 102, or vice versa, which may facilitate certain types of fixation for implantation. For example, a rotating motion may be used to secure the first implantable lead 102 or the second implantable lead 104 to an implantation site using a fixation element that responds to a rotating motion.

In one or more embodiments described herein, one or both implantation leads may include a fixation element used to secure the respective lead to a tissue structure at a selected implantation site. Non-limiting examples of fixation elements include a drill and a helix. In one or more embodiments, such as shown in FIG. 2, the system 100 includes a fixation element 108 of the first implantable lead 102 may include a helix structure, and a fixation element 109 of the second implantable lead 104 may include a drill structure. In one or more embodiments, such as shown in FIG. 3, the system 150 includes a fixation element 108 of the first implantable lead 102 may include a helix structure, and a fixation element 111 of the second implantable lead 104 may include a helix structure.

In general, any suitable type of drill or helix structure known to one of ordinary skill in the art having the benefit of this disclosure may be used for fixation elements. The fixation elements of the implantable leads may be configured to rotate in the same or opposite directions. For example, one fixation element may be configured to screw into a tissue structure when the respective lead is rotated clockwise and the other fixation element may be configured to screw into the tissue structure when the respective other lead is rotated clockwise (e.g., the same direction) or counterclockwise (e.g., the opposite direction). In addition, or as an alternative, to fixation elements, one or both implantation leads may include a canted lead structure to facilitate fixing the respective implantation lead in a vessel, such as the coronary sinus or a coronary vein.

In one or more embodiments described herein, a puncture element 114 may extend distally from the guidewire 106. The puncture element 114 may be formed integrally or separately from the guidewire 106. The puncture element 114 may have a drill structure that may be used to drill into a tissue structure at an implantation site. In one or more embodiments described herein, when using the puncture element 114, the fixation element 111 of the second implantable lead 104 may have a helix structure as shown in FIG. 3. In one or more embodiments described herein, when not using the guidewire 106, the fixation element 109 of the second implantable lead 104 may have a drill structure as shown in FIG. 2. In one or more other embodiments described herein, the guidewire 106 having the puncture element 114 may be used with the fixation element 109 having a drill structure. For example, the guidewire 106 may extend through a lumen of the fixation element 109 and extend distally from the fixation element 109. In other words, the guidewire 106 may be used with the system 100 of FIG. 2 instead of the stylet 130.

The puncture element 114 may be used to provide a micropuncture through a tissue structure, such as a vessel wall, of the patient's heart. For example, the micropuncture into the pericardial cavity of the patient's heart may be formed at a location along the coronary sinus or a coronary vein. In other words, the micropuncture may be formed inferior to the coronal oblique transseptal plane of the patient's heart. In some embodiments, the puncture element 114 includes a microneedle configured to provide the micropuncture in the coronary sinus or coronary vein.

As used herein, the term "micropuncture" refers to a puncture through a wall that has a largest dimension, for example, along a major axis or a diameter, of less than about 1 millimeter or on the order of about 100 micrometers, about 10 micrometers, or about 1 micrometer.

When forming a puncture in a vessel wall, a structure of the first implantable lead 102 may be configured to seal the puncture after implantation. In some embodiments, the structure may include a lead body or sheath of the implantable lead. For example, the first implantable lead 102 may be fixed against the vessel wall toward the pericardial cavity. The vessel wall may be sealed by the active fixation, and the second implantable lead 104 may extend radially from the first implantable lead 102, through the vessel wall, and into the pericardial cavity. In some embodiments, the structure may include the sealing element 107.

As used herein, the phrase "to seal the puncture" refers to partial sealing, complete sealing, or almost complete sealing of the puncture between a vessel and a space of the patient's heart. For example, the sealing of the puncture may be sufficient to prevent major tamponade (e.g., resulting from fluid buildup in the pericardial cavity).

One or both of the implantable leads includes one or more electrodes. In some embodiments described herein, the first implantable lead 102 includes a first electrode 122 coupled to the first implantable lead, and the second implantable lead 104 includes a second electrode 124 coupled to the second implantable lead. Each fixation element may be formed integrally or separately from the respective electrode. In the illustrated embodiments shown in FIG. 2 and FIG. 3, the electrodes are integrally formed with their respective fixation elements. The integrally formed electrodes are configured to pierce into the tissue structure of the patient's heart. In one or more embodiments described herein, the integrally formed electrodes are formed at a distal portion or end of the respective fixation element.

The first electrode 122 or the second electrode 124 may disposed on the distal portion or at the distal end of the respective implantable lead. In one or more embodiments described herein, the first electrode 122 or the second electrode 124 may be disposed proximal to a distal end of the respective implantable lead, for example, when a structure of the respective implantable lead is used to seal a puncture in a tissue structure, such as a vessel wall.

The first electrode 122 and the second electrode 124 may be described as cathode electrodes (or simply cathodes) for pacing or sensing. For example, the electrodes may provide various pacing vectors for different cardiac therapies, such as CRT. The first implantable lead 102 or the second implantable lead 104 may include a return electrode 126, which may be described as a common anode electrode (or simply an anode). In the illustrated embodiments of FIG. 2 and FIG. 3, the return electrode 126 is coupled to the first implantable lead 102 and is shown as a ring electrode. The return electrode 126 may be proximal or distal to the cathode electrodes. The return electrode 126 may be proximal to the first electrode 122 and proximal to the second electrode 124. The implantable lead having two electrodes (e.g., cathode and anode electrodes) may be described as a bipolar lead.

In one or more embodiments described herein, the second implantable lead 104 includes multiple second electrodes 124 (e.g., a plurality of second electrodes), which may be used to provide multiple sensing or pacing sites along the lead. The first electrode 122 and the return electrode 126 may be proximal to one or more of the multiple second electrodes 124.

In one or more embodiments described herein, the first electrode 122 is configured to be implanted on or in a tissue structure of a patient's heart at the implantation site, and the second electrode 124 is configured to be implanted at the same implantation site distal to the first electrode within the tissue structure of the patient's heart. After one of the electrodes is implanted, the other electrode may be translatable relative to the implanted electrode. For example, the second electrode 124 may be translatable relative to the first electrode 122, even after the first electrode is implanted, to allow the second electrode to be implanted at various depths within the tissue structure of the patient's heart. The translatable coupling of the first implantation lead 102 and the second implantation lead 104 may facilitate the translatable relationship between the electrodes.

In one or more embodiments described herein, the first electrode 122 is configured to be implanted at a first implantation site in the coronary sinus or in a coronary vein of the patient's heart, and the second electrode 124 is configured to be implanted at a second implantation site distal to the first electrode in the patient's heart. For example, the second electrode 124 may be implanted in a coronary vein.

One or more of the electrodes may be configured to sense electrical activity or to provide pacing pulses (e.g., in delivering cardiac therapy). In one or more embodiments described herein, both the first electrode 122 and the second electrode 124 are configured to provide pacing pulses. One or both electrodes may also be configured to sense electrical activity. In one or more embodiments described herein, the first electrode 122 is configured to only sense electrical activity, and the second electrode 124 is configured to provide pacing pulses. The second electrode 124 may also be configured to sense electrical activity. In some embodiments, a plurality of second electrodes 124 may be configured to deliver cardiac therapy to or sense electrical activity of the left ventricle.

In general, one or more of the electrodes may be configured to deliver electrical pulses to test one or more locations of the respective electrode in the patient's heart. In one or more embodiments described herein, one or more depths of the respective electrode in the tissue structure of the patient's heart may be tested. The test electrical pulses may facilitate identifying an appropriate depth or an appropriate surface location on a tissue structure for the electrode to capture the desired sensing or pacing. In one or more embodiments described herein, the first electrode 122 or the second electrode 124 may be tested at variable depths or surface locations before being implanted at a selected depth. In one example, an implantation depth or surface location of the first electrode 122 may be tested to determine whether the RBB is captured, and the implantation depth of the second electrode 124 may be tested to determine whether the LBB is captured. In another example, a surface location of the first electrode 122 may be tested to determine whether the RA myocardium is captured, and the implantation depth of the second electrode 124 may be tested to determine whether the LV myocardium or His bundle is captured.

In one or more embodiments described herein, one or more locations of the respective electrode in the patient's heart may be tested. In one example, the first electrode 122 may be tested to determine whether the LA is captured, and the second electrode 124 may be tested to determine whether the LV is captured. The electrodes may be advanced through a vessel, such as the coronary sinus or a coronary vein, of the patient's heart. One or more locations of the first electrode 122 in and along the vessel may be tested, for example, to capture the LA. Additionally, or alternatively, one or more locations of the second electrode 124 in the vessel or in the myocardium along the vessel may be tested, for example, to capture the LV. Further, one or more of the electrodes may be advanced into a space of the patient's heart, such as the pericardial cavity. One or more locations of the second electrode 124 in the myocardium along the pericardial cavity may be tested, for example, to capture the LV.

Although both electrodes may be implanted at the same implantation site, different parts of the patient's heart may be captured by advancing the electrodes to different depths. In one or more embodiments described herein, the first electrode 122 is implantable in the RA of the patient's heart to deliver cardiac therapy to or sense electrical activity of the RA of the patient's heart, and the second electrode 124 is implantable from the triangle of Koch region of the RA of the patient's heart to deliver cardiac therapy to or sense electrical activity of the LV in the basal region, septal region, or basal-septal region of the left ventricular myocardium of the patient's heart for VfA cardiac therapy.

In one or more embodiments described herein, the first electrode 122 is implantable closer to a first bundle branch of the cardiac conduction system of the patient's heart than the second electrode 124, and the second electrode is implantable closer to a second bundle branch of the cardiac conduction system of the patient's heart than the first electrode. For example, the first electrode 122 may be implanted closer to the RBB 8*b* (FIG. 1), and the second electrode 124 may be implanted closer to the LBB 8*a* (FIG. 1). The implantable leads may be implanted from the RV into the ventricular septal wall toward the LV, which may facilitate placing the first electrode 122 in close proximity to the RBB 8*b* and placing the second electrode 124 in close proximity to the LBB 8*a*. The electrodes may be used to deliver dual-bundle branch cardiac therapy (e.g., using pacing pulses) to or sense electrical activity (e.g., electrical sensing) of the RBB 8*b* and the LBB 8*a*.

One or both implantable leads may include a sheath, or lead body, and one or more conductors extending inside the sheath. In one or more embodiments described herein, the systems may include at least three electrodes, including two cathode electrodes and one anode electrode. For example, one of the leads may have two electrodes and the other lead may have one electrode. Each electrode may be operably coupled to a distal portion of a conductor that extends through the sheath of the implantable lead. A proximal portion of the conductor may be operably coupled to one or more electrical connectors at the proximal portion of the lead.

Various types of electrical connectors may be used to provide an operative connection between a medical device, which may be implantable, and one or more conductors. In one or more embodiments described herein, one example of an electrical connector has a bifurcated proximal end. Each branch may include or be described as an IS connector. In some embodiments, a further example of an electrical connector has two separate IS connectors. In one or more embodiments described herein, another example of an electrical connector has an inner conductor and two outer conductors. The inner conductor may be operably coupled to the second electrode 124, and the two outer conductors may be operably coupled to the first electrode 122 and the return electrode 126. In some embodiments, such an electrical connector may be described as an IS-4 connector.

Figure 4:
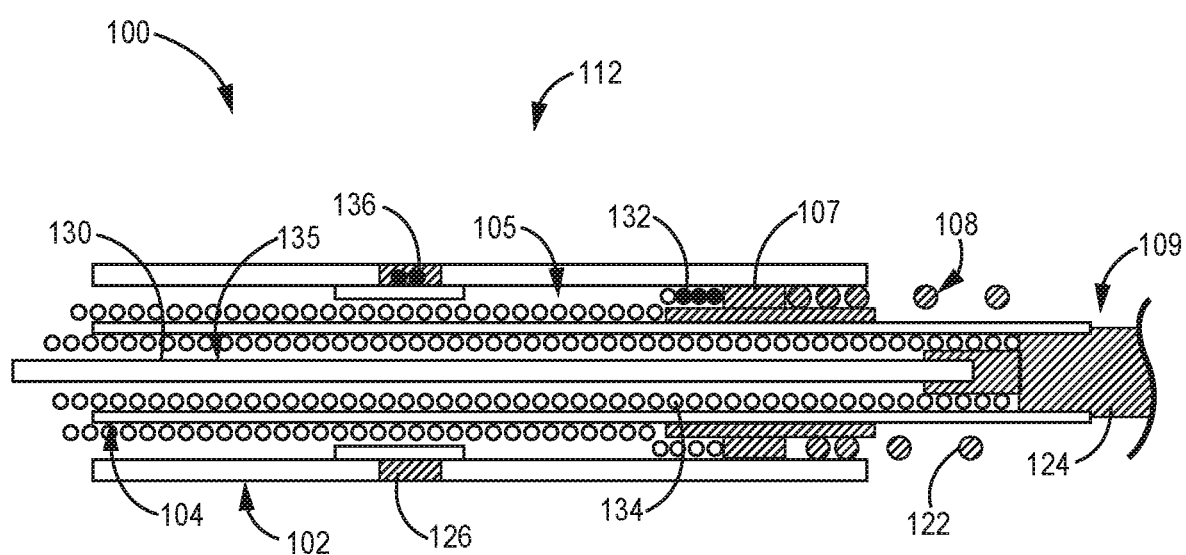
FIGS. 4-5 are schematic illustrations of distal and proximal views, respectively, of the lead-in-lead system of FIG. 2.

FIG. 4 illustrates a cross-sectional view of one example of the distal portion 112 of the lead-in-lead system 100 that includes various conductors operably coupled to the electrodes. Any suitable conductors known to one of ordinary skill in the art having the benefit of this disclosure may be used for extending through the implantable leads of the system 100.

The second implantable lead 104 may extend through the lumen 105 formed by the first implantable lead 102. The second implantable lead 104 may also define a lumen 135, and a stylet 130 may extend at least partially through the lumen to facilitate control of advancement and direction of the distal portion 112 of the system 100 during an implantation process.

The first electrode 122 is integrally formed with the fixation element 108 and coupled to the first implantable lead 102. The first electrode 122 is operably coupled to a first conductor 132 extending through the first implantable lead 102. The first conductor 132 may be disposed in the lumen 105 of the first implantable lead 102. The electrode of the conductor may extend through the sealing element 107 to establish an electrical connection between the first electrode 122 and the first conductor 132.

Also, as illustrated, the second electrode 124 is integrally formed with the fixation element 109 and coupled to the second implantable lead 104. The second electrode 124 is operably coupled to a second conductor 134 extending through the second implantable lead 104. The second conductor 134 may be disposed in the lumen 135 of the second implantable lead 104. Another conductor also may also extend through the first implantable lead 102. As illustrated, the return electrode 126 is operably coupled to a third conductor 136 extending through the lumen 105 of the first implantable lead 102. Any suitable conductor type known to one of ordinary skill in the art having the benefit of this disclosure may be used. In the illustrated embodiment, each of the conductors are coil conductors, which may facilitate flexibility of the respective lead.

In some embodiments, the distal portion of the second implantable lead 104 may include a monolithic controlled release device (MCRD). The MCRD may be positioned proximal to the second electrode 124.

Figure 5:
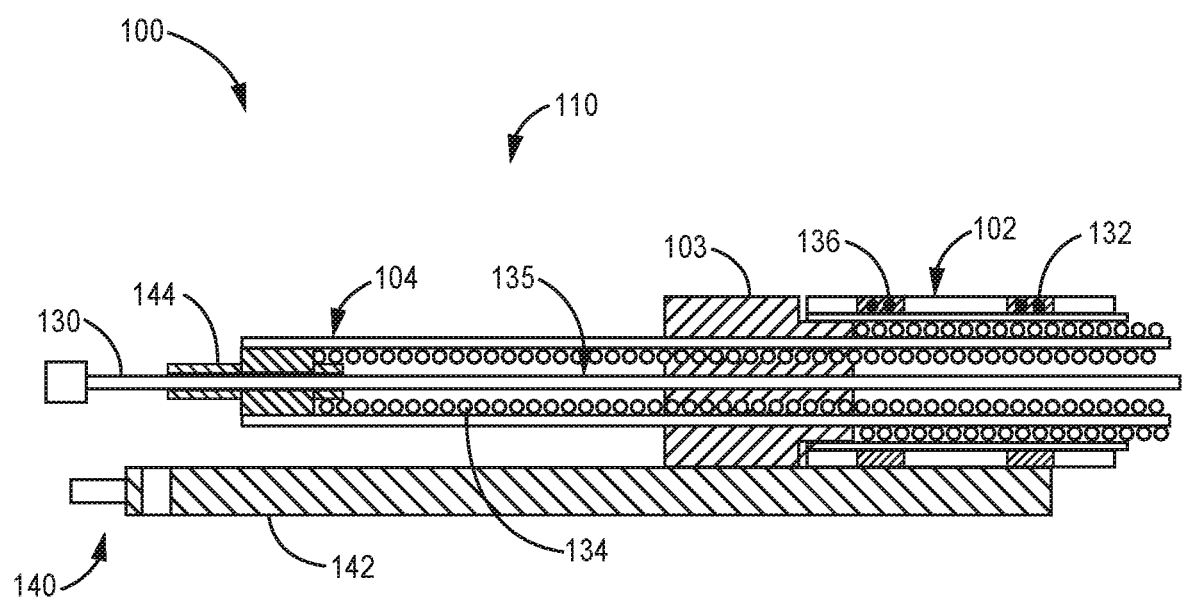

FIG. 5 illustrates a cross-sectional view of one example of the proximal portion 110 of the lead-in-lead system 100 that includes an electrical connector operably coupled to the conductors. As illustrated, an electrical connector 140 includes a first IS connector 142 and a second IS connector 144. The first conductor 132 and the third conductor 136 are operably coupled to the first IS connector 142, for example, using coil joints. The first conductor 132 may couple to a proximal contact at a proximal end or tip of the first IS connector 142, and the third conductor 136 may couple to a proximal ring contact distal to the proximal end or tip. The second conductor 134 is operably coupled to the second IS connector 144, which has at least one proximal contact. The proximal contacts of the IS connectors may be used to operably couple to the IMD 16 of FIG. 2 or FIG. 3.

In the illustrated embodiment, the first implantable lead 102 and the second implantable lead 104 are coupled by the lead fixture element 103. The stylet 130 extends through the lumen 135 of the second implantable lead 104 and through the lead fixture element 103 and may be proximally coupled to a stylet driver.

Figure 6:
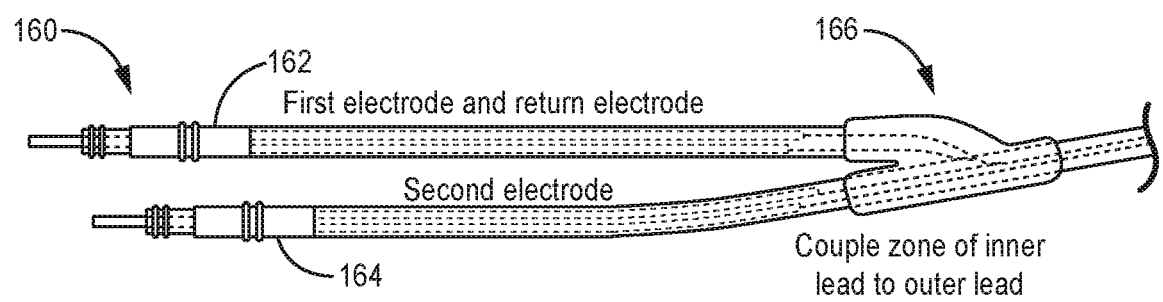
FIGS. 6-7 are schematic illustrations of electrical connectors according to the present disclosure that may be used with, for example, the lead-in-lead systems of FIGS. 2-3, to couple leads to an IMD.

FIG. 6 illustrates one example of a proximal end of a lead-in-lead system having a bifurcated electrical connector 160. The electrical connector 160 has a bifurcated proximal end. Two electrodes, such as the first electrode 122 and the return electrode 126 of FIG. 2 or FIG. 3, may be operably coupled to conductors extending through one branch 162 of the bifurcated proximal end and another electrode, such as the second electrode 124 of FIG. 2 or FIG. 3, may be operably coupled to a conductor extending through the other branch 164. Each branch may be described as an IS connector. The electrical connector 160 may include a coupling zone 166 where the electrical connector 160 may interface with the implantable leads. The electrical connector 160 may have the same or similar proximal contacts as the electrical connector 140 for coupling to the IMD 16.

Figure 7:
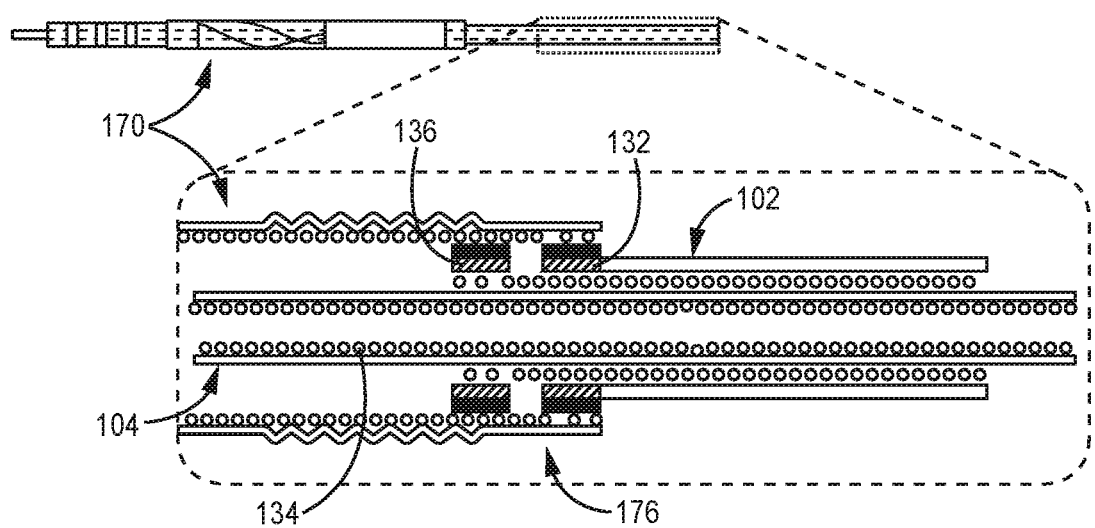

FIG. 7 illustrates a cross-sectional view of one example of a coupling zone 176 of an electrical connector 170 usable in a lead-in-lead system. The coupling zone 176 may be coupled to the first implantable lead 102 to operably couple to the first conductor 132 and the third conductor 136. The second conductor 134 of the second implantable lead 104 may extend through the coupling zone 176 and operably couple to a proximal contact at a proximal end or tip of the electrical connector 170. The first conductor 132 and the third conductor 136 may each operably couple to a proximal ring contact distal to the proximal end or tip.

Figure 8:
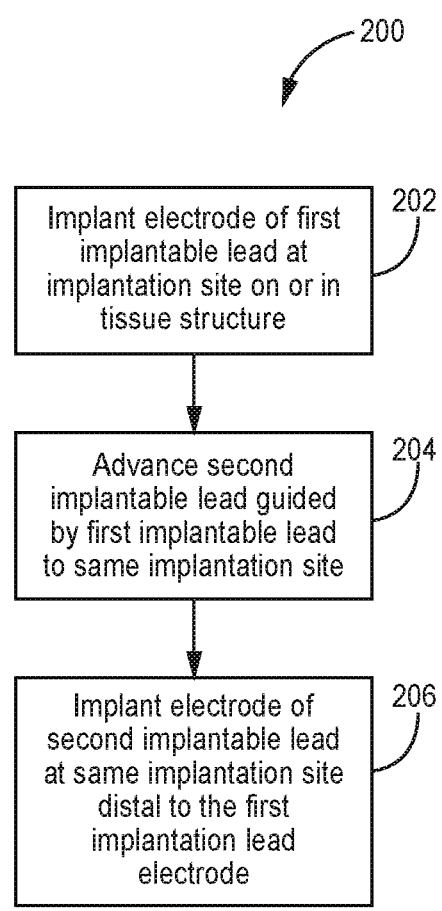
FIG. 8 is a flow diagram of one example of a method for delivering the lead-in-lead systems of FIGS. 2-3.

Various embodiments of this disclosure provide a method of delivering lead-in-lead systems for cardiac therapy to target various areas within the patient's heart. FIG. 8 illustrates one example of a method 200 for delivering a lead-in-lead system, which includes implanting a first electrode of a first implantable lead at an implantation site on or in a tissue structure of a patient's heart 202. The method 200 may also include advancing a second implantable lead having a second electrode guided by a distal portion of the first implantable lead to the same implantation site 204. The method 200 may further include implanting the second electrode at the same implantation site distal to the first implantation lead electrode 206.

The first implantable lead and the second implantable lead may be advanced concurrently toward the implantation site. In some embodiments, implanting the second electrode includes translating the second electrode relative to the first electrode after the first electrode has been implanted to allow the second electrode to be implanted at various selectable depths within the tissue structure of the patient's heart. Implanting the second electrode may also include delivering electrical pulses to test one or more depths of the first or second electrode in the tissue structure of the patient's heart.

In some embodiments, implanting the electrode of the first implantable lead may include advancing a guidewire to the implantation site. The guidewire may pierce or puncture the surface of the tissue structure. The first implantable lead may be guided over the guidewire to the implantation site. When the first implantable lead has been appropriately implanted, the guidewire may optionally be removed. The second implantable lead may be guided by a lumen of the first implantable lead or be guided over the guidewire to the implantation site. The second implantable lead may advance (e.g., drill or screw) distally into the tissue structure at the implantation site.

Figure 9:
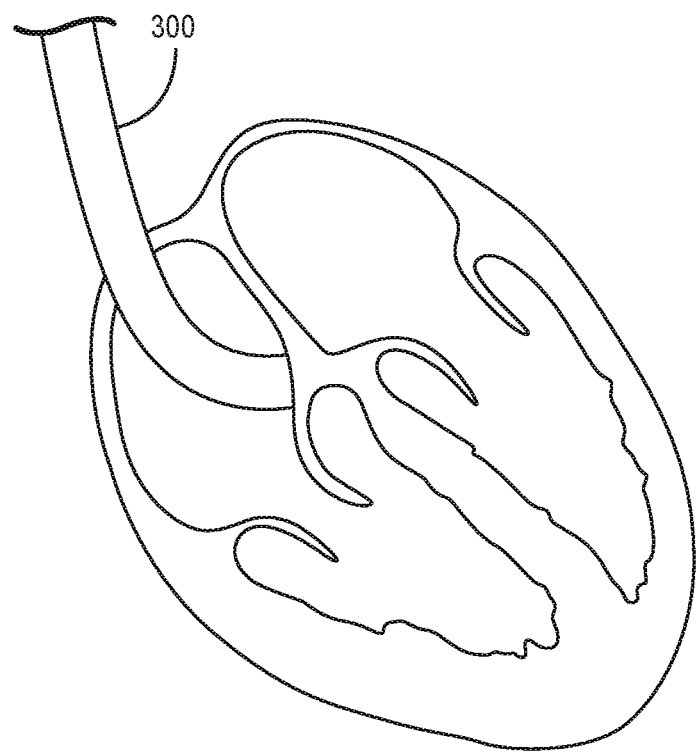
FIGS. 9-11 are schematic illustrations of various stages of delivering a lead-in-lead system for ventricle-from-atrium cardiac therapy according to the present disclosure for use with, e.g., the lead-in-lead systems of FIGS. 2-3.
Figure 10:
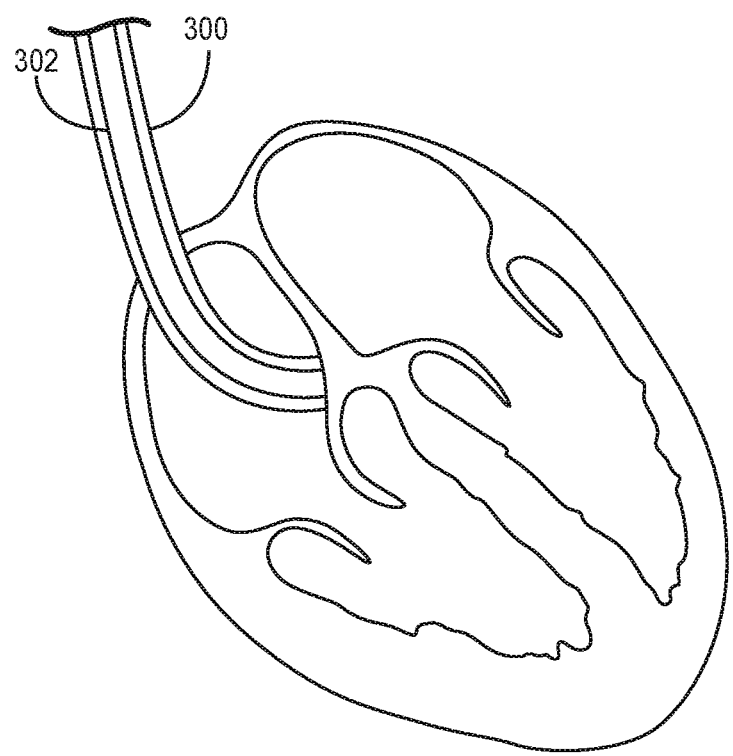
Figure 11:
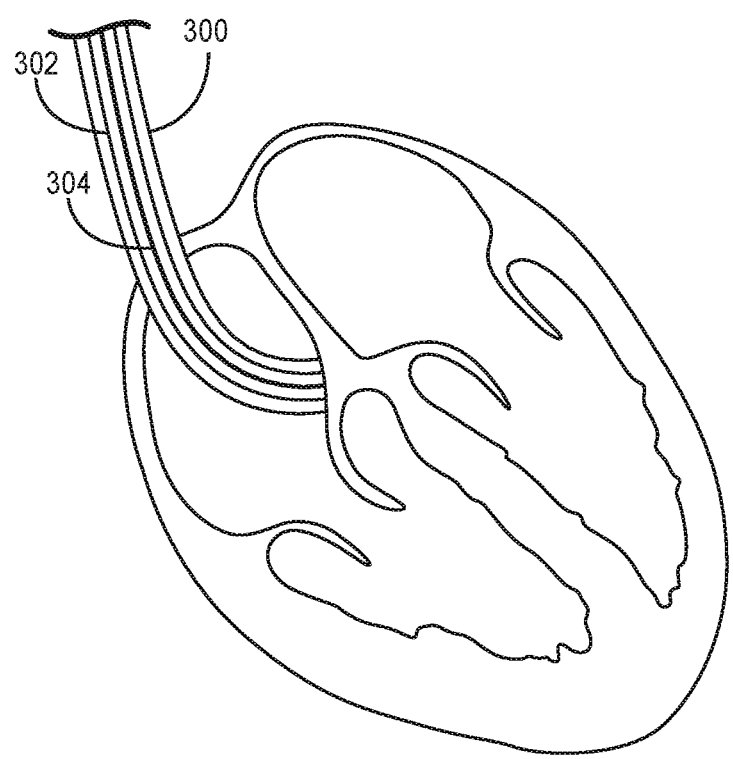
Figure 12:
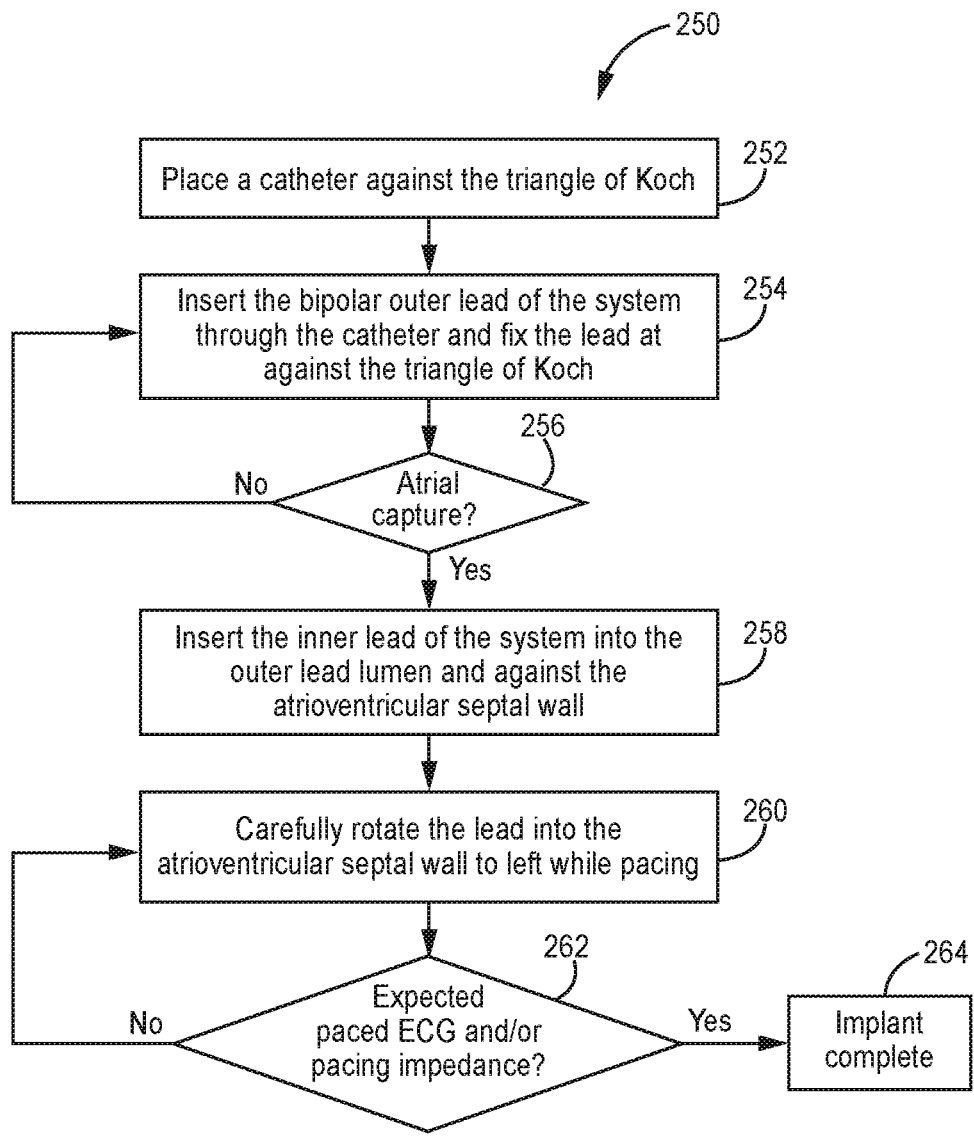
FIG. 12 is a flow diagram of one example of a particular method for delivering a lead-in-lead system for ventricle-from-atrium cardiac therapy according to the present disclosure for use with, e.g., the lead-in-lead systems of FIGS. 2-3.

FIG. 9, FIG. 10, and FIG. 11 schematically illustrate various stages of one example of carrying out the method 200, in particular, to deliver a lead-in-lead system, such as lead-in-lead system 100 (FIG. 2) or lead-in-lead system 150 (FIG. 3), for VfA cardiac therapy. In FIG. 9, a deflectable catheter 300 is advanced to and placed against the triangle of Koch in the patient's heart. In FIG. 10, a bipolar outer lead 302 (e.g., first implantable lead) of the system is implanted through the catheter 300 and is fixated at the triangle of Koch next to coronary sinus ostium. In FIG. 11, once the bipolar outer lead 302 of the system is fixed at triangle of Koch next to coronary sinus ostium, the inner lead 304 (e.g., second implantable lead) of the system is implanted though the outer lead lumen and fixated into the atrioventricular septal wall by rotating the inner lead body. FIG. 12 is a flowchart illustrating one example of a particular method 250 for carrying out the method 200, in particular, to deliver a lead-in-lead system for VfA cardiac therapy. The method 250 may include placing a catheter against the triangle of Koch 252 (see FIG. 9). The method 250 may also include inserting the bipolar outer lead of the system through the catheter and fixing the lead against the triangle of Koch 254 (see FIG. 10). The method 250 may determine whether the bipolar outer lead captures the atrium 256, in particular, the right atrium. If the atrium is not captured, the method 250 may return to inserting the bipolar lead 254 into a new location in the triangle of Koch. If the atrium is captured, the method 250 may include inserting the inner lead of the system into the outer lead lumen and placing the inner lead against the atrioventricular septal wall 258 (see FIG. 11). The method 250 may also include carefully rotating the inner lead into the atrioventricular septal wall toward the left side of the patient's heart while performing test pacing 260 (see FIG. 11).

The method 250 may further determine whether an expected paced ECG or pacing impedance is observed during the inner lead rotating process 262. If the expected ECG or pacing impedance is observed, the method 250 may determine that implantation is complete 264. For example, the leads may then be coupled to an IMD. Otherwise, the method 250 may continue to rotate the inner lead while test pacing 260.

Figure 13:
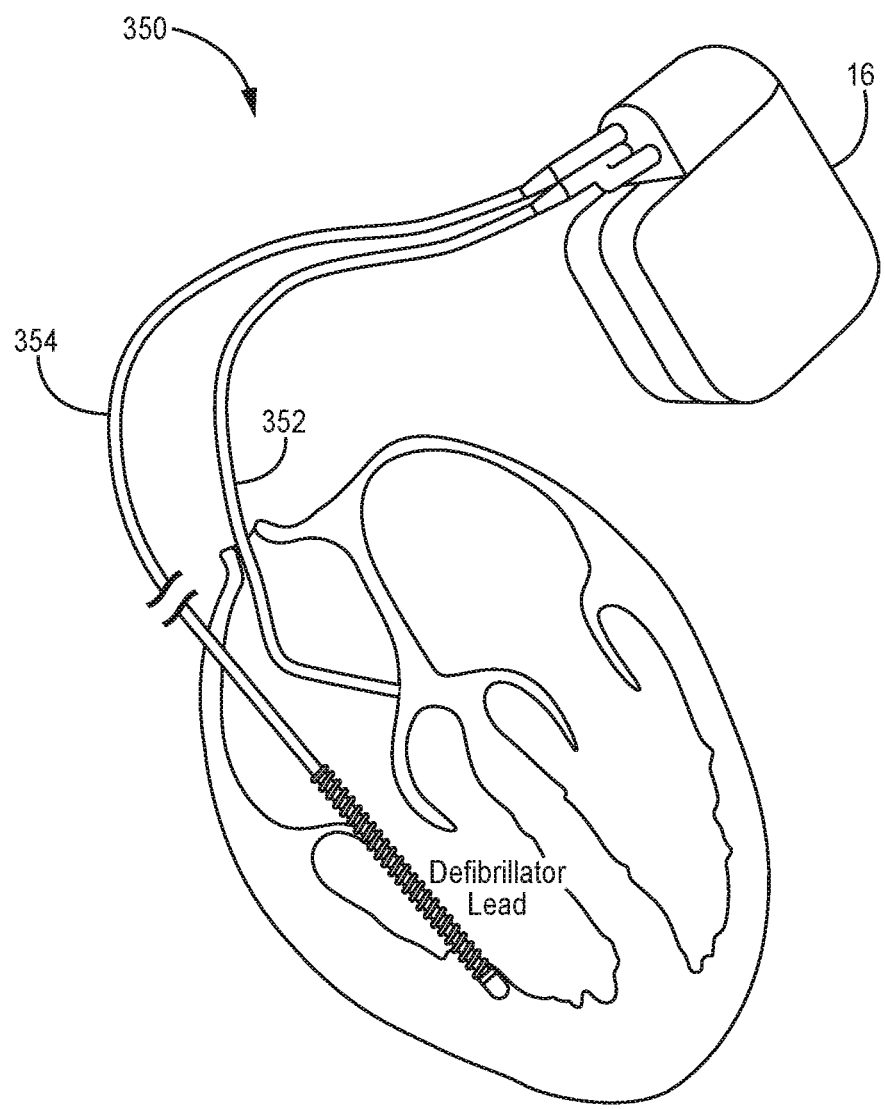
FIG. 13 is a schematic illustration of an environment for a lead-in-lead system, such as one of the lead-in-lead systems of FIGS. 2-3, for ventricle-from-atrium cardiac therapy with a defibrillator lead according to the present disclosure.

FIG. 13 illustrates a system 350 that may utilize a lead-in-lead system 352, which may be lead-in-lead system 100 (FIG. 2) or lead-in-lead system 150 (FIG. 3), and a defibrillator lead 354 both coupled to the IMD 16 to provide cardiac therapy that may include VfA pacing (e.g., DDDR-type pacing) and defibrillation. The defibrillator lead 354 may be implanted, for example, in the RV of the patient's heart.

Figure 14:
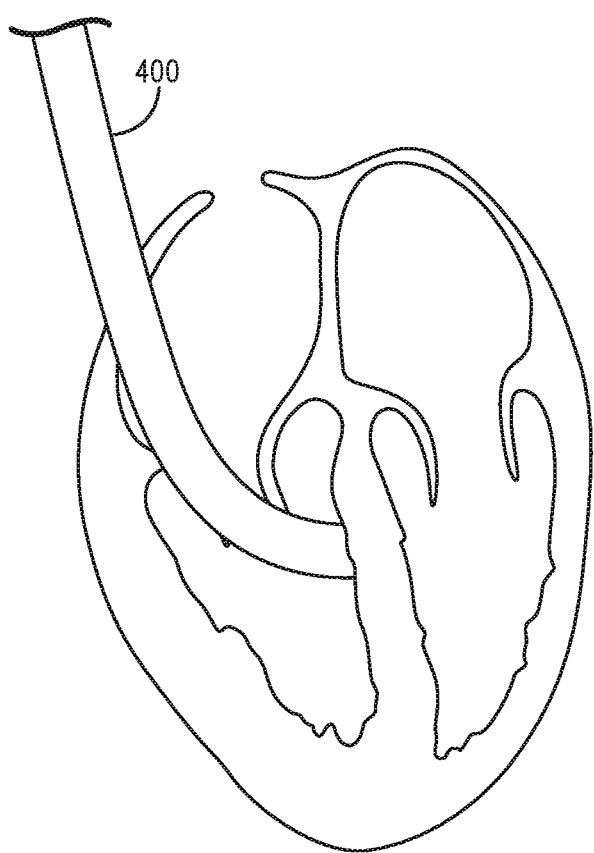
FIGS. 14-16 are schematic illustrations of various stages of delivering a lead-in-lead system for dual bundle-branch cardiac therapy according to the present disclosure for use with, e.g., the lead-in-lead systems of FIGS. 2-3.
Figure 15:
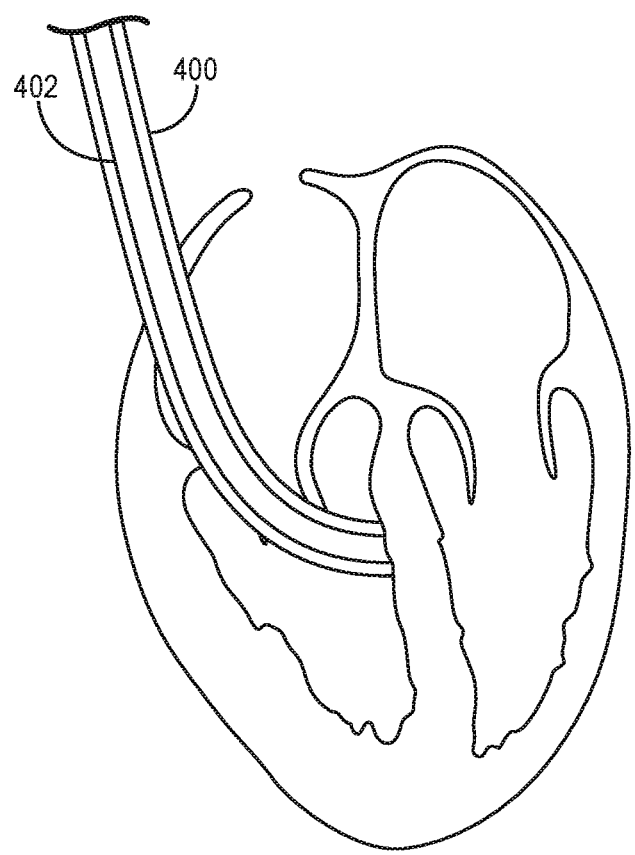
Figure 16:
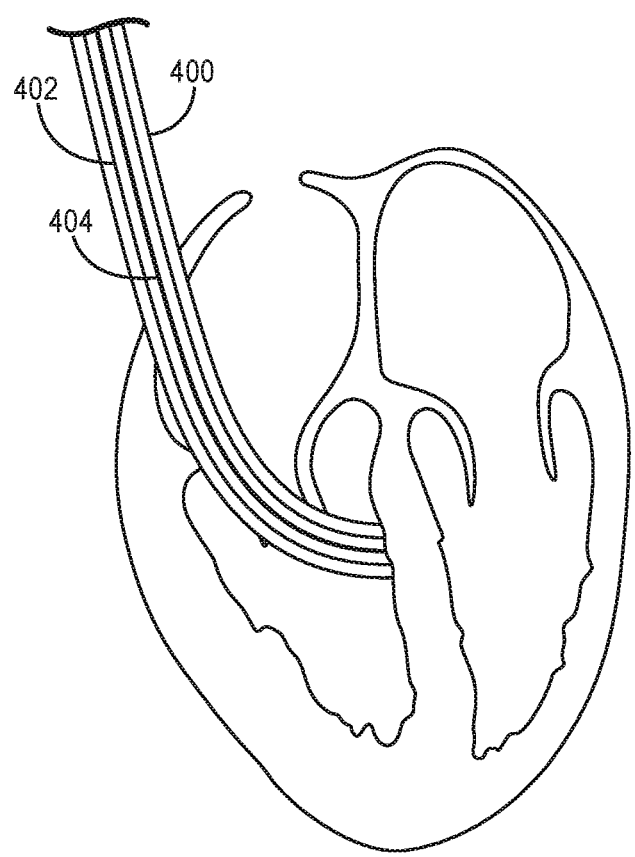

FIG. 14, FIG. 15, and FIG. 16 schematically illustrate various stages of one example of carrying out method 200, in particular, to deliver a lead-in-lead system, such as lead-in-lead system 100 (FIG. 2) or lead-in-lead system 150 (FIG. 3), for bi-cardiac conduction branch pacing or, in other words, dual bundle-branch cardiac therapy. In FIG. 14, a deflectable catheter 400 is advanced to and placed against the RV high septal wall under the antero-septal tricuspid commissure, for example, about 1 to 3 centimeters (cm) below. In FIG. 15, a bipolar outer lead 402 (e.g., first implantable lead) of the system is implanted through the catheter 400 and is fixated at the right ventricular septal wall under the antero-septal tricuspid commissure, for example, about 1 to 3 cm below. In FIG. 16, once the bipolar outer lead 402 of the system is fixed at the right ventricular septal wall, the inner lead 404 (e.g., second implantable lead) of the system is implanted though the outer lead lumen and fixated into septal wall to left high septal wall (e.g., at the bundle branches) by rotating the inner lead body.

Figure 17:
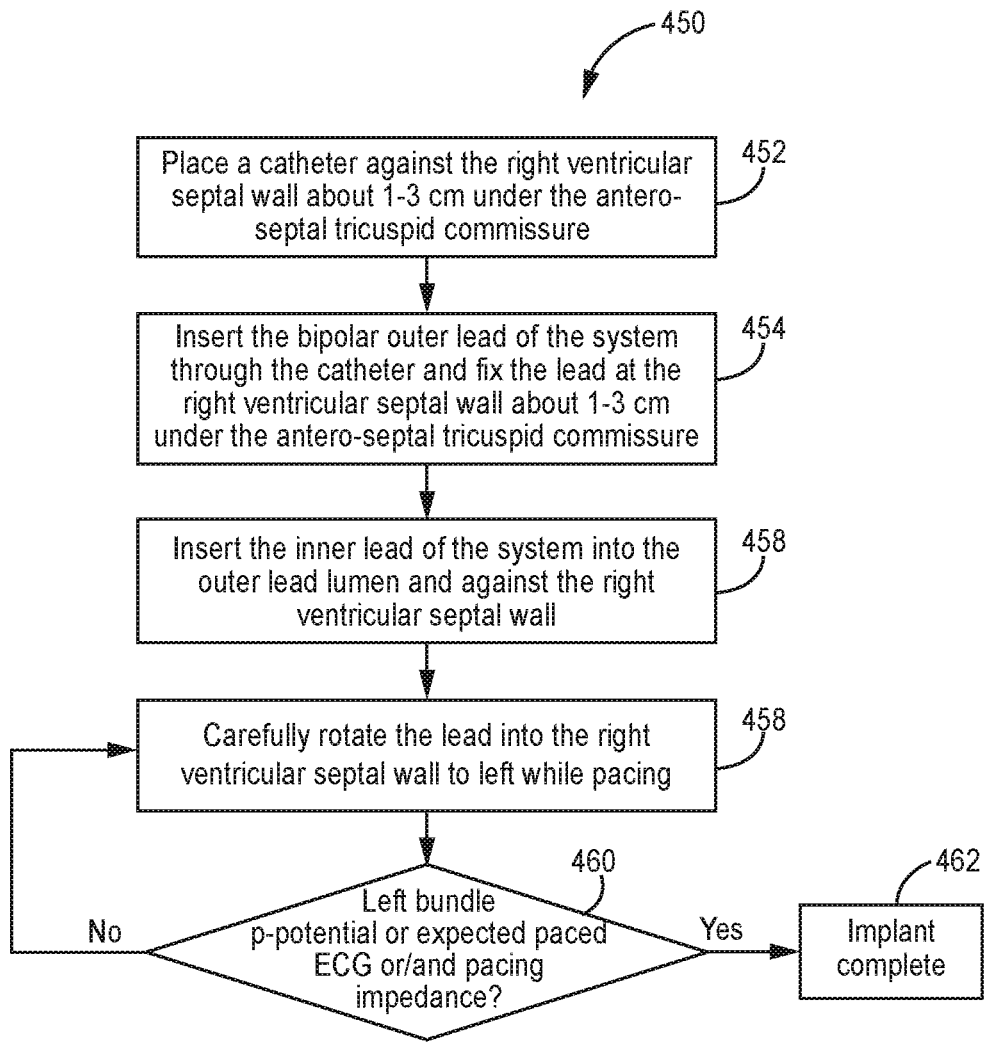
FIG. 17 is a flow diagram of one example of a particular method for delivering a lead-in-lead system for dual bundle-branch cardiac therapy according to the present disclosure for use with, e.g., the lead-in-lead systems of FIGS. 2-3.

FIG. 17 is a flowchart illustrating on example of a particular method 450 for carrying out the method 200, in particular, to deliver a lead-in-lead system, such as lead-in-lead system 100 (FIG. 2) or lead-in-lead system 150 (FIG. 3), for dual bundle-branch cardiac therapy. The method 450 may include placing the catheter against the right ventricular septal wall under the antero-septal tricuspid commissure 452 (see FIG. 14), for example, about 1 to 3 cm below. The method 450 may also include inserting the bipolar outer lead of the system through the catheter and fixing the bipolar outer lead at the right ventricular septal wall under the antero-septal tricuspid commissure 454 (see FIG. 15), for example, about 1 to 3 cm below.

The method 450 may further include inserting the inner lead of the system into the outer lead lumen and placing the inner lead against the right ventricular septal wall 456 (see FIG. 16). The method 450 may include carefully rotating the inner lead into the right ventricular septal wall toward the left side of the patient's heart while performing test pacing 458 (see FIG. 16).

The method 450 may include determining whether a left bundle Purkinje potential from an EGM using the second electrode or an expected pacing impedance is observed 460. If the left bundle Purkinje potential or pacing impedance is observed, the method 450 may determine that implantation is complete 462. For example, the leads may then be coupled to an IMD. Otherwise, the method 450 may continue to rotate the inner lead while test pacing 458.

Optionally, the method 450 also include rotating the bipolar outer lead and performing test pacing until a right bundle Purkinje-potential, expected EGM, or pacing impedance is observed.

Figure 18:
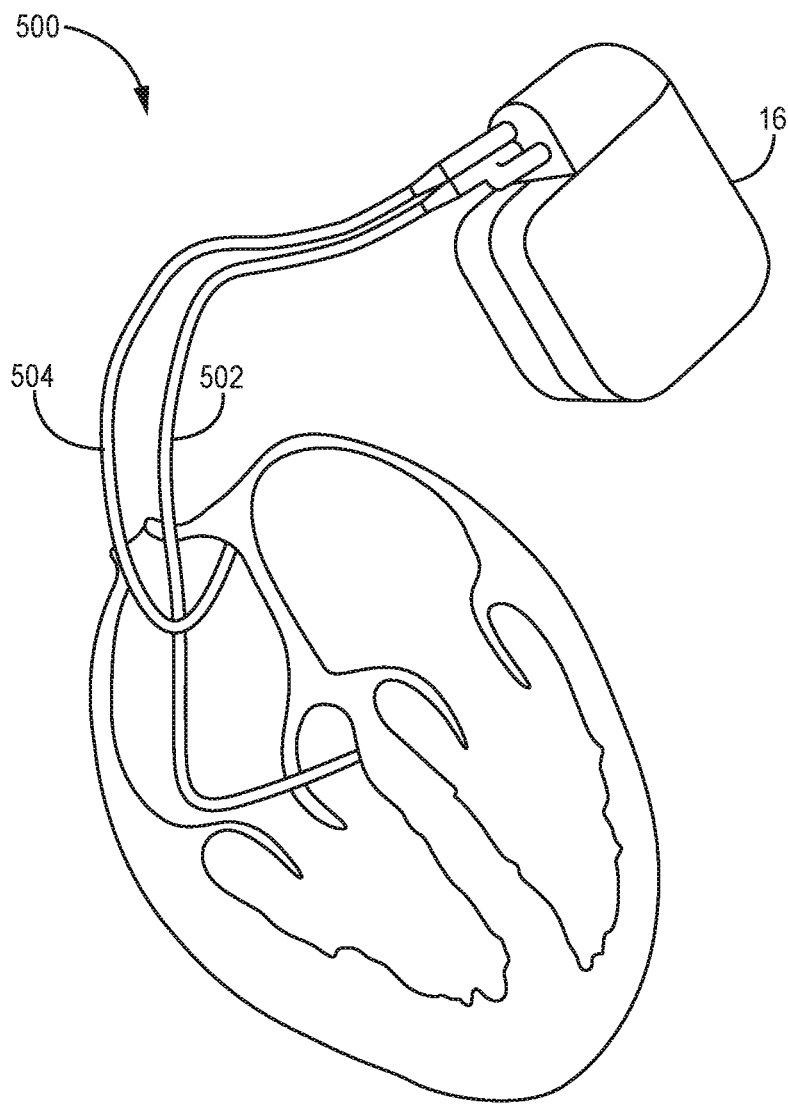
FIG. 18 is a schematic illustration of one example of a lead-in-lead system, such as one of the lead-in-lead systems of FIGS. 2-3, for dual bundle-branch cardiac therapy used with an atrial lead according to the present disclosure.

FIG. 18 illustrates a system 500 that may utilize a lead-in-lead system 502, which may be lead-in-lead system 100 (FIG. 2) or lead-in-lead system 150 (FIG. 3), and an atrial lead 504 both coupled to the IMD 16 to provide cardiac therapy that may include dual bundle-branch pacing (e.g., DDDR-type pacing). The atrial lead 504 may be planted in the RA of the patient's heart.

Figure 19:
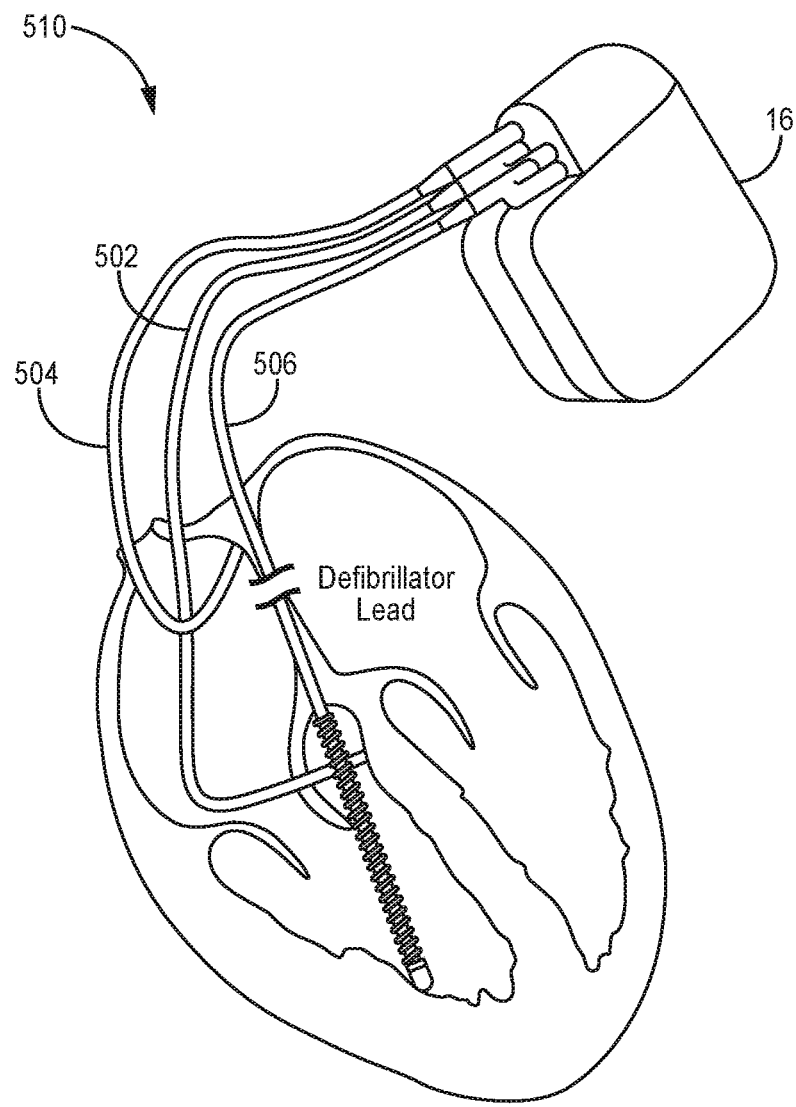
FIG. 19 is a schematic illustration of one example of a lead-in-lead system, such as one of the lead-in-lead systems of FIGS. 2-3, for dual bundle-branch cardiac therapy used with an atrial lead and a defibrillator lead according to the present disclosure.

FIG. 19 illustrates a system 510 that may utilize a lead-in-lead system 502, which may be lead-in-lead system 100 (FIG. 2) or lead-in-lead system 150 (FIG. 3), an atrial lead 504, and a defibrillator lead 506 each coupled to the IMD 16 to provide cardiac therapy that may include dual bundle-branch pacing (e.g., DDDR-type pacing) and defibrillation. The defibrillator lead 506 may be implanted, for example, in the RV of the patient's heart.

Figure 20:
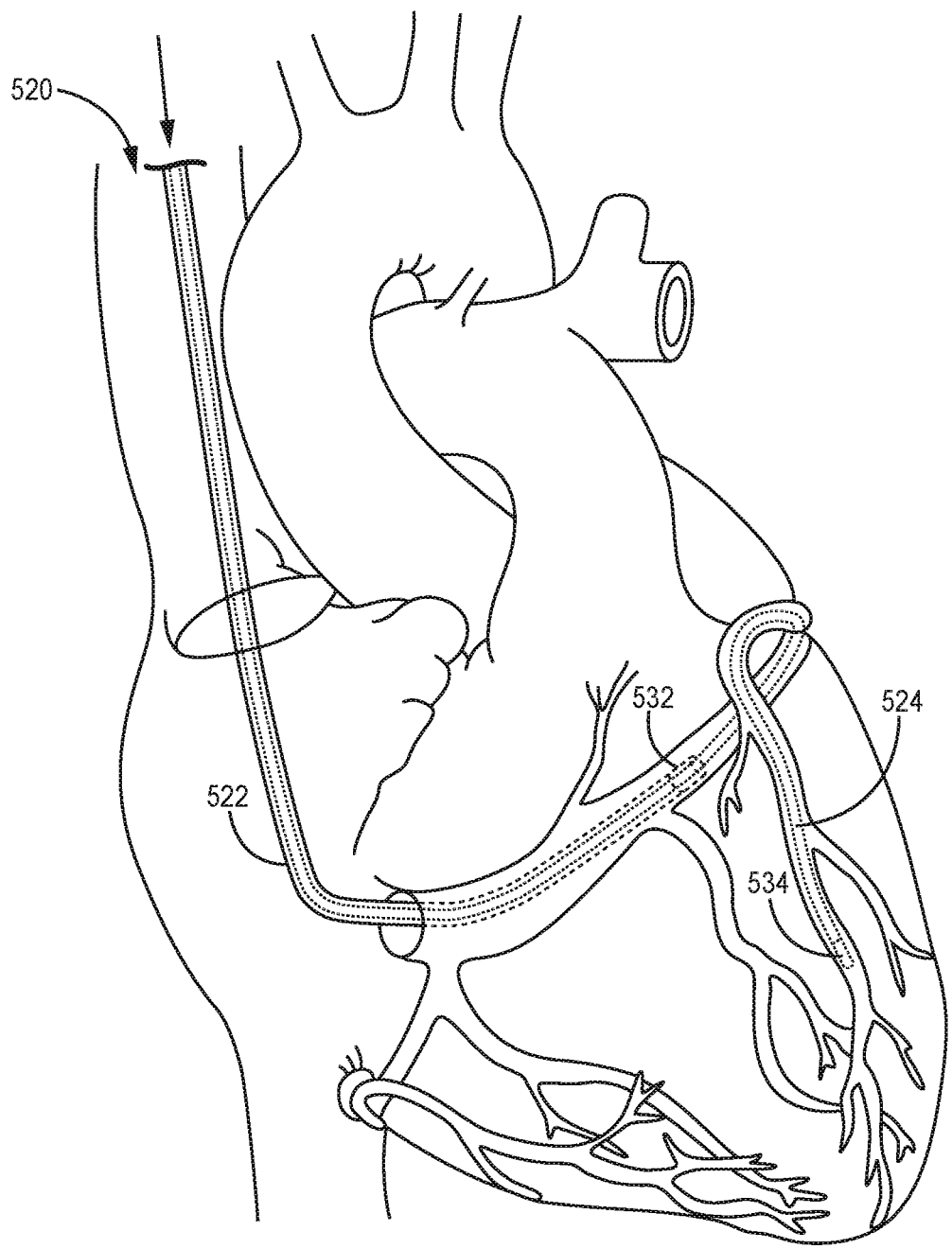
FIGS. 20-22 are schematic illustrations of examples of lead-in-lead systems, such as the lead-in-lead systems of FIGS. 2-3, for left-side cardiac therapy in the coronary vasculature according to the present disclosure.

Various lead-in-lead systems may also be used to access the coronary vasculature, such as the coronary sinus and coronary veins, for left-side cardiac therapy. FIG. 20 shows one example of a system 520, which may be similar to or the same as lead-in-lead system 100 (FIG. 2) or lead-in-lead system 150 (FIG. 3), for left-side cardiac therapy. The system 520 includes a first implantable lead 522 and a second implantable lead 524. A first electrode 532 may be coupled to a distal portion of the first implantable lead 522 (e.g., outer lead) and implanted in a coronary vein (e.g., great cardiac vein). The second implantable lead 524 (e.g., inner lead) may extend distally from the first implantable lead 522. A second electrode 534 may be coupled to a distal portion of the second implantable lead 524. The second electrode 534 is positioned distally from the first electrode 532 (e.g., further along the great cardiac vein). The first electrode 532 may capture the LA of the patient's heart, and the second electrode 534 may capture the LV of the patient's heart.

The system 520 may be implanted using any suitable technique. One example of an implantation method may include implanting the first implantable lead 522 to implant the first electrode 532 at a first implantation site in the coronary sinus or a coronary vein of a patient's heart. The method may also include advancing the second implantable lead 524 having the second electrode 534 guided by a distal portion of the first implantable lead 522 to a second implantation site distal to the first electrode 532 in a coronary vein of the patient's heart. The method may further include implanting the second electrode 534 at the second implantation site.

Figure 21:
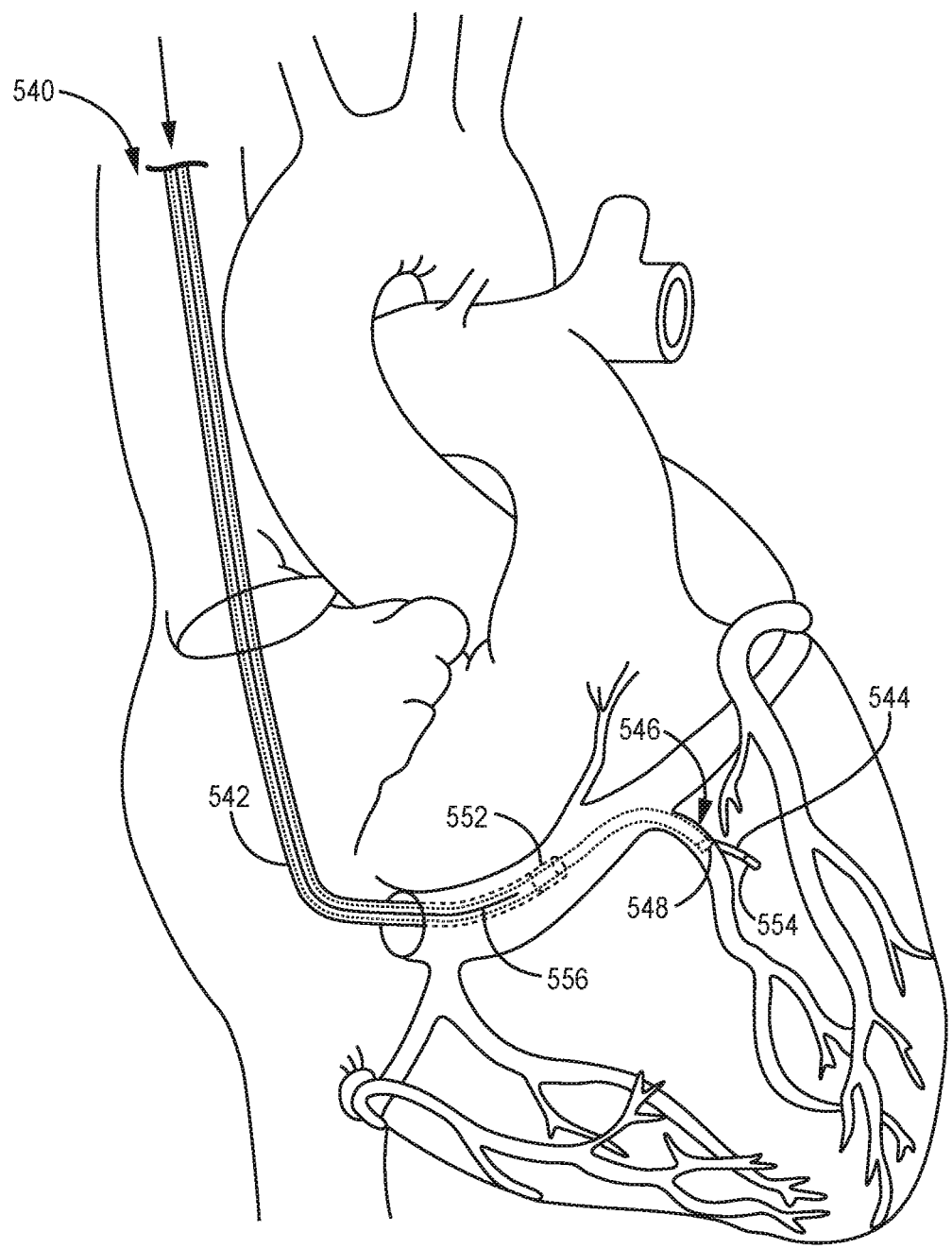

FIG. 21 shows one example of a system 540, which may be similar to or the same as lead-in-lead system 100 (FIG. 2) or lead-in-lead system 150 (FIG. 3), for left-side cardiac therapy. The system 540 includes a first implantable lead 542 and a second implantable lead 544. A first electrode 552 may be coupled proximal to a distal portion 546 of the first implantable lead 542 (e.g., outer lead) and implanted in the coronary sinus. The second implantable lead 544 (e.g., inner lead) may extend distally from the first implantable lead 542 and through a puncture 548, such as a micropuncture, in a coronary vessel wall (e.g., the wall of the middle cardiac vein). A second electrode 554 may be coupled to a distal portion of the second implantable lead 544 and may extend into the pericardial cavity of the patient's heart and be implanted into the myocardium, such as the LV myocardium, through the epicardium. The first electrode 552 may capture the LA of the patient's heart, and the second electrode 554 may capture the LV of the patient's heart.

In particular, the second implantable lead 544 may extend through the puncture 548 from the vessel into the pericardial cavity, which extends between the epicardium and the pericardium of the patient's heart. The distal end of the second implantable lead 544 may be positioned at various locations within the pericardial cavity to access different implantation sites in the myocardium, such as the LV myocardium, through the epicardium that are outside of the coronary vasculature.

A guidewire 556 may be used to form the puncture in the vessel wall and thereafter retracted from the system 540. A structure of the first implantable lead 542, such as the distal portion 546, may be advanced to the puncture 548 and positioned adjacent to the puncture to seal the puncture.

The system 540 may be implanted using any suitable technique. One example of an implantation method may include advancing the second electrode 554 of the second implantable lead 544 guided by the distal portion 546 of the first implantable lead 542 to a location in the coronary sinus or a coronary vein of a patient's heart. The method may also include implanting the first electrode 552 at a first implantation site in the coronary sinus or a coronary vein of the patient's heart. The method may also include puncturing through a vessel wall at the location in the coronary sinus or the coronary vein into the pericardial cavity of the patient's heart, for example, using the guidewire 556. The method may also include advancing the second implantable lead 544 through the puncture 548 in the vessel wall into the pericardial cavity. Further, the method may include implanting the second electrode 554 into the epicardium and myocardium of the patient's heart from the pericardial cavity at a second implantation site distal to the first implantation site. The second implantation site may be in the myocardium of the patient's heart outside of the coronary sinus or the coronary veins. In some embodiments, the first electrode 552 is implanted after the second electrode 554 is implanted, which may facilitate sealing of the puncture 548 by the first implantable lead 542.

Figure 22:
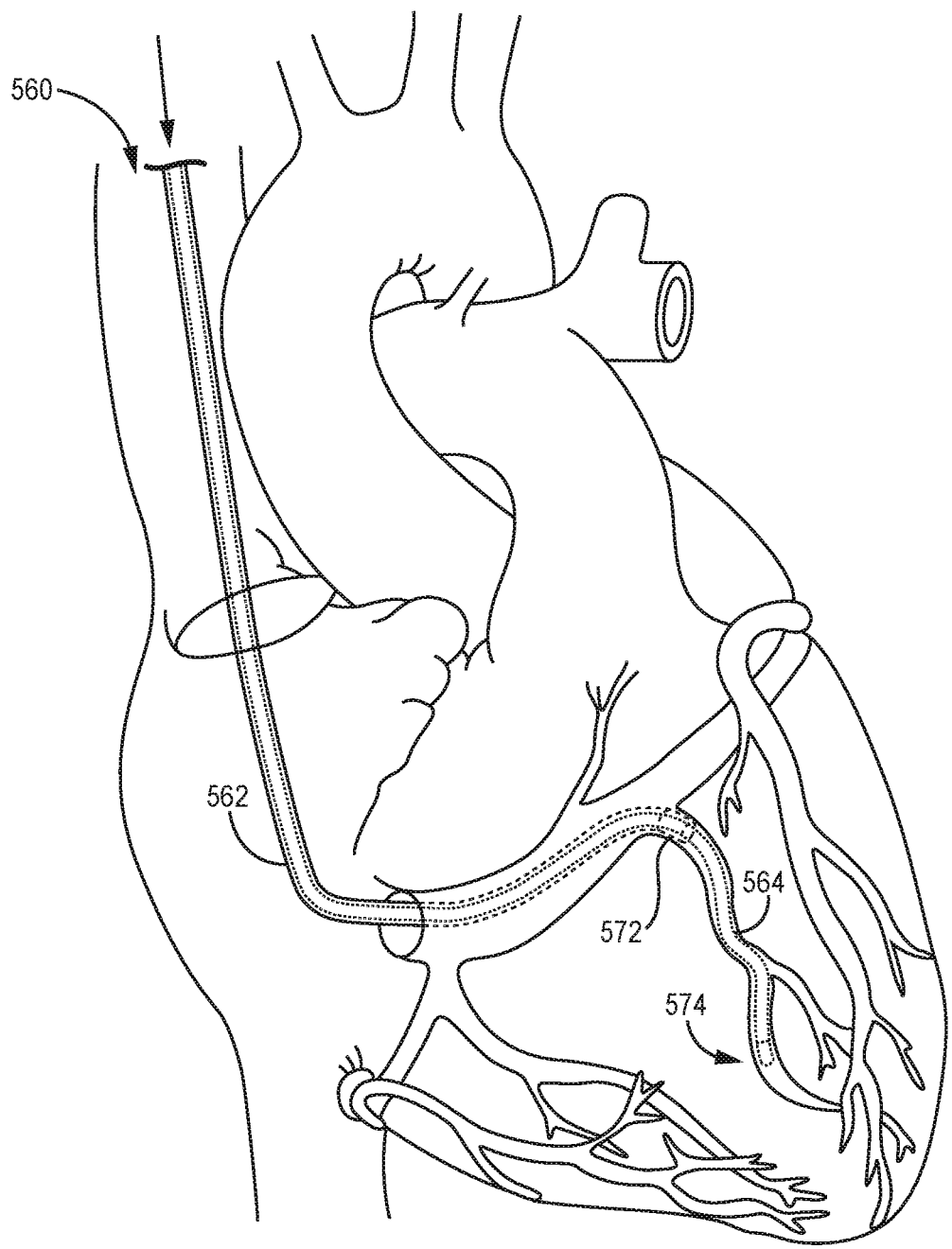

FIG. 22 shows one example of a system 560, which may be similar to or the same as lead-in-lead system 100 (FIG. 2) or lead-in-lead system 150 (FIG. 3), for left-side cardiac therapy. The system 560 includes a first implantable lead 562 and a second implantable lead 564. A first electrode 572 may be coupled to a distal portion of the first implantable lead 562 (e.g., outer lead) and implanted in the middle cardiac vein (e.g., a coronary vein). The second implantable lead 564 (e.g., inner lead) may extend distally from the first implantable lead 562. A second electrode 574 may be coupled to a distal portion of the second implantable lead 564 and may extend into the myocardium of the patient's heart, such as the LV myocardium. The first electrode 572 may capture the LA of the patient's heart, and the second electrode 574 may capture the LV of the patient's heart.

FIG. 23 shows one example of the IMD 16 including a connector receptacle 40 configured to receive a lead or lead connector from a lead-in-lead system, such as lead-in-lead system 100 (FIG. 2) or lead-in-lead system 150 (FIG. 3), a therapy delivery circuit 42 operably coupled to the connector receptacle, a sensing circuit 44 operably coupled to the connector receptacle, and a controller 46 operably coupled to the therapy delivery circuit and the sensing circuit.

The therapy delivery circuit 42 is configured to deliver cardiac therapy to the patient's heart through one or more operably connected electrodes, for example, electrically connected via the connector receptacle 40. The sensing circuit 44 is configured to sense electrical activity of the patient's heart using one or more operably connected electrodes, for example electrically connected via the connector receptacle 40. The electrodes operably coupled to the sensing circuit 44 may or may not include some or all of the electrodes that are also operably coupled to the therapy delivery circuit 42. The sensing circuit 44 may monitor electrical activity of the patient's heart, for example, using electrical signals, such as electrocardiogram (ECG) signals or electrogram (EGM) signals.

The controller 56 may have processing circuitry operably coupled to the therapy delivery circuit 42 and the sensing circuit 44. The controller 46 may be used to carry out various functionality of the IMD 16 coupled to the lead-in-lead systems described herein, such as lead-in-lead system 100 (FIG. 2) or lead-in-lead system 150 (FIG. 3).

Processing circuitry may include any one or more of a microprocessor, a controller, a digital signal processor (DSP), an application specific integrated circuit (ASIC), a field-programmable gate array (FPGA), or equivalent discrete or integrated logic circuitry. In some examples, processing circuitry may include multiple components, such as any combination of one or more microprocessors, one or more controllers, one or more DSPs, one or more ASICs, or one or more FPGAs, as well as other discrete or integrated logic circuitry. The functions attributed to the processing circuitry of the controller herein may be embodied as software, firmware, hardware or any combination thereof. The controller may control the therapy delivery circuit to deliver stimulation therapy to the patient's heart according to a selected one or more of therapy programs, which may be stored in a memory. Specifically, the controller may control the therapy delivery circuit to deliver electrical pulses with amplitudes, pulse widths, frequency, or electrode polarities specified by the selected one or more therapy programs.

The controller 46 may include memory. Non-limiting examples of memory may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

Illustrative Aspects Lead-in-Lead Systems and Methods

While the present disclosure is not so limited, an appreciation of various aspects of the disclosure will be gained through a discussion of the specific illustrative Lead-in-Lead Systems and Methods thereof provided below. Various modifications of the examples and illustrative Lead-in-Lead Systems and Methods, as well as additional features of the disclosure, will become apparent herein.

In illustrative aspect A1, a system includes a first implantable lead having a distal portion and a first electrode coupled to the distal portion of the first implantable lead. The first electrode is configured to be implanted at an implantation site on or in a tissue structure of a patient's heart. The system also includes a second implantable lead having a distal portion and a second electrode coupled to the distal portion of the second implantable lead. The second electrode is configured to be implanted at the implantation site distal to the first electrode within the tissue structure of the patient's heart. The distal portion of the second implantable lead is guided by the distal portion of the first implantable lead to the implantation site.

In illustrative aspect A2, a system includes the system of any A aspect, wherein the second electrode is translatable relative to the first electrode after the first electrode has been implanted to allow the second electrode to be implanted at various depths within the tissue structure of the patient's heart.

In illustrative aspect A3, a system includes the system of any A aspect, wherein the first or second electrode is configured to deliver electrical pulses to test one or more depths of the respective electrode in the tissue structure of the patient's heart.

In illustrative aspect A4, a system includes the system of any A aspect, wherein the second implantable lead is freely rotatable relative to the first implantable lead to facilitate implantation.

In illustrative aspect A5, a system includes the system of any A aspect, wherein the second implantable lead is at least partially receivable into a lumen of the first implantable lead to guide the distal portion of the second implantable lead to the implantation site.

In illustrative aspect A6, a system includes the system of any A aspect, wherein the implantation site is the triangle of Koch region in the atrioventricular wall of the patient's heart and the tissue structure is between the right atrium and left ventricle of the patient's heart.

In illustrative aspect A7, a system includes the system of aspect A6, wherein the first electrode is implantable in the right atrium (RA) of the patient's heart to deliver cardiac therapy to or sense electrical activity of the RA of the patient's heart and the second electrode is implantable from the triangle of Koch region of the RA of the patient's heart to deliver cardiac therapy to or sense electrical activity of the left ventricle (LV) in the basal region, septal region, or basal-septal region of the left ventricular myocardium of the patient's heart.

In illustrative aspect A8, a system includes the system of any aspect A1-A5, wherein the implantation site is the ventricular septal wall of the patient's heart and the tissue structure is between the right ventricle and the left ventricle of the patient's heart.

In illustrative aspect A9, a system includes the system of any A aspect, wherein the first electrode is implantable closer to a first bundle branch of the cardiac conduction system of the patient's heart than the second electrode and the second electrode is implantable closer to a second bundle branch of the cardiac conduction system of the patient's heart than the first electrode.

In illustrative aspect A10, a system includes the system of any A aspect, wherein the first electrode is implantable from the right ventricle (RV) of the patient's heart to deliver cardiac therapy to or sense electrical activity of the right bundle branch of the cardiac conduction system of the patient's heart and the second electrode is implantable from the RV of the patient's heart to deliver cardiac therapy to or sense electrical activity of the left bundle branch of the cardiac conduction system of the patient's heart.

In illustrative aspect A11, a system includes the system of any A aspect, wherein the first implantable lead includes a first fixation element formed integrally or separately from the first electrode.

In illustrative aspect A12, a system includes the system of any A aspect, wherein the second implantable lead includes a second fixation element formed integrally or separately from the second electrode.

In illustrative aspect A13, a system includes the system of aspect A12, wherein the second fixation element includes a drill or helix structure.

In illustrative aspect A14, a system includes the system of any A aspect, wherein the second electrode is configured to pierce into the tissue structure of the patient's heart.

In illustrative aspect A15, a system includes the system of any A aspect, further including a guide wire at least partially receivable into a lumen of the second implantable lead to pierce into the tissue structure of the patient's heart.

In illustrative aspect A16, a system includes the system of any A aspect, further including a lead fixture element to mechanically couple to the first implantable lead and the second implantable lead.

In illustrative aspect A17, a system includes the system of any A aspect, further including an electrical connector coupled to one or both of the first and second electrodes.

In illustrative aspect A18, a system includes the system of aspect A17, wherein the electrical connector includes a bifurcated proximal end.

In illustrative aspect A19, a system includes the system of aspect A17, wherein the electrical connector includes an inner conductor and two outer conductors.

In illustrative aspect B1, a method includes implanting a first electrode of a first implantable lead at an implantation site on or in a tissue structure of a patient's heart. The method also includes advancing a second implantable lead having a second electrode guided by a distal portion of the first implantable lead to the implantation site within the tissue structure of the patient's heart. The method further includes implanting the second electrode at the implantation site distal to the first electrode within the tissue structure of the patient's heart.

In illustrative aspect B2, a method includes the method of any B aspect, further including translating the second electrode relative to the first electrode after the first electrode has been implanted to allow the second electrode to be implanted at various selectable depths within the tissue structure of the patient's heart.

In illustrative aspect B3, a method includes the method of any B aspect, further including delivering electrical pulses to test one or more depths of the first or second electrode in the tissue structure of the patient's heart.

In illustrative aspect B4, a method includes the method of any B aspect, wherein the first implantable lead and the second implantable lead are advanced concurrently toward the implantation site.

In illustrative aspect B5, a method includes the method of any B aspect, further including advancing a guide wire to the implantation site, wherein the first implantable lead is guided over the guide wire to the implantation site.

In illustrative aspect C1, an implantable medical device includes a plurality of electrodes. The plurality of electrodes includes a first electrode configured to be implanted at an implantation site on or in a tissue structure of a patient's heart. The plurality of electrodes also includes a second electrode configured to be implanted at the implantation site distal to the first electrode within the tissue structure of the patient's heart. The second electrode is translatable relative to the first electrode after the first electrode has been implanted to allow the second electrode to be implanted at various depths within the tissue structure of the patient's heart. The implantable medical device also includes a therapy delivery circuit operably coupled to the plurality of electrodes to deliver cardiac therapy to the patient's heart, and a sensing circuit operably coupled to the plurality of electrodes to sense electrical activity of the patient's heart. The implantable medical device further includes a controller having processing circuitry operably coupled to the therapy delivery circuit and the sensing circuit. The controller is configured to provide electrical pulses to at least the second electrode to test one or more depths of the second electrode within the tissue structure of the patient's heart.

In illustrative aspect C2, a device includes the device of any C aspect, wherein the second electrode is translatable relative to the first electrode after the first electrode has been implanted to allow the second electrode to be implanted at various selectable depths within the tissue structure of the patient's heart.

In illustrative aspect C3, a device includes the device of any C aspect, wherein the second electrode is configured to deliver electrical pulses from the therapy delivery circuit to test one or more depths of the first electrode in the tissue structure of the patient's heart.

In illustrative aspect C4, a device includes the device of any C aspect, wherein the first electrode and the second electrode are integrated into a single lead assembly configured to concurrently advance the first electrode and the second electrode toward the implantation site.

Thus, various aspects of the LEAD-IN-LEAD SYSTEMS AND METHODS FOR CARDIAC THERAPY are disclosed. Although reference is made herein to the accompanying set of drawings that form part of this disclosure, one of at least ordinary skill in the art will appreciate that various adaptations and modifications of the Lead-in-Lead Systems and Methods thereof is described herein are within, or do not depart from, the scope of this disclosure. For example, aspects of the Lead-in-Lead Systems and Methods thereof are described herein may be combined in a variety of ways with each other. Therefore, it is to be understood that, within the scope of the appended claims, the claimed invention may be practiced other than as explicitly described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device. In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer). Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements. All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out functionality.

The term "configured to" refers to an element with suitable structure to carry out a particular function. A suitable structure may be selected by a person having the benefit of this disclosure and at least ordinary skill in the art. As used herein, the term "configured to" may be used interchangeably with the terms "adapted to" or "structured to" unless the content of this disclosure clearly dictates otherwise.

Terms related to orientation, such as "proximal," "distal," "above," or "below," are used to describe relative positions of components and are not meant to limit the orientation of the embodiments contemplated.

Reference to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout are not necessarily referring to the same embodiment of the disclosure. Furthermore, the particular features, configurations, compositions, or characteristics may be combined in any suitable manner in one or more embodiments.

As used in this specification and the appended claims, the singular forms "a," "an," and "the" encompass embodiments having plural referents, unless the content clearly dictates otherwise. As used herein, "have," "having," "include," "including," "comprise," "comprising" or the like are used in their open-ended sense, and generally mean "including, but not limited to." It will be understood that "consisting essentially of," "consisting of," and the like are subsumed in "comprising," and the like.

The term "and/or" means one or all of the listed elements or a combination of at least two of the listed elements.

The phrases "at least one of," "comprises at least one of," and "one or more of" followed by a list refers to any one of the items in the list and any combination of two or more items in the list.

The invention claimed is:

1. A system comprising:
a first implantable lead comprising a distal portion and a first electrode coupled to the distal portion of the first implantable lead, wherein the first electrode is configured to be implanted at an implantation site on or in a tissue structure of a patient's heart; and
a second implantable lead comprising a distal portion and a second electrode coupled to the distal portion of the second implantable lead, wherein the second electrode is configured to be implanted at the implantation site distal to the first electrode within the tissue structure of the patient's heart, wherein the distal portion of the second implantable lead is guided by the distal portion of the first implantable lead to the implantation site, wherein the first implantable lead and the second implantable lead are aligned coaxial with one another.

2. The system according to claim 1, wherein the second electrode is translatable relative to the first electrode after the first electrode has been implanted to allow the second electrode to be implanted at various depths within the tissue structure of the patient's heart.

3. The system according to claim 1, wherein the first or second electrode is configured to deliver electrical pulses to test one or more depths of the respective electrode in the tissue structure of the patient's heart.

4. The system according to any preceding claim, wherein the second implantable lead is freely rotatable relative to the first implantable lead to facilitate implantation.

5. The system according to claim 1, wherein the second implantable lead is at least partially receivable into a lumen of the first implantable lead to guide the distal portion of the second implantable lead to the implantation site.

6. The system according to claim 1, wherein the implantation site is the triangle of Koch region in the atrioventricular wall of the patient's heart and the tissue structure is between the right atrium and left ventricle of the patient's heart.

7. The system according to claim 6, wherein the first electrode is implantable in the right atrium (RA) of the patient's heart to deliver cardiac therapy to or sense electrical activity of the RA of the patient's heart and the second electrode is implantable from the triangle of Koch region of the RA of the patient's heart to deliver cardiac therapy to or sense electrical activity of the left ventricle (LV) in the basal region, septal region, or basal-septal region of the left ventricular myocardium of the patient's heart.

8. The system according to claim 1 wherein the implantation site is the ventricular septal wall of the patient's heart and the tissue structure is between the right ventricle and the left ventricle of the patient's heart.

9. The system according to claim 8, wherein the first electrode is implantable closer to a first bundle branch of the cardiac conduction system of the patient's heart than the second electrode and the second electrode is implantable closer to a second bundle branch of the cardiac conduction system of the patient's heart than the first electrode.

10. The system according to claim 1, wherein the first electrode is implantable from the right ventricle (RV) of the patient's heart to deliver cardiac therapy to or sense electrical activity of the right bundle branch of the cardiac conduction system of the patient's heart and the second electrode is implantable from the RV of the patient's heart to deliver cardiac therapy to or sense electrical activity of the left bundle branch of the cardiac conduction system of the patient's heart.

11. The system according to claim 1, wherein the first implantable lead comprises a first fixation element formed integrally or separately from the first electrode.

12. The system according to claim 1, wherein the second implantable lead comprises a second fixation element formed integrally or separately from the second electrode.

13. The system according to claim 12, wherein the second fixation element comprises a drill or helix structure.

14. The system according to claim 1, wherein the second electrode is configured to pierce into the tissue structure of the patient's heart.

15. The system according to claim 1, further comprising a guide wire at least partially receivable into a lumen of the second implantable lead to pierce into the tissue structure of the patient's heart.

16. The system according to claim 1, further comprising a lead fixture element to mechanically couple to the first implantable lead and the second implantable lead.

17. The system according to claim 1, further comprising an electrical connector coupled to one or both of the first and second electrodes.

18. The system according to claim 17, wherein the electrical connector comprises a bifurcated proximal end.

19. The system according to claim 17, wherein the electrical connector comprises an inner conductor and two outer conductors.

20. A method comprising:
implanting a first electrode of a first implantable lead at an implantation site on or in a tissue structure of a patient's heart;
advancing a second implantable lead comprising a second electrode guided by a distal portion of the first implantable lead to the implantation site within the tissue structure of the patient's heart, the second implantable lead aligned coaxially with the first implantable lead; and
implanting the second electrode at the implantation site distal to the first electrode within the tissue structure of the patient's heart.

21. The method according to claim 20, further comprising translating the second electrode relative to the first electrode after the first electrode has been implanted to allow the second electrode to be implanted at various selectable depths within the tissue structure of the patient's heart.

22. The method according to claim 20, further comprising delivering electrical pulses to test one or more depths of the first or second electrode in the tissue structure of the patient's heart.

23. The method according to claim 20, wherein the first implantable lead and the second implantable lead are advanced concurrently toward the implantation site.

24. The method according to claim 20, further comprising advancing a guide wire to the implantation site, wherein the first implantable lead is guided over the guide wire to the implantation site.

25. An implantable medical device comprising:
a plurality of electrodes comprising:
a first electrode configured to be implanted at an implantation site on or in a tissue structure of a patient's heart; and
a second electrode configured to be implanted at the implantation site distal to the first electrode within the tissue structure of the patient's heart, wherein the second electrode is translatable relative to the first electrode after the first electrode has been implanted to allow the second electrode to be implanted at various depths within the tissue structure of the patient's heart, the second electrode translatable along a common axis shared by the first electrode and the second electrode;
a therapy delivery circuit operably coupled to the plurality of electrodes to deliver cardiac therapy to the patient's heart;
a sensing circuit operably coupled to the plurality of electrodes to sense electrical activity of the patient's heart; and
a controller comprising processing circuitry operably coupled to the therapy delivery circuit and the sensing circuit, the controller configured to provide electrical pulses to at least the second electrode to test one or more depths of the second electrode within the tissue structure of the patient's heart.

26. The device according to claim 25, wherein the second electrode is translatable relative to the first electrode after the first electrode has been implanted to allow the second electrode to be implanted at various selectable depths within the tissue structure of the patient's heart.

27. The device according to claim 25 or 26, wherein the second electrode is configured to deliver electrical pulses from the therapy delivery circuit to test one or more depths of the first electrode in the tissue structure of the patient's heart.

28. The device according to claim 25, wherein the first electrode and the second electrode are integrated into a single lead assembly configured to concurrently advance the first electrode and the second electrode toward the implantation site.

* * * * *